US011884917B2

(12) United States Patent
Elling et al.

(10) Patent No.: US 11,884,917 B2
(45) Date of Patent: Jan. 30, 2024

(54) CONDITIONAL CRISPR SGRNA EXPRESSION

(71) Applicants: IMBA—INSTITUT FÜR MOLEKULARE BIOTECHNOLOGIE GMBH, Vienna (AT); CAMPUS SCIENCE SUPPORT FACILITIES GMBH, Vienna (AT)

(72) Inventors: Ulrich Elling, Perchtoldsdorf (AT); Krzysztof Chylinski, Vienna (AT); Maria Hubmann, Vienna (AT); Monika Borowska, Vienna (AT); Ivana Bilusic-Vilagos, Vienna (AT)

(73) Assignees: IMBA—INSTITUT FÜR MOLEKULARE BIOTECHNOLOGIE GMBH, Vienna (AT); CAMPUS SCIENCE SUPPORT FACILITIES GMBH, Vienna (AT)

( * ) Notice: Subject to any disclaimer, the term of this patent is extended or adjusted under 35 U.S.C. 154(b) by 1026 days.

(21) Appl. No.: 16/085,810

(22) PCT Filed: Mar. 17, 2017

(86) PCT No.: PCT/EP2017/056364
§ 371 (c)(1),
(2) Date: Sep. 17, 2018

(87) PCT Pub. No.: WO2017/158153
PCT Pub. Date: Sep. 21, 2017

(65) Prior Publication Data
US 2019/0085325 A1 Mar. 21, 2019

(30) Foreign Application Priority Data
Mar. 17, 2016 (EP) .................................. 16160947

(51) Int. Cl.
*C12N 15/11* (2006.01)
*C12N 15/63* (2006.01)
*C12N 9/22* (2006.01)
*C12N 15/86* (2006.01)
*C12N 9/12* (2006.01)
*C12N 15/90* (2006.01)

(52) U.S. Cl.
CPC ............ *C12N 15/11* (2013.01); *C12N 9/1241* (2013.01); *C12N 9/22* (2013.01); *C12N 15/111* (2013.01); *C12N 15/63* (2013.01); *C12N 15/86* (2013.01); *C12N 15/907* (2013.01); *C12N 2310/20* (2017.05); *C12N 2330/51* (2013.01); *C12N 2800/30* (2013.01)

(58) Field of Classification Search
CPC .......... C12N 2800/30; C12N 2310/20
See application file for complete search history.

(56) References Cited

FOREIGN PATENT DOCUMENTS

| CN | 104404036 A | * | 3/2015 | | |
|---|---|---|---|---|---|
| WO | WO-2004056964 A2 | * | 7/2004 | ............ | C12N 15/111 |
| WO | WO-2015048690 A1 | * | 4/2015 | ............. | C12N 15/11 |
| WO | 2015089465 A1 | | 6/2015 | | |

OTHER PUBLICATIONS

Machine translation of CN104404036A, printed as pp. 1-21 on Jun. 4, 2021. (Year: 2021).*
Kasim et al (Nucleic Acids Research, vol. 32, No. 7, e66, Apr. 23, 2004, printed as pp. 1/8-8/8. (Year: 2004).*
Konermann et al (Nature, vol. 517, pp. 583-588, Jan. 2015, including pp. 1/2-2/2 of Methods, pp. 1/10-10/10 of Extended Data, and pp. 1/28/-28/28 of Supplementary Information, Epub Dec. 10, 2014. (Year: 2014).*
Extended European Search Report for EP Application No. 16160947.7 dated Jan. 13, 2017 (13 pages).
Anton, T., "Visualization of specific DNA sequences in living mouse embryonic stem cells with a programmable fluorescent CRISPR/Cas system," Nucleus 5:2, Mar./Apr. 2014, pp. 163-172.
Aubrey, B., "An Inducible Lentiviral Guide RNA Platform Enables the Identification of Tumor-Essential Genes and Tumor-Promoting Mutations In Vivo," Cell Reports 10, Mar. 3, 2015, pp. 1422-1432.
Briner, A., "Guide RNA Functional Modules Direct Cas9 Activity and Orthogonality," Molecular Cell 56, Oct. 23, 2014, pp. 333-339.
Chavez, A., "Highly-efficient Cas9-mediated transcriptional programming," Nat Methods, Apr. 2015, 12(4), pp. 326-328.
Chen, B., "Dynamic Imaging of Genomic Loci in Living Human Cells by an Optimized CRISPR/Cas System," Cell 155, Dec. 19, 2013, pp. 1479-1491.
Cheng. A., "Casilio: a versatile CRISPR-Cas9-Pumilio hybrid for gene regulation and genomic labeling," Cell Research, 2016, vol. 26 No. 2, pp. 254-257.
Cho, S., "Analysis of off-target effects of CRISPR/Cas-derived RNA-guided endonucleases and nickases," Genome Research, 2014, 24, pp. 132-141.

(Continued)

*Primary Examiner* — Jennifer Dunston
(74) *Attorney, Agent, or Firm* — Greer, Burns & Crain, Ltd

(57) ABSTRACT

An expression cassette for conditional expression of a single guide RNA (sgRNA) of a CRISPR/Cas9 system, the cassette includes a promoter, an sgRNA sequence, and a sequence flanked by at least a pair of recombinase recognition sites, wherein recombinase activated re-combination at the pair of recombinase recognition sites is capable of excising said flanked sequence, whereby either i) at least one of said recombinase recognition sites is located within the sgRNA sequence and said flanked sequence contains an transcription disruption sequence or ii) said flanked sequence is at least a part of the promoter or of the sgRNA sequence; methods of conditional expression of sgRNA and a reaction product of the conditional expression, i.e. sgRNA with a recombination site remnant.

Figure 1:
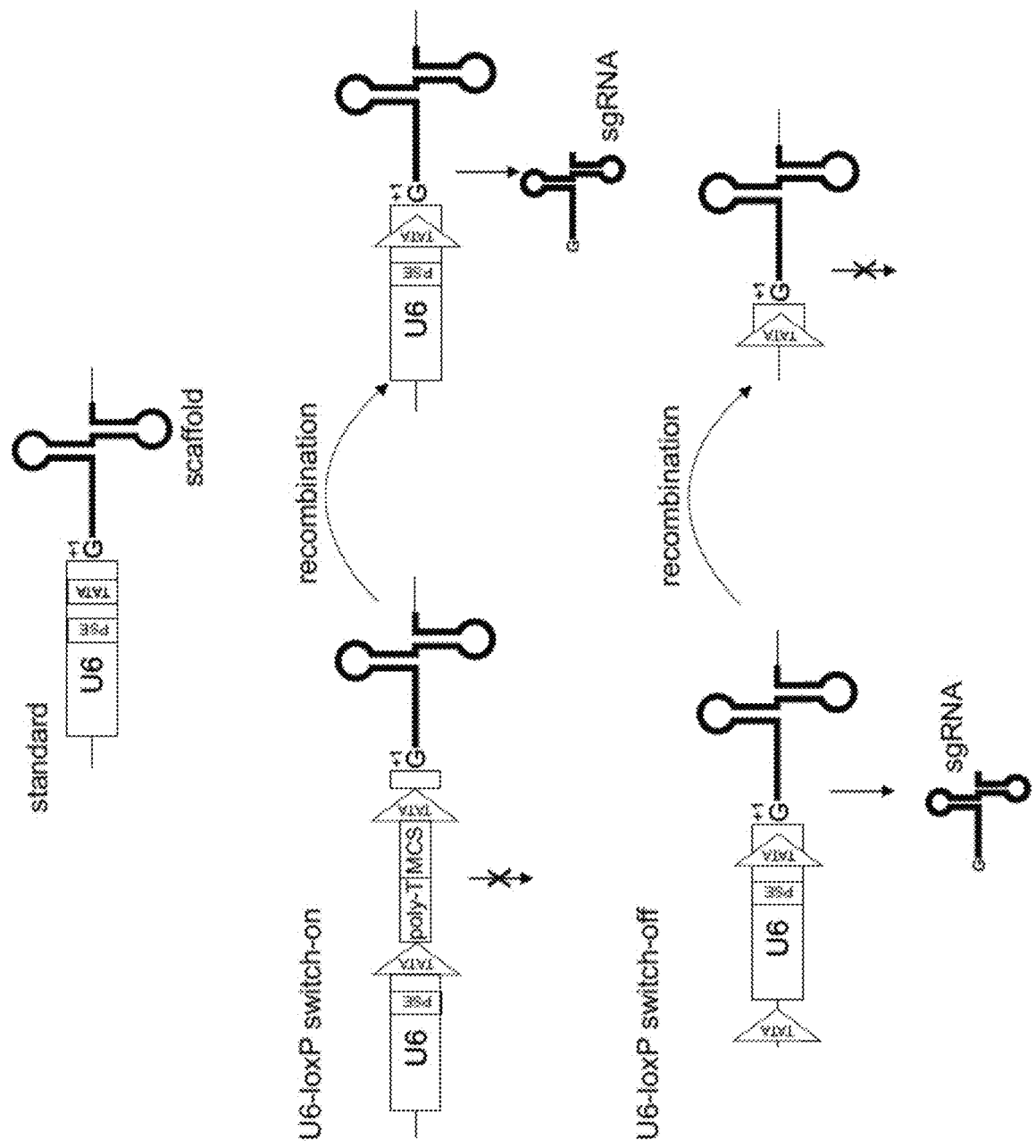

9 Claims, 19 Drawing Sheets
Specification includes a Sequence Listing.

(56) References Cited

OTHER PUBLICATIONS

Chylinski, K., "Classification and evolution of type II CRISPR-Cas systems," Nucleic Acids Research, 2014, vol. 42, No. 10, pp. 6091-6105.
Cong, L., "Multiplex Genome Engineering Using CRISPR/Cas Systems," Science, Feb. 15, 2013, vol. 339, pp. 820-823.
Deltcheva, E., "CRISPR RNA maturation by trans-encoded small RNA and host factor RNase III," Nature, Mar. 31, 2011, vol. 471, pp. 602-609.
Deng, W., "CASFISH: CRISPR/Cas9-mediated in situ labeling of genomic loci in fixed cells," PNAS, Sep. 22, 2015, vol. 112, No. 38, pp. 11870-11875.
Dominguez, A., "Beyond editing: repurposing CRISPR-Cas9 for precision genome regulation and interrogation," Molecular Cell Biology (Nature Reviews), Dec. 16, 2015, vol. 17, pp. 5-15.
Doudna, J., "The new frontier of genome engineering with CRISPR-Cas9," Science, Nov. 25, 2014, vol. 346, Issue 6213, pp. 1077 (Review Summary), pp. 1258096-1-1258096-9 (Full Review).
Dow, L., "Inducible in vivo genome editing with CRISPR-Cas9," Nature Biotechnology, Apr. 2015, vol. 33, No. 4, pp. 390-396.
Du, D., "An Introduction to CRISPR Technology for Genome Activation and Repression in Mammalian Cells," Cold Spring Harb Protoc, 2016, pp. 1-4.
East-Seletsky, A., "Two distinct RNase activities of CRISPR-C2c2 enable guide-RNA processing and RNA detection," Nature, Oct. 13, 2016, vol. 538, pp. 270-286.
Esvelt, K., "Orthogonal Cas9 proteins for RNRNA-guided gene regulation and editing," Nature Methods, Nov. 2013, vol. 10, No. 11, pp. 1116-1123.
Fonfara, I., "Phylogeny of Cas9 determines functional exchangeability of dual-RNA and Cas9 among orthologous type II CRISPR-Cas systems," Nucleic Acids Research, 2014, vol. 42, No. 4, pp. 2577-2590.
Geiduschek, E., "The RNA Polymerase III Transcription Apparatus," J. Mol. Biol., 2001, 310, pp. 1-26.
Gilbert, L., "CRISPR-Mediated Modular RNA-Guided Regulation of Transcription in Eukaryotes," Cell, Jul. 18, 2013, 154, pp. 442-451.
Guilinger, J., "Fusion of catalytically inactive Cas9 to FokI nuclease improves the specificity of genome modification," Nature Biotechnology, Jun. 2014, vol. 32, No. 6, pp. 577-582.
Hendriks, W., "Genome Editing in Human Pluripotent Stem Cells: Approaches, Pitfalls, and Solutions," Cell Stem Cell 18, Jan. 7, 2016, pp. 53-65.
Hilton, I., "Epigenome editing by a CRISPR-Cas9-based acetyltransferase activates genes from promoters and enhancers," Nature Biotechnology, May 2015, vol. 33, No. 5, pp. 510-519.
Hsu, P., "Development and Applications of CRISPR-Cas9 for Genome Engineering," Cell, Jun. 5, 2014, 157(6), pp. 1262-1278.
Jinek, M., "A Programmable Dual-RNA-Guided DNA Endonuclease in Adaptive Bacterial Immunity," Science, Aug. 17, 2012, vol. 337, pp. 816-821.
Kearns, N., "Functional annotation of native enhancers with a Cas9-histone demethylase fusion," Nature Methods, May 2015, vol. 12, No. 5, pp. 401-406.
Kleinstiver, B., "Engineered CRISPR-Cas9 nucleases with altered PAM specificities," Nature, Jul. 23, 2015, vol. 523, pp. 481-497.
Kleinstiver, B., "Broadening the targeting range of *Staphylococcus aureus* CRISPR-Cas9 by modifying PAM recognition," Nature Biotechnology, Dec. 2015, vol. 33, No. 12, pp. 1293-1299.
Kleinstiver, B., "High-fidelity CRISPR-Cas9 nucleases with no detectable genome wide off-target effects," Nature, Jan. 28, 2016, vol. 529, pp. 490-506.
Konermann, S., "Genome-scale transcriptional activation by an engineered CRISPR-Cas9 complex," Nature, Jan. 29, 2015, vol. 517, pp. 583-600.
Lei, Q., "Repurposing CRISPR as an RNA-Guided Platform for Sequence-Specific Control of Gene Expression," Cell 152, Feb. 28, 2013, pp. 1173-1173.

Lescure, A., "The different positioning of the proximal sequence element in the Xenopus RNA polymerase II and III snRNA promoters is a key determinant which confers RNA polymerase III specificity," Nucleic Acids Research, Jan. 1991, vol. 19, No. 3, pp. 435-441.
Ma, H., "Pol III Promoters to Express Small RNAs: Delineation of Transcription Initiation," Nucleic Acids, 2014, 3, 11 pages.
Mali, P., "CAS9 transcriptional activators for target specificity screening and paired nickases for cooperative genome engineering," Nature Biotechnology, Sep. 2013, vol. 31, No. 9, pp. 833-840.
Muller, M., "*Streptococcus thermophilus* CRISPR-Cas9 Systems Enable Specific Editing of the Human Genome," Molecular Therapy, Mar. 2016, vol. 24, No. 3, pp. 636-644.
Nihongaki, Y., "Photoactivatable CRISPR-Cas9 for optogenetic genome editing," Nature Biotechnology, Jul. 2015, vol. 33, No. 7, pp. 755-762.
Nishimasu, H., "Crystal Structure of Cas9 in Complex with Guide RNA and Target DNA," Cell 156, Feb. 27, 2014, pp. 935-949.
Perez-Pinera, P., "RNA-guided gene activation by CRISPR Cas9-based transcription factors," Nature Methods, Oct. 2013, vol. 10, No. 10, pp. 973-978.
Ran, F., "Double Nicking by RNA-Guided CRISPR Cas9 for Enhanced Genome Editing Specificity," Cell 154, Sep. 12, 2013, pp. 1380-1389.
Ran, F., "Genome engineering using the CRISPR-Cas9 system," Nature Protocols, 2013, vol. 8, No. 11, pp. 2281-2308.
Savic, N., "Advances in therapeutic CRISPR/Cas9 genome editing," Translational Research, Feb. 2016, vol. 168, pp. 15-21.
Shechner, D., "Multiplexable, locus-specific targeting of long RNAs with CRISPR-Display," Nature Methods, Jul. 2015, vol. 12, No. 7, pp. 664-675.
Slaymaker, I., "Rationally engineered Cas9 nucleases with improved specificity," Science: Research Reports, Jan. 1, 2016, vol. 351, No. 6268, pp. 84-88.
Steinert, J., "Highly efficient heritable plant genome engineering using Cas9 orthologues from *Streptococcus thermophilus* and *Staphylococcus aureus*," The Plant Journal, 2015, 84, pp. 1295-1305.
Tijssen, P., "Hybridization with Nucleic Acid Probes," Laboratory Techniques in Biochemistry and Molecular Biology, Jan. 1994, vol. 24, 1 page.
Truong, D. "Development of an intein-mediated split-Cas9 system for gene therapy," Nucleic Acids Research, 2015, vol. 43, No. 13, pp. 6450-6458.
Tsai, S., "Dimeric CRISPR RNA-guided FokI nucleases for highly specific genome editing," Nature Biotechnology, Jun. 2014, vol. 32, No. 6, pp. 569-576.
Ventura, A., "Cre-lox-regulated conditional RNA interference from transgenes," PNAS, Jul. 13, 2004, vol. 101, No. 28, pp. 10380-10385.
Wiles, M., "CRISPR-Cas9-mediated genome editing and guide RNA design," Mamm Genome, 2015, 26, pp. 501-510.
Wright, A., "Rational design of a split-Cas9 enzyme complex," PNAS, Mar. 10, 2015, vol. 112, No. 10, pp. 2984-2989.
Xu, K., "Efficient genome engineering in eukaryotes using Cas9 from *Streptococcus thermophilus*," Cell. Mol. Life Sci., Jul. 10, 2015, pp. 383-399.
Zalatan, J., "Engineering Complex Synthetic Transcriptional Programs with CRISPR RNA Scaffolds," Cell 160, Jan. 15, 2015, pp. 339-350.
Zetsche, B., "A split-Cas9 architecture for inducible genome editing and transcription modulation," Nature Biotechnology, Feb. 2015, vol. 33, No. 2, pp. 139-142.
Zetsche, B., "Cpf1 Is a Single RNA-Guided Endonuclease of a Class 2 CRISPR-Cas System," Cell 163, 2015, pp. 759-771.
Zuris, J., "Cationic lipid-mediated delivery of proteins enables efficient protein-based genome editing in vitro and in vivo," Nature Biotechnology, Jan. 2015, vol. 33, No. 1, pp. 73-80.
International Search Report and Written Opinion for PCT/EP2017/056364 dated Jul. 10, 2017 (17 pages).
Carlson-Stevermer, J., et al., "Assembly of CRISPR ribonucleoproteins with biotinylated oligonucleotides via an RNA aptamer for precise gene editing", Nature Communications, 2017, pp. 1-13, vol. 8, No. 1711.

(56) References Cited

OTHER PUBLICATIONS

Carlson-Stevermer, J., et al., "Assembly of CRISPR ribonucleoproteins with biotinylated oligonucleotides via an RNA aptamer for precise gene editing", Nature Communications, 2017, pp. 1-13, vol. 8, No. 1711, (Supplemental Information), printed as pp. 1-22.

Kundert, K., et al., "Controlling CRISPR-Cas9 with ligand-activated and ligand-deactivated sgRNAs", Nature Communications, 2019, pp. 1-11, vol. 10, No. 2127.

Kundert, K., et al., "Controlling CRISPR-Cas9 with ligand-activated and ligand-deactivated sgRNAs", Nature Communications, 2019, pp. 1-11, vol. 10, No. 2127, (Supplemental Information), printed as pp. 1/29-29/29.

* cited by examiner

CONDITIONAL CRISPR SGRNA EXPRESSION

BACKGROUND OF THE INVENTION

CRISPR/Cas9 technology has revolutionized genome engineering providing easy, efficient and affordable tool for site-specific genetic modification and regulation (Doudna & Charpentier, 2014; Hsu, Lander, & Zhang, 2014). Since its discovery in 2012, the system has been successfully used in variety of primary cells, cell lines and organisms including virtually all model systems. CRISPR/Cas9 is a derivative of bacterial adaptive immune system, type II CRISPR (Chylinski, Makarova, Charpentier, & Koonin, 2014). In both natural and engineered systems, Cas9 is a dual endonuclease capable of inducing specific double stranded DNA breaks (Jinek et al., 2012). The targeting specificity is provided by short RNA(s) bound to Cas9 composed of Cas9-binding scaffold and 20 nt customizable guiding sequence base-pairing with a desired sequence of target DNA. In recent years multiple research groups investigated and improved the system by modification of scaffolds for higher efficiency and by proposing guidelines for target site choice providing more specific and active cleavage (Hsu et al., 2014).

While very promising and widely used in both basic and applied research, including possible therapeutic applications, the technology needs further improvement. Obtaining predictable and high cutting efficiency, especially in combination with high specificity, is still a challenge. Furthermore, while inducible systems for Cas9 expression have been developed (Aubrey et al., 2015; Dow et al., 2015; Wright et al., 2015; Zetsche, Volz, & Zhang, 2015), no tight inducible systems (ON or OFF) for guide RNA (sgRNA) expression transcribed in vivo from RNA polymerase III promoters have been reported till date, except an imperfect and leaky Tet-inducible system based on doxycycline induced derepression (Aubrey et al., 2015).

CN 104 404 036 A (automatic google translation) relates to the generation of transgenic mice with tissue-specific expression of a sgRNA. Ventura et al. 2004 relates to Cre-Lox systems for RNA interference. Brandon et al. 2015 relates to using CRISPR/Cas9 to identify tumor-essential genes.

SUMMARY OF THE INVENTION

The invention provides an expression cassette for expression of a single guide RNA (sgRNA) of a CRISPR/Cas9 system, said cassette comprises a promoter, an sgRNA sequence, and a sequence flanked by at least a pair of recombinase recognition sites, wherein recombinase activated recombination at the pair of recombinase recognition sites is capable of excising said flanked sequence, whereby either i) at least one of said recombinase recognition sites is located within the sgRNA sequence and said flanked sequence contains an transcription disruption sequence ("off-to-on switch") or ii) said flanked sequence is at least a part of the promoter or of the sgRNA sequence ("on-to-off switch").

According to an off-to-on switch embodiment, the invention further provides an expression cassette for expression of an sgRNA of the CRISPR/Cas9 system upon recombinase mediated activation, said cassette comprises a promoter, an sgRNA sequence, and a transcription disruption sequence flanked by at least a pair of recombinase recognition sites (e.g. with the same 5'-3' orientation), wherein said flanked transcription disruption sequence interrupts the sgRNA sequence.

According to an on-to-off switch embodiment, provided is an expression cassette for expression of an sgRNA of the CRISPR/Cas9 system until recombinase mediated inactivation, said cassette comprises a promoter, an sgRNA sequence that contains a DNA guiding sequence, and at least a pair of recombination recognition sites, wherein said recombination sites are in the same orientation and flank either at least a part of the promoter upstream of the DNA guiding sequence or a at least a part of the sgRNA sequence downstream of the DNA guiding sequence.

Related to an off-to-on embodiment, also provided is a method of expressing an sgRNA of the CRISPR/Cas9 system upon recombinase stimulation, comprising
  A) providing a cell with an expression cassette comprising a promoter and an sgRNA sequence, wherein said sgRNA is interrupted by a transcription disruption sequence flanked by at least a pair of recombinase recognition sites (e.g. with the same 5'-3' orientation);
  B) introducing or activating a recombinase in the cell, thereby removing the transcription disruption sequence,
  C) cultivating the cell under conditions allowing expression of the sgRNA sequence.

Related to an on-to-off embodiment, provided is a method of expressing an sgRNA of the CRISPR/Cas9 system until recombinase stimulation, comprising
  A) providing a cell with an expression cassette comprising a promoter, an sgRNA sequence that contains a DNA guiding sequence, and at least a pair of recombination recognition sites, wherein said recombination recognition sites flank either at least a part of the promoter upstream of the DNA guiding sequence or a at least a part of the sgRNA sequence downstream of the DNA guiding sequence or both (i.e. flank the joining or intermediate region with parts of both, the promoter and the sgRNA);
  B) cultivating the cell under conditions allowing expression of the sgRNA sequence.
  C) introducing or activating a recombinase in the cell, thereby deleting the sequence flanked by the recombination recognition sites.

Phrased for both, A) off-to-on and B) on-to-off, embodiments, the invention provides a method for conditionally modifying a target DNA comprising the step of
  providing a cell with an expression construct comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first site-specific recombinase site is located between the promoter and the loop of the Cas9 binding element of said single guide RNA coding element, and a second of said site-specific recombinase recognition sites is located either upstream or downstream of said first site-specific recombinase site:
    A) wherein the construct is prevented from expressing the sgRNA in a cell by placement of a transcription disruption sequence that disrupts expression of the sgRNA, between said site-specific recombinase recognition sites, said transcription disruption sequence is excised upon recombinase mediated recombination at the recombinase recognition sites, thereby allowing recombinase dependent conditional expression of the sgRNA; or B) wherein the construct allows expressing the sgRNA by lack of a disrupting element between the site-specific recombinase recognition sites, said expression is conditionally prevented upon contacting the construct with a recombinase, whereupon recombinase mediated recombination of the recombinase recognition sites excises a nucleic acid portion required for transcription of the sgRNA, said nucleic acid portion being selected from at least a part of the promotor or at least a part of the sgRNA sequence or both;

wherein in allowed expression configuration according to either A) or B) the single guide RNA is expressed and forms a complex with a Cas9 protein and said complex modifies the target DNA at a sequence site hybridizing to the DNA guiding element.

Based on the same phraseology, the invention provides for both embodiments, a construct for conditionally modifying a target DNA in a Cas9 complex, comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first site-specific recombinase recognition sites is located between the promoter and the loop of the Cas9 binding element of said single guide RNA sequence, and a second of said site-specific recombinase recognition sites is located either upstream or downstream of said first site-specific recombinase site:

A) wherein the construct is unsuitable for expressing the sgRNA sequence in a cell by an transcription disruption sequence between said site-specific recombinase recognition sites, which is excisable upon recombinase mediated recombination of the recombinase recognition sites, thereby allowing conditional expression of the sgRNA; or B) wherein the construct is suitable for expressing the sgRNA by lack of a transcription disruption sequence between the site-specific recombinase recognition sites, and said recombinase recognition sites flank a nucleic acid portion required for transcription of the single guide RNA, said nucleic acid portion being selected from at least a part of the promotor or at least a part of the sgRNA sequence or both.

The invention also provides a method of limiting activity of a complex by expressing at least two parts of said complex subsequently by expressing a construct encoding a first part of the complex and a second part of said complex, wherein said second part is disrupted by the first part flanked by site-specific recombinase recognition sites, whereby only the first part is expressed; excising the first part by recombinase mediated recombination of the recombinase recognition sites, thereby removing the disruption of the second part and allowing the second part to be expressed; allowing complex formation of the produced first part and second part to form a complex, preferably wherein said complex is a reaction complex or a binding complex or both.

Also provided is a method of limiting the activity of a Cas9-sgRNA complex comprising A) providing a cell with an expression construct comprising a promoter, an sgRNA sequence, wherein said sgRNA sequence is disrupted by a coding sequence of the Cas9 protein flanked by directly oriented recombinase recognition sites;

B) culturing said cell under conditions suitable for the expression of the Cas9 protein, C) introducing or activating a recombinase in the cell, thereby removing the Cas9 sequence flanked by the recombination recognition sites and hence the disruption of the sgRNA sequence, D) culturing said cell under conditions suitable for the expression of the sgRNA, whereby said sgRNA forms a complex with the Cas9 protein formed in step B) and said complex potentially modifies a target DNA at a sequence site hybridizing to a DNA guiding element of the sgRNA.

The invention further provides a single guide RNA comprising a sequence of a recombinase site, preferably a loxP site or a FRT site; preferably wherein said recombinase site is in a loop linking a stem of a Cas9 binding element and its complementary. This single guide RNA can be produced by the inventive methods, especially the off-to-on methods.

The invention further provides the use of any one of the inventive constructs for a method of use in the conditional activation of the CRISPR/Cas9 system, especially for sgRNA expression, in particular like defined in any one of the inventive methods.

The invention further provides the use of the inventive constructs or methods in screening for mutations in a target DNA that is targeted by the sgRNA, in particular its DNA binding sequence. The target DNA may be a typical CRISPR target, especially a protospacer sequence adjacent to a PAM sequence.

All embodiments of the invention are described together in the following detailed description and all preferred embodiments relate to all embodiments, aspects, methods and constructs alike. E.g. descriptions of constructs as such also read on the constructs and means used in the inventive methods. Preferred and detailed descriptions of the inventive methods read alike on suitability's and requirements of the inventive constructs or products, like the expressed sgRNA. All embodiments can be combined with each other, except where otherwise stated. Even off-to-on and on-to-off description can read on each other, where the requirements are the same. Furthermore it is possible to combine off-to-on and on-to-off embodiments in one construct, e.g. by using different recombinase systems, so that sgRNA expression can be provided in "on", turned "off" and then turned "on" again, or vice-versa by the providing "off", turning "on", then turning "off" again.

DETAILED DESCRIPTION OF THE INVENTION

The present invention provides the use of recombinase systems to conditionally turn expression of an sgRNA of the CRISPR/Cas9 system on or off. These are referred to as "off-to-on" and "on-to-off" embodiments respectively herein. For both embodiments, recombinase recognition sites can be placed similarly in an sgRNA expression construct, typically comprised of a promoter and a "coding" sequence for the sgRNA. By action of the recombinase, a sequence within a pair of recombinase recognition sites is removed, typically by recombination of the sites with each other and excision of the sequence within. This removal can either remove a block (a "transcription disrupting sequence"), which will switch "off-to-on" (or just "on") or remove a required element for expression of a functional sgRNA, which will switch "on-to-off". In the on-to-off (or just "off") variant the required element may be in the promoter, leading to a loss of promoter activity or in the sgRNA, leading to an incomplete or non-functional sgRNA. Likewise, in the "on" variant, a blocking element in these parts of an expression construct may be removed to allow sgRNA expression.

According to a general aspect of the invention, provided is an expression cassette for expression of a single guide RNA (sgRNA) of a CRISPR/Cas9 system, said cassette comprises a promoter, an sgRNA sequence, and a sequence flanked by at least a pair of recombinase recognition sites, wherein recombinase activated recombination at the pair of recombinase recognition sites is capable of excising said flanked sequence. The sgRNA sequence on the cassette encodes a sgRNA, which is expressed by function of the promoter. Usually, i) at least one of said recombinase recognition sites is located within the sgRNA sequence or its promoter and said flanked sequence contains a transcription disruption sequence. This is an "off-to-on switch" embodiment. Alternatively (or in combination) ii) said flanked sequence is at least a part of the promoter or of the sgRNA sequence without an interrupting sequence. The presence of the recombinase recognition sites alone does not prevent CRISPR/Cas9 activity. This is an "on-to-off switch" embodiment.

Since its discovery in 2012, CRISPR/Cas9 has been established as a tool for biomedical research in multiple model organisms and proven high efficiency and specificity. However, generation of homozygous alleles is still challenging. Furthermore, truly tight inducibility of sgRNA is a prerequisite for the optimal use of this technology in vitro and in vivo. Inducible Cas9 expression systems have been already described, however the inventive sgRNA switch on/off system will allow tighter regulation and it can be used in already established cell lines and model organisms expressing Cas9 constitutively or intermittently. Alternatively, Cas9 can be introduced with or even on the inventive construct. Moreover, leakiness was observed for doxycyclin-inducible Cas9 (Dow et al., 2015) and tight systems of rapamycin induced split-Cas9 have a decreased cleavage activity. These problems are overcome by the inventive recombinase-based systems.

In conventional conditional knockout technology exons are flanked with site specific recombination sites. Such an approach is at a disadvantage in a CRISPR/Cas9 system, because deletion of the entire cassette leads to loss of guide DNA from cells and thereby prevents readout in later identification methods. Also, no such approach allows for an inducible on switch of sgRNA expression as a classical floxed (flanked by lox) STOP cassette used in regulation of polymerase II transcripts expression that is usually inserted within non-coding sequences like 5'UTRs. These are not present in RNA polymerase III transcripts. RNA polymerase III is one of the main polymerases of the CRISPR/Cas9 system, although method variants with polymerase II exist (WO2015/153940). These can be employed in for the expression of the inventive sgRNA as well.

Although a recent discovery, the CRISPR/Cas9 system is well-known in the art and known in detail. A detailed description can be found in WO2013/176772, and in the family of WO2014/093595, which includes WO2014/093622, WO2014/093635, WO2014/093655, WO2014/093661, WO2014/093694, WO2014/093701, WO2014/093709, WO2014/093712, WO2014/093718, WO2014/204723, WO2014/204724, WO2014/204725, WO2014/204726, WO2014/204727, WO2014/204728, WO2014/204729; further in WO2014/093479, WO2014/191518 and the scientific publications cited herein (all incorporated herein by reference). Briefly, as explained in Jinek et al. (2012), Cas9 proteins constitute a family of enzymes that require a base-paired structure formed between the activating tracrRNA and the targeting crRNA to cleave target DNA. The crRNA is also referred to as guideRNA for containing the DNA guiding sequence. The tracrRNA and the crRNA can be linked to form a single molecule called single guide RNA (sgRNA). tracrRNA (trans-activating crRNA) and crRNA (CRISPR RNA) hybridize in a complementary region. This complementary region can be used for the linkage and, together with a linkage, may form a stem-loop, called the crRNA:tracrRNA stem loop herein. Since this region also mediates binding to Cas9 protein, it may also be referred to as Cas9 binding element. Site-specific cleavage occurs at locations determined by both base-pairing complementarity between the crRNA and the target protospacer DNA and a short motif [referred to as the protospacer adjacent motif (PAM)] juxtaposed to the complementary region in the target DNA. The target DNA may be in any DNA molecule that should be modified. It may be of a gene that shall be modified. A typical use of the Cas9/CRISPR/Cas9 system is to introduce mutations. One possible mechanism is by repeated cutting and repair of the cut, wherein at one point in time, the repair is faulty and introduces a mutation. Apart from cutting the target DNA, other modifications of the DNA are possible depending on the used Cas9 protein. Such further modifications include insertions, deletions, methylations or alterations in transcription of the target DNA (e.g. by dCas9 or dCas9 fusions with transcriptional repressors or activators). Alternations in transcription include suppression of transcription, activation or increase in transcription, which can be facilitated by selection of a suitable Cas9 protein as is explained below, e.g.—but not necessarily—a fusion protein with repressors or activators. Transcriptional activation or suppression can e.g. be used for screening for a particular phenotype of activated or suppressed genes in cells or organisms (WO2016/011080). Another use is to increase the rate of homologous recombination wherein a recombination DNA molecule is introduced into the location of the target DNA. Modifying, especially cutting, the target DNA tremendously increases homologous recombination and its sequence replacement by the recombination DNA.

The sequence of the sgRNA allows many variations as long as it is capable of binding Cas9 and having a protospacer hybridizing region or complementary region. Methods to determine and design such binding regions are known in the art and are e.g. possible by computer based design. Such analysis and modifications of the CRISPR/Cas9 system, including sgRNA design are disclosed in WO2015/089364, WO2014/191521 and WO2015/065964. Usually, the sgRNA that is active in the CRISPR/Cas9 system has a i) 5' start (typically a G, guanosine nucleotide), ii) a DNA guiding element or sequence, iii) a Cas9 binding element or sequence, and iv) optionally a 3' portion, that may or may not contain one or more further structural stem loops. These structural stem loops are usually few in number and small, e.g. with a stem of 3-50 nucleotides in length. The distance from the 5' start to the DNA guiding element or sequence can be 0 (i.e. the start is part of the DNA guiding element) to 40 nt (nucleotides), preferably 0 to 20, or 0 to 10 nt or even 1 to 5 nt in length. The DNA guiding element or sequence can be 8 to 50 nt in length, preferably 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 42, 44, 46, 48 nt in length or any range in between; preferred are 15-30 nt in length an even more preferred length is 17-19 nt, which minimizes off-target events (Wiles et al., *Mamm Genome* (2015) 26:501-510). The distance between the DNA guiding element or sequence and the Cas9 binding element or sequence may be 0 nt (directly adjacent) to 30 nt, preferably 0 nt to 20 nt or 2 to 10 nt in length. The Cas9 binding element or sequence is preferably a stem loop or at least a ds (double strand) region of a hybridizing region. Preferably the stem or hybridizing region has of 6 to 50 nt in length, e.g. 7, 8, 9, 10, 11, 12, 13, 14, 15, 16, 17, 18, 19, 20, 21, 22, 23, 24, 25, 26, 27, 28, 30, 32, 34, 36, 38, 40, 45, 50 nt or more in length or any range in between these values. The stem or hybridizing region may have 60% to 100% complementary nucleotides, including A-U (coded by T on the sense strand of a dsDNA), G-C and G-U(coded by T) base pairs. Preferably the complementary nucleotides are 70% to 95% or 80% to 90%. The sequence of the loop is not very important; it may even protrude the Cas9 binding region, and leave only the hybridizing region in the Cas9 binding pocket and hence the loop is not binding relevant. Cas9 binding of sgRNA leads to the formation of a Cas9 complex. The 3' portion of the sgRNA may be 20 to 600 nt in length. Usually this region can be designed relatively freely. If too long, it may even be digested by naturally occurring enzymes, which will automatically result in a suitable size for the Cas9/CRISPR/Cas9 system. Possible lengths are 20 to 400 nt, 25 to 300 nt or 30 to 200 nt. In total, the sgRNA has preferably a size 60 100 to 2000 nt in length, preferably 70 to 1500 nt, or 80 to 1000 nt, 90 to 800 nt, 100 to 500 nt, 120 to 300 nt in length.

The DNA guiding element or protospacer complementary region can be chosen freely to hybridize a target DNA. sgRNA/CRISPR targeting and methods of selecting suitable DNA guiding sequences and modifications of the guide RNA are disclosed in WO2014/093709, WO2014/144761, WO2015/089486, WO2015/048577, WO2015/123339, WO2015089486, WO2015/089427, WO2014/144592, WO2014/204578, WO2015/113063. These pre-disclosed methods including determining both on- and off-target sites to minimize unwanted side-reactions. All of these methods can be used according to the invention.

The inventive construct for expressing the sgRNA contains recombinase recognition sites. These may be selected from conventional recombinase recognition sites such as frt or lox sequences, preferably loxP, lox 66 or lox 71 sequences. At least two of them are used to form a pair that allows interaction with each other and upon recombinase interaction excision or deletion of the sequence in between these sited (the "flanked" sequence). Usually the pair of recombinase interaction excision is in the same 5'-3' orientation, which helps to mediate such an excision reaction.

The recombinase is preferably selected from the group of tyrosine recombinases, including Cre, Flp, XerC/D and FimB/E, or from the group of serine recombinases, such as hin, gin and cin. Any site for these recombinases can be used as recombinase recognition sites. A site specific recombinase binds to its DNA binding site or "recombinase recognition site" or "target" at the at least two sites. Usually by action of enzyme aggregation, the at least two sites are brought into vicinity and are oriented in parallel. The double stranded DNA is modified, e.g. with a cutting step, at both recombinase recognition sites by the recombinase. The strands are then rejoined with DNA ligase in a quick and efficient process. The result of recombination depends on the orientation of the recombinase recognition sites. Two recombinase recognition sites in a direct repeat, i.e. in the same orientation, of recombinase recognition sites will cause a deletion event of the sequence flanked by the at least two recombinase recognition sites. Two recombinase recognition sites in an inverse repeat will cause an inversion event of the sequence flanked by the at least two recombinase recognition sites.

The recombinase can be introduced into a cell to exert its activity. It is also possible to use an existing recombinase in the cell. In any case, preferably the recombinase is inducible and can thus be activated by induction. Inducible recombinases are known in the art. E.g. an inducible promoter for the recombinase can be used.

The expression "recombinase recognition site" is also referred to as just "recombinase site" or recombinase target site or recombinase recognition targets. Example recombinases and sites are Flp (flippase), which binds to flippase recognition target (frt) sites. Preferred sites are lox (Cre) and frt (Flp). A preferred lox site is loxP that is derived from a bacteriophage P1 sequence. Other lox sites are e.g. lox 66 or lox 71.

According to the invention, a pair of recombinase recognition sites is used that are targeted by the same recombinase. They have the same orientation to allow a removal (also referred to as deletion) event in case or site directed recombination mediated by the recombinase that binds to these sites.

Other recombinase recognition sites for other recombinases might be provided on the construct for further purposes. In other embodiments, no other recombinase recognition sites except the pair for the inventive on-off or off-on method are provided on the construct, in total or within 20000 bp (base pairs) in length of the promoter and sgRNA sequences.

The invention can essentially be employed for switching sgRNA expression on or off. The differences between these two directions lie in the sequence that is flanked by recombinase recognition sites. In the "on" case, the flanked sequence is a transcription disruption sequence, which prevents expression of an active sgRNA ("off" state), and upon removal thereof, the active sgRNA is expressed ("on" state). In the "off" case, the flanked sequence is part of the promoter-sgRNA sequences. Initially the sgRNA is expressed ("on" state). The presence of the recombinase recognition sites does not prevent this. Upon recombinase mediated excision, a required portion of the construct is removed, which reduces or eliminates expression of an active sgRNA ("off" state).

E.g. of the "on" switch, the invention provides an expression cassette for expression of an sgRNA of the CRISPR/Cas9 system upon recombinase mediated activation, said cassette comprises a promoter, an sgRNA sequence, and a transcription disruption sequence flanked by at least a pair of recombinase recognition sites (e.g. with the same 5'-3' orientation), wherein said flanked transcription disruption sequence interrupts the sgRNA sequence or the promoter or both. "Interrupting" means that the presence of the transcription disruption sequence disturbs expression of an active sgRNA, either by preventing promoter action on the sgRNA sequence and/or by modifying the sgRNA sequence so that it is no longer active.

E.g. for the "off" switch, the invention provides an expression cassette for expression of an sgRNA of the CRISPR/Cas9 system until recombinase mediated inactivation, said cassette comprises a promoter, an sgRNA sequence that contains a DNA guiding sequence, and at least a pair of recombinase recognition sites, wherein said recombination sites are in the same orientation and flank either at least a part of the promoter upstream of the DNA guiding sequence or a at least a part of the sgRNA sequence downstream of the DNA guiding sequence.

"Active" sgRNA as used herein refers to an sgRNA that binds to a Cas9 protein and is capable of mediating a modification of a target DNA after hybridization with the DNA binding element (guide RNA or crRNA part) of the sgRNA within a CRISPR complex with Cas9. Example test systems are provided in any one of the examples described herein. For example, a reporter protein, like any fluorescent protein such as GFP or EGFP, can be targeted, i.e. its gene contains a target DNA. A reporter protein creates a detectable signal, preferably it is also a quantifiable signal.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence. To test whether a pair of polynucleotides hybridizes specifically in a cell environment, stringent hybridization conditions may be used.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.. Preferably the complementarity between two polynucleotides is at least 80% or at least 90% or at least 95% or even 100% in a sequence portion of at least the length of the entire hybridizing sequence, e.g. 8 to 40 nt for the DNA guiding element with the protospacer/DNA target. In case of a stem-loop of the sgRNA, the stem has preferably a complementary of about 60% to 100% or 70% to 90% or about 80%. Less than 100% complementary may be preferred in long stems to avoid too stable structures that may hinder a RNA polymerase and lead to transcription termination. Terminators are e.g. described in WO2012/164100.

The invention also provides the use of any of the inventive constructs in an expression system, e.g. a cell or artificial in vitro expression system, in a method of expressing the sgRNA in order to obtain an active sgRNA at a time of interest. It may also be used in vivo, preferably in a non-human model organism. The cell may be in an organism or in vitro, e.g. in a cell culture.

E.g. provided is a method of expressing an sgRNA of the CRISPR/Cas9 system upon recombinase stimulation (on switch), comprising
  A) providing a cell with an expression cassette comprising a promoter and an sgRNA sequence, wherein said sgRNA is interrupted by a transcription disruption sequence flanked by at least a pair of recombinase recognition sites (preferably with the same 5'-3' orientation);
  B) introducing or activating a recombinase in the cell, thereby removing the transcription disruption sequence,
  C) cultivating the cell under conditions allowing expression of the sgRNA sequence.

Also provided is a method of expressing an sgRNA of the CRISPR/Cas9 system until recombinase stimulation (off switch), comprising
  A) providing a cell with an expression cassette comprising a promoter, an sgRNA sequence that contains a DNA guiding sequence, and at least a pair of recombination recognition sites, wherein said recombination recognition sites (are in the same orientation and) flank either at least a part of the promoter upstream of the DNA guiding sequence or a at least a part of the sgRNA sequence downstream of the DNA guiding sequence or both (i.e. flank the joining or intermediate region with parts of both, the promoter and the sgRNA);
  B) cultivating the cell under conditions allowing expression of the sgRNA sequence.
  C) introducing or activating a recombinase in the cell, thereby deleting the sequence flanked by the recombination recognition sites.

Of course all details described above and below for the construct can also be included in the inventive methods, alone or in combination with each other.

Alternatively described, the invention can also be defined as a method for conditionally modifying a target DNA comprising the step of providing a cell with an expression construct comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first site-specific recombinase site is located between the promoter and the loop of the Cas9 binding element of said single guide RNA coding element, and a second of said site-specific recombinase recognition sites is located either upstream or downstream of said first site-specific recombinase site:
  A) wherein the construct is prevented from expressing the sgRNA in a cell by placement of a transcription disruption sequence that disrupts expression of the sgRNA, between said site-specific recombinase recognition sites, said transcription disruption sequence is excised upon recombinase mediated recombination at the recombinase recognition sites, thereby allowing recombinase dependent conditional expression of the sgRNA; or
  B) wherein the construct allows expressing the sgRNA by lack of a disrupting element between the site-specific recombinase recognition sites, said expression is conditionally prevented upon contacting the construct with a recombinase, whereupon recombinase mediated recombination of the recombinase recognition sites excises a nucleic acid portion required for transcription of the sgRNA, said nucleic acid portion being selected from at least a part of the promotor or at least a part of the sgRNA sequence or both;
  wherein in allowed expression configuration according to either A) or B) the single guide RNA is expressed and forms a complex with a Cas9 protein and said complex modifies the target DNA at a sequence site hybridizing to the DNA guiding element.

Figure 5A:
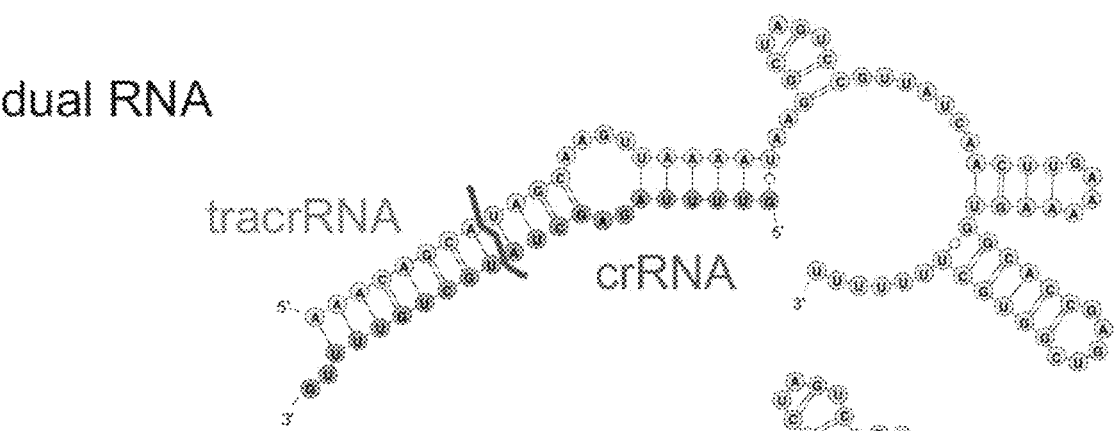
Figure 5A:
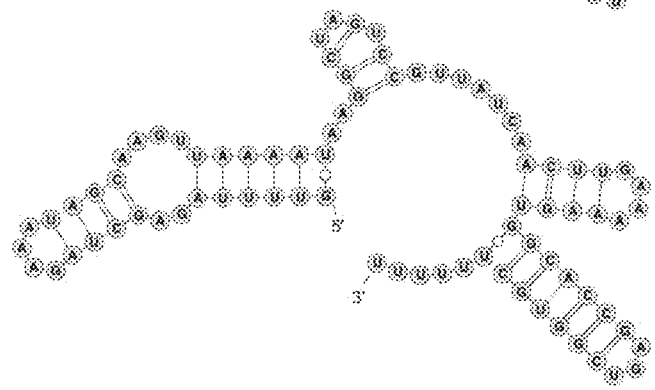
Figure 5A:
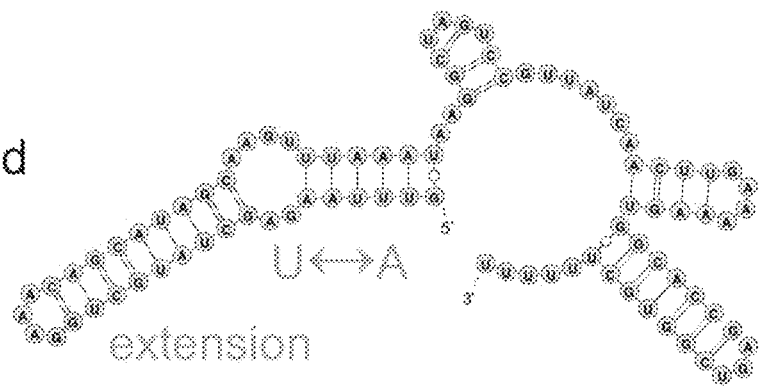
Figure 5A:
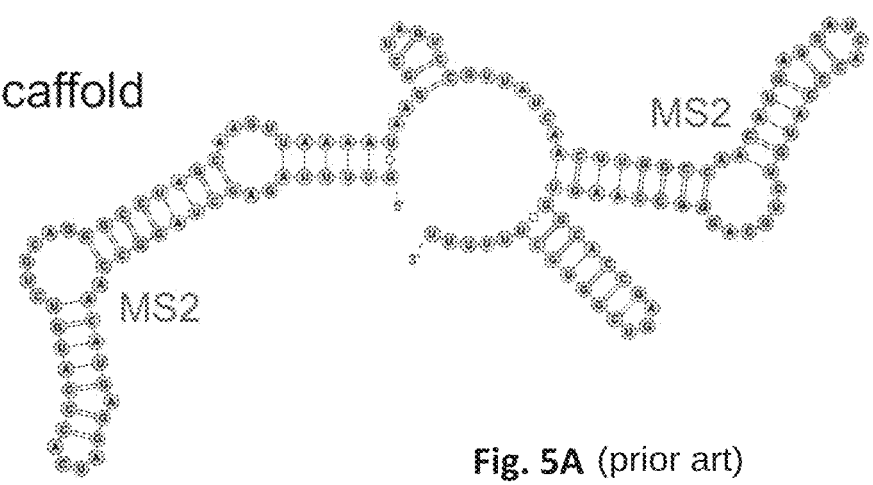
Figure 5B:
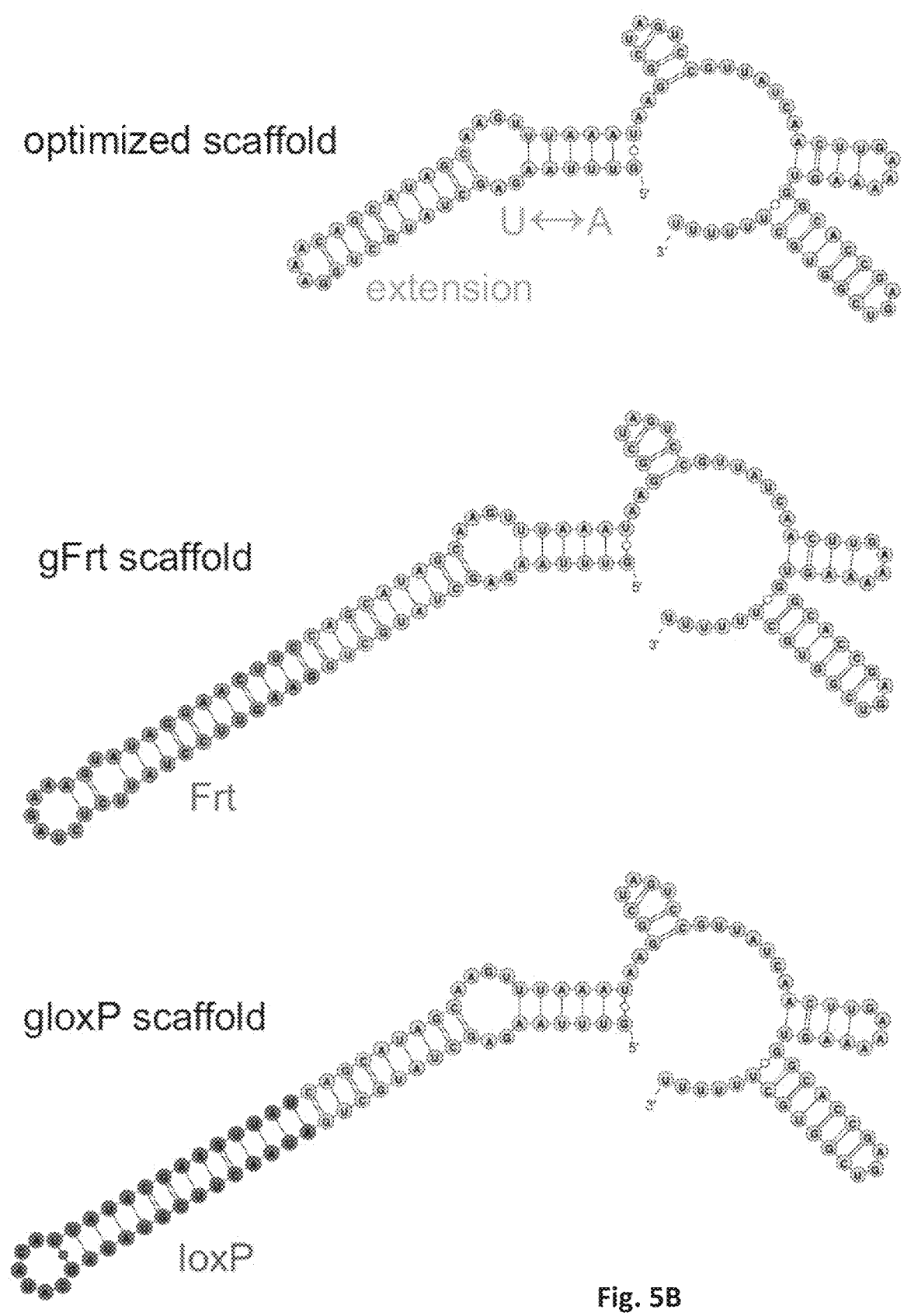

At least a first site-specific recombinase site is located between the promoter and a loop of the Cas9 binding element. "Between the promoter and the loop" means that the site is located in between any nucleotide of the promoter and any nucleotide of the loop. The site can overlap with the promoter and the loop. In fact, a most preferred location is in the loop, which can extend the stem of the Cas9 binding element by the sequence of the site, which preferably contains a palindromic sequence that may form a stem loop or any other self-hybridizing structure on its own. Also possible is a location in the promoter. The promoter or parts of the promoter can be interrupted by a transcription terminator (off-state) that may be flanked by recombinase recognition sites. Upon excision of the interruption by recombinase action, the construct switches to the on-state. The loop of the Cas9 binding element can be any loop involved in binding Cas9. Preferably is the loop that joins the crRNA sequence (DNA guiding sequence) with the tracrRNA sequence, which is usually, but not necessarily, the loop of the first stem-loop of the sgRNA. Other loops may be a loop of the second or third stem-loop of the sgRNA (compare FIG. 5A and 5B).

As said, each construct or method description also relate to each other, including their preferred embodiments. Accordingly, the construct suitable for the above method can also be described as a construct for conditionally modifying a target DNA in a Cas9 complex, comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first site-specific recombinase recognition site is located between the promoter and the loop of the Cas9 binding element of said single guide RNA sequence, and a second of said site-specific recombinase recognition sites is located either upstream or downstream of said first site-specific recombinase site:
  A) wherein the construct is unsuitable for expressing the sgRNA sequence in a cell by a transcription disruption sequence between said site-specific recombinase recognition sites, which is excisable upon recombinase mediated recombination of the recombinase recognition sites, thereby allowing conditional expression of the sgRNA; or
  B) wherein the construct is suitable for expressing the sgRNA by lack of a transcription disruption sequence between the site-specific recombinase recognition sites, and said recombinase recognition sites flank a nucleic acid portion required for transcription of the single guide RNA, said nucleic acid portion being selected from at least a part of the promotor or at least a part of the coding element or both.

The invention uses a transcription disruption sequence in the off state according to the off-to-on systems. The transcription disruption sequence can e.g. contain a stopping sequence that inhibits further read-through of a polynucleotide polymerase. A stopping sequence may be poly(T), a terminator sequence or just any (e.g. "junk") DNA that inhibits through length (e.g. as described in WO2012/164100A2 and -A3 including cited references therein). It may also simply disturb the action of the promoter on the sgRNA sequence, e.g. by simply increasing the distance to a transcription start site or between promoter regulatory elements. Polynucleotide polymerase requires a promoter at a certain distance to the transcription start, here the start of the sgRNA sequence. This certain distance may not exceed a particular length determined by the polymerase of choice. Mechanistically, this is based on proper folding of the polynucleotide in complex with the polymerase or transcription factors which allows the polymerase to act and begin transcription at the transcription start. Promoters are usually 100 to 1000 base pairs long and upstream (5') of the transcribed sequence. Preferably, the transcription disruption sequence flanked by at least a pair of recombinase recognition sites is within 20 nt in length of the sgRNA start. Another good option for placement is in a loop region of the sgRNA sequence. Such a loop is preferably a crRNA-tracrRNA linker loop (a repeat:antirepeat stem loop) or the first following (3') structural loop after the crRNA-tracrRNA linker loop. Preferably, if placed in as structural loop excluding the crRNA-tracrRNA linker loop, such a structural loop is preferably involved in Cas9 binding. Thereby, at least half of the stem is prevented from expression and binding of the modified and hence inactivated sgRNA with Cas9 is inhibited. Such inhibition is strongest if placed in the crRNA-tracrRNA linker loop. In general, the flanked transcription disruption sequence can be downstream (3' direction) of the start of the sgRNA sequence. Preferably, it contains a transcription stop sequence, such as a poly(T), e.g. a poly $(T)_{5-30}$ sequence.

Also, the flanked transcription disruption sequence can be completely in the promoter and thus prevents promoter activity on the start of the sgRNA sequence. Preferably wherein the transcription disruption sequence has a length of at least 10 nt or at least 20 nt, preferably at least 30 nt or at least 40 nt. Such distances can hinder a polymerase complex formation and stop action of the polymerase on the transcription start.

In the "on" state of the on-to-off embodiments, the sequence flanked by the recombination recognition sites is actively involved in expression of the sgRNA. This flanked sequence may again be a part of the promoter (or the entire promoter), by which removal the sgRNA transcription is prevented, or in the sgRNA, thereby modifying the sgRNA upon recombinase action so as to prevent its activity as described above in the Cas9 complex, e.g. prevent complex formation or its binding to the DNA target or modification activity, e.g. regulation or nuclease activity, on the proper DNA target.

The sequence flanked by the recombination recognition sites is preferably a promoter sequence required for promoter activity. It can also include the transcription start of the sgRNA sequence—with or without further promoter sequence being included. E.g. a possible flanked sequence comprises part of the promoter+start or start+the DNA guiding sequence of the sgRNA. Preferably the flanked sequence contains at least a part of the promoter region, such as a TATA box and/or a Proximal Sequence Element (PSE). Promoter as used herein includes all sequences that are necessary for transcription. The may not be transcribed themselves. Such a promoter may include a core promoter region and associated sequences such as a TATA box and/or a PSE. Suitable position of promoters and associated elements like TATA and PSE are known and e.g. disclosed in Lescure et al. *Nucl. Acids Res.* (1991) 19 (3): 435-441.

Preferably, the sequence flanked by the recombination recognition sites includes a part of a loop of the sgRNA (preferably, but not necessarily, of the crRNA:tracrRNA stem loop, e.g. one of the recombination recognition sites is placed in that loop) and a region downstream (3' direction) from said loop of the sgRNA, preferably wherein said downstream region comprises at least a portion of 10, or 20 nt in length of said sgRNA and/or the stem portion of said loop, which is preferably the crRNA: tracrRNA linker loop, with the stem portion being its antirepeat. The sequence flanked by the recombination recognition sites may be from the loop to the end of the sgRNA sequence, or to any other position, preferably with in the optional 3' portion (iv) described above, especially any of the structural loops therein, which are excellent positions to place on of the recombination recognition sites.

In "on" configuration, i.e. when expression is allowed, in both on-to-off or off-to-on variants, preferably the expressed single guide RNA forms a complex with a Cas9 protein. The Cas9 protein can be endogenous or exogenous to a cell in which the sgRNA is expressed. Preferably the Cas9/sgRNA reaction with the target DNA is in a cell, preferably an isolated cell. An isolated cell may be individualized cell or a cell in an aggregation, preferably outside of an organism. An isolated cell may be in an artificial container such as a petri-dish, a flask, a vial or well.

CRISPR, Cas proteins, especially proteins like Cas9, and suitable guide RNA sequences are disclosed, among others, in WO2013/176772, WO2010/054154, WO2012/054726, WO2014/144155, WO2015/071474, WO2015/006747, WO2009/115861, WO2015021426, WO2014/089290 (all incorporated herein by reference). As used herein "Cas9" or "Cas9 protein" refers to any Cas9 protein from any organism or modifications thereof that maintain Cas9 functionality, i.e. the binding of sgRNA to form a CRISPR complex capable of modifying a target DNA depending on the DNA targeting sequence of the sgRNA. It can be any enzyme of a class 2 CRISPR/Cas system with this function. Preferably, it may be any RNA-guided DNA nuclease suitable for the class 2 CRISPR/Cas system. Knowledge of Cas9 and suitable sgRNAs is extensive in the prior art and the present invention can rely on any known variant or combinations of variations, e.g. in fusion proteins. Particular reference is made to WO2013/176772 describing many Cas9 orthologues. Several thousand Cas9 proteins are known and their respective sequences have been deposited in sequence databases, like UniProtKB. These sequences may have been deposited under older designations of Cas9, like Csn1 or Csx12. Also included are functional equivalents of Cas9 having the RNA-guided DNA nuclease activity like Cpf1 (Zhang et al., Cell 2015, 163: 759-771). Representative Cas9 sequences are from Streptococcus thermophilus (UniProtKB number Q03J16; "StCas9"), S. pyogenes (UniProtKB number Q99ZW2; "SpCas9") and N. meningitidis ("NmCas9", Hou et al., PNAS 2913, 110(39):15644-15649). Another preferred Cas9 protein is of Staphylococcus aureus Cas9 (SaCas9, Ran et al., Nature 2015, 520:186). Cas9 proteins may have the domain architecture with a central HNH endonuclease domain and a split RuvC/RNaseH domain. Cas9 proteins may share 4 key motifs with a conserved architecture. Motifs 1, 2, and 4 are RuvC like motifs while motif 3 is an HNH-motif. Preferably the inventive Cas9 protein has 4 motifs, each of motifs 1-4 having at least about 75%, at least about 80%, at least about 85%, at least about 90%, at least about 95%, at least about 99% or 100% amino acid sequence identity to the motif s 1-4 of the Cas9 amino acid sequence depicted in FIG. 3A of WO2013/176772 (SEQ ID NOs:260-263 of WO2013/176772). Also, a Cas9 protein may comprise an amino acid sequence having at least about 75%, at least about 80%, at least about 85%, at least about 90%, at least about 95%, at least about 99% or 100% amino acid sequence identity to amino acids 7-166 or 731-1003 of the Cas9 amino acid sequence depicted in FIG. 3 of WO2013/176772 or to the corresponding portions in any of the amino acid sequences of SEQ ID NOs: 1-256 and 795-1346 of WO2013/176772. The phylogenetic tree of various Cas9 proteins is shown in FIG. 32A of WO2013/176772, all of which can be used according to the invention.

Cas9 can be modified, e.g. for codon optimization for increased efficiency of translation as compared to a non-optimized Cas9 sequence, by humanization (e.g. hspCas9) and/or to modify its activity (e.g. dCas9, nickase, Cas9n, such as spCas9n or hspCas9n; see WO2014/093595). Further Cas9 nickases and uses, e.g. for chimeric RNA, including for single and double nicking, are disclosed in WO2016/028682 and can be used according to the invention likewise. The Cas9 protein may have one or at least two nuclease domains. In other embodiment, no nuclease domain is present or it is inactivated. Removed or inactivated nuclease domains ("dCas9") allow other modifications than cutting of a target DNA, such as labelling (Deng et al., PNAS 2015, 112(38): 11870-11875; Chen et al. Methods in Enzymology, 2014, 546:337; Anton et al., Nucleus 2014, 5(2):163-172). dCas9 is still capable of forming RNA-guided DNA-binding complexes. A preferred dCas9 modification is one or more substitutions corresponding to D10A and/or H840A of Streptococcus pyogenes Cas9 (Jinek wt al., Science 2012 337: 816; Konermann et al., Nature 2015, 517:583). Labelling is e.g. with a fluorescent label. A preferred Cas9 variant for labelling is a fusion protein of Cas9 with a fluorescent protein (dCas9-FP). Any other binding partner can be used for a fusion protein. Further uses for Cas9, especially dCas9, include the regulation of transcription, including suppression of transcription or interference (Gilbert et al., Cell 2013, 154: 442-451; Qi et al., Cell 2013, 152: 1173-1183) or activation or increase of transcription. Suppression of transcription and activation or increase in transcription are referred together herein as alteration of transcription, which are forms of modification of the target DNA without necessarily cutting it. According to this embodiment of the invention, modifying a target DNA comprises binding of the Cas9 protein to the target DNA in dependence of the sgRNA without cutting the target DNA, preferably wherein binding of Cas9 protein, e.g. Cas9 protein fusions to transcriptional activators or suppressors, to the target DNA alters transcription of the target DNA. Another variant of CRISPR/Cas9 editing tool that can be used according to the invention is an RNA targeting CRISPR-associated (Cas) protein similar in function to Cas9, such as C2c2 (East-Seletsky, 2016). Such Cas protein is an RNA-guided RNA-cutting or targeting enzyme. In this case the inventive "DNA guiding sequence" also applies to RNA targeting and may be considered a RNA guiding sequence. The general increase understanding the term "DNA guiding sequence" is adhered to herein even though it may also refer to RNA guiding sequences—in case of adequate Cas9 or other CRISPR-associated protein combinations.

Preferred variants of Cas9 are suitable (i) for cleavage of only the (+) strand of the target DNA (e.g. Cas9 without HNH activity), (ii) cleavage of only the (−) strand of the target DNA (e.g. Cas9 without RuvC activity), (iii) cleavage of both strands of the target DNA (e.g. Cas9 with both HNH and RuvC activity) or transcriptional control of the target DNA (e.g. deactivated Cas9), which are disclosed in WO2016/033298 and WO2016/033246, incorporated herein by reference.

Further possible modifications of Cas9 include conjugations, especially fusions, with activators or repressors of transcription, a nuclear localization sequence and/or a chromatin modifier domain, such as KRAB domain of Kox1, the CS domain of HPlalpha or the WRPW domain of Hes1, suitable to recruit chromatin-modifying complexes to improve silencing of transcription. Activators of transcription are e.g. conjugations or fusions with transcriptional activators like VP64, VP16, p65, Rta, VPR (VP64-p65-Rta), PUF, PUF-VP16, PUF-VP64, p300 Core HAT domain, an acetyltransferase, a transcription factor, enhancer or histone demethylase, preferably also in combination with a nuclear localization sequence (Konermann et al., Nature 2015, 517: 583; Mali et al., Nature Biotech 2013, 31(9): 833; Hilton et al., Nature Biotechnology 2015, 33(5):510; Perez-Pinera et al., Nature Methods 2013 10(10):973, Chavez et al., Nature Methods 2015, 12(4): 326; Kearns et al., *Nature methods* 2015, 12(5): 401; Chen et al., *Cell Research* (2016) doi: 10.1038/cr.2016.3). CRISPR based activation or transcriptional interference by using activating or interfering Cas9, especially dCas9, variants can be used according to the invention, wherein a given gene of choice can be activated or repressed in expression by employing a sgRNA which is hybridized to the gene by the DNA guiding sequence (Du et al. 2016, Cold Spring Harb Protoc; doi:10.1101/pdb.top086835; Dominguez et al., *Nature Reviews* 2015, doi:10.1038/nrm.2015.2).

Cas9 may further be used to target any other protein or compound to a specific sgRNA guided location on a DNA molecule, such as other nucleases than Cas9, like a FokI nuclease (Tsai et al., *Nature Biotech*, 2014, 32(6):569, Guilinger et al., *Nature Biotech* 2014, 32(6):577). Such targeting is preferably achieved by providing a Cas9 fusion protein or conjugate with said other protein or compound.

Variations of Cas9 can induce dimerization change the PAM specific (see below) of modify, especially reduce off-target effects. Such a modification is e.g. the D1135E variant of SpCas9, a mutation that can be incorporated in any Cas9 as taught in the previously cited references such as WO2013/176772), the high-fidelity modification, HF1 of Cas9 (Kleinstiver et al., *Nature* 2016, doi:10.1038/nature16526). Preferred modifications are amino acid substitutions that correspond to any one of N497A, R661A, Q695A, Q926A of the SpCas9 or a combination thereof, preferably the combinations R661A/Q695A/Q926A or N497A/R661A/Q695A/Q926A ("SpCas9-HF1", Kleinstiver et al., supra).

Another variation of Cas9 that can be used according to the invention is the split expression of C-terminal and N-terminal fragments of Cas9 (N-Cas9 and C-Cas9 respectively) to achieve additional inducibility (Zetsche et al., *Nature Biotech* 2015, 33(2): 139-142), such as intein-mediated complex formation of the fragments by expression of N-/C-Cas9 fragment-split-intein fusion proteins that can be reconstituted to full-length Cas9 by intein-splicing (Truong et al., *Nucleic Acids Research,* 2015, 43(13): 6450). E.g., as described by Tuong et al., N-intein is fused with a N-terminal fragment of Cas9 (e.g. SpCas9$^{1-573}$) and C-intein is fused with a C-terminal fragment of Cas9 (e.g. SpCas9$^{574-1368}$). Any split site in the Cas9 sequence to fragment Cas9 can be used, as explained by Wright et al. (*PNAS* 2015, 112(10): 2984-2989). The Cas9 fragments can aggregate together with the sgRNA to form a functional DNA binding CRISPR-Cas complex. Any of these fragments can be controlled by the inventive recombinase system as a Cas9 protein.

Also possible is a photoactivatable Cas9 (Nihongaki et al., *Nature,* 2015, 33(7): 755-760). The inventive method would then also comprise the step of photoactivating Cas9 during an "on"-configuration phase.

Further, rational design of Cas9 variants to improve specificity is possible (Slaymaker et al., *Science* 2016, 351(5268): 84-88; Briner et al., *Molecular Cell* 2014, 56: 333-339). Rational design can be based on Cas9 crystal structures, which identified all functional molecular mechanism (Nishimasu et al., *Cell* 2014, 156: 935-949).

Any one of these proteins or suitable sgRNA sequence portions can be used according to the invention. There is high variability among Cas9, guide RNA structure and PAM sequences with functional exchangeability among guide RNA and Cas9 orthologs (Chylinski et al., *Nucleic Acids Research,* 2014, 42(10): 6091-6105; Fonfara et al., *Nucleic Acids Research,* 2014, 42(4): 2577-2590). Any of the naturally occurring Cas9 variants and orthologues can be used (e.g. shown in Chylinski et al., 2013, RNA Biology 10:5, 726-737) and any modification, including chimeric, humanized and fusion proteins. CRISPR associated proteins, or the guide RNA can be modified to alter their function. Such modifications are known from WO2014/197748, WO2015/089473 or Chen et al. (2013), all incorporated herein by reference. Especially preferred is the Chen modification, which replaces an U(T) to an A approximately 3, 4, 5, 6, 7, 8, nt after the DNA guiding sequence (also called target base pairing region) and/or the increase in length of the stem of the crRNA:tracrRNA stem-loop by e.g. 1, 2, 3, 4, 5, 6, 7, 8, 9, 10 bp in the stem. sgRNA can also be elongated at the ends or by insertions to contain diverse nucleic-acid elements, like protein-binding cassettes, artificial aptamers, pools of random sequences and natural long noncoding RNAs (Shechner et al., *Nature Methods* 2015, 12(7): 664). Further motifs, truncations and mutations of the sgRNA or its tracrRNA portion were investigated by Xu et al. (*Cell. Mol. Life Sci.* (2015) 72:383-399). Any such modification can be used according to the invention.

Another option to modify CRSIPR/Cas9 activity, similar to fusion proteins, is the use of RNA binding elements, that bind to the sgRNA at least when the sgRNA is bound by Cas9 and said RNA binding element comprises or is conjugated to another effector substance, like activators or repressors of transcription (Zalatan et al., *Cell* 2015, 160, 339-350). Any of the above binding partner for fusion proteins of Cas9 can be used for such a method as well as any Cas9 variant, e.g. dCas9.

Preferably, the complex comprising Cas9 and the active sgRNA modifies, preferably cuts, a target DNA at a site hybridizing to the DNA guiding element (called protospacer). Site-specific cleavage via CRISPR occurs at locations determined by base-pairing complementary between the DNA guiding sequence or element (which corresponds to a region found in crRNA in natural systems) and the target protospacer DNA and a short motif called protospacer adjacent motif (PAM). PAM is usually the sequence NGG, but PAM variants exist targeted by Cas9 protein variants. Commonly used Cas9 protein of *Streptococcus pyogenes* (SpCas9) recognizes a 5'-NGG trinucleotide, while Cas9 of other bacteria, like Staphylococcus aureus (SaCas9) or Neisseria meningitidis (NmCas9) bind to 5'-NNGRRT or 5'-NNNNGATT, respectively. Cas9 proteins derived from *Streptococcus* thermophilus (StCas9), St1Cas9 and St3Cas9, require 5'-NNAGAAW or 5'-NGGNG PAMs. (Müller et al., *Mol. Ther.* 2015, doi:10.1038/mt.2015.218; Esvelt et al., *Nature Methods,* 2013, 10(11):1116; Steinert et al., *The Plant Journal* 2015, 84: 1295-1305). Example PAM sequences or complementary sequences are ACA (WO2015/071474), GGG or CCG (Chen et al. (2013), GCC, CCC or CCA (Jinek et al. (2012), complementary strand sequences). Further PAM sequences are provided in Table 3 of WO2016/033298 (incorporated herein by reference). PAM sequences may vary depending on the used Cas9 species or artificially introduced Cas9 mutations (Esvelt et al., *Nature Methods* 2013, 10(11): 1116; Kleinstiver et al., *Nature* 2015, 523: 481; Kleinstiver et al. *Nature Biotech* 2015, 33(12):1293). The non-complementary DNA is usually cleaved at one or more sites three to eight bases upstream of PAM (downstream of PAM on the complementary strand, within the protospacer region). Cas9 and variants can be used that cleave the non-complementary strand, the complementary strand or both. Creating double strand breaks are preferred embodiments of the invention.

As said above, the invention can be used for homologous recombination. A DNA molecule can be provided that hybridizes with the modified, preferably cut, target DNA and undergoes homologous recombination with it. Homologous recombination is a type of genetic recombination in which nucleotide sequences are exchanged between two similar or identical molecules of DNA. It is most widely used by cells to accurately repair harmful breaks that occur on both strands of DNA, double-strand breaks. It usually involves, possibly with some variation the steps of modifying sections of DNA around the 5' ends of the break in a process called resection. In the strand invasion step that follows, an overhanging 3' end of the broken DNA molecule then "invades" a similar or identical DNA molecule that is not broken. After strand invasion, the further sequence of events may follow either of two main pathways discussed below (see Models); the DSBR (double-strand break repair) pathway or the SDSA (synthesis-dependent strand annealing) pathway. Homologous recombination that occurs during DNA repair tends to result in non-crossover products, in effect restoring the damaged DNA molecule as it existed before the double-strand break. According to the invention, preferably the cut target DNA is modified by a DNA molecule which contains a modification to the original target DNA, thereby introducing a modification. Such modifications can be used to alter function of a gene containing the target DNA. Methods of modifying the genome via CRISPR in a mammalian oocyte are disclosed in WO2014/131833 or in a stem cell or zygote in WO2014/172470. All these methods can be used with the active sgRNA expressed by the invention. Use of CRISPR in eukaryotes is further disclosed in WO2014/093595 and its above mentioned family members, Cong et al. 2013; WO2015/100929; WO2014/089290; and all above disclosures relating to therapeutic uses; WO2015/088643. CRISPR in plants is disclosed in WO2014/144155, WO2015/048707, WO2015/131101, WO2014/194190. Further methods include CRISPR in algae (WO2015/086795), CRISPR in prokaryotes (WO2010/075424, WO2012/164565), CRISPR in fungi (WO2015/138855). Modifications have been shown in silkworm, cattle, Brassica oleracea, Anopheles gambiae, Aedes aegypti, medaka, liverwort, and wheat (reviewed in Chen et al. *GigaScience* 2014, 3:24). In any one of these organisms or cells of such organisms, the inventive Cas9/sgRNA can be used to induce DNA modification, including both by point mutating by faulty repair or by homologous recombination.

A construct expressing Cas9 and/or the inventive conditional sgRNA expression construct can be introduced into a cell with a vector or delivery system. Delivery and vector systems are described in WO2015/089419, WO2015/089462, WO2015/088643 (large targeting vector), WO2015/191693. A delivery device for microorganisms and a CRISPR/Cas9 system for targeting antibiotic resistance genes are disclosed in WO2015/159068. Advantageous vectors include lentiviruses and adeno-associated viruses, and types of such vectors can also be selected for targeting particular types of cells. Preferred are non-viral delivery vehicles, such as encapsulations, liposomes, nanoparticles and polymerosomes (WO2015/191693). The vector may be a polynucleotide comprising the construct. By introduction into the cell, the vector may be expended. Therefore the invention also comprises a cell, especially eukaryotic cell, such as an human or non-human animal cell, mammalian cell, a plant cell, an avian cell, a reptile cell or a fungal cell, especially a yeast cell, comprising the inventive construct. Any method oy the invention can be performed in these cells.

Preferably, at least one required component of the CRISPR/Cas9 system, in particular Cas9 or the sgRNA is inactivated after a period of activity, such as after 1 h, 2 h or 1 day or later. Inactivation is preferably by self-inactivation. Self-inactivating CRISPR/Cas9 systems are disclosed in WO2015/089351.

Homologous recombination can be used to repair a defective gene in said cell, e.g. by replacement of the target DNA by a functional version to restore function to said gene. The functional version can be a wild-type version. Homologous recombination, especially for gene repair, is disclosed e.g. in WO2014/143381, and any of the above and below references on basic and therapeutic disclosures. The invention also provides a method for somatic gene therapy or gene modification, wherein said defective gene that is repaired or has its target DNA replaced is in a cell of an organism, especially a somatic cell (Savic et al., *Translational Research* 2016, 168: 15-21) or stem cell, e.g. a pluripotent stem cell (Hendriks et al., *Cell Stem Cell* 2016 18: 53). Technically feasible is also repair or modification in a germ cell. Preferably, the germ cell is of a plant or of a non-human animal.

CRISPR/Cas9 based genome editing has been described for various therapeutic uses, e.g. the treatment of Leber's congenital amaurosis (WO2015/138510), usher syndrome and retinitis pigmentosa (WO2015/134812), Huntington disease (WO2015/070212, WO2016/020399), HIV (WO2014/165349, WO2015/031775, WO2015/148670), Alzheimer's Disease (WO2015/168800), cancer (WO2015/161276), breast cancer (WO2016/026444), cystic fibrosis (WO2015/157070), muscular dystrophy (WO2016/025469), beta-thalassemia (WO2015/148860), sickle cell disease (WO2015/148863), primary open angle glaucoma (WO2015/153780), hemoglobinopathies (WO2013/126794), channelopathies (WO2015/153760), HSV-1 (WO2015/153789), HSV-2 (WO2015/153791) or HBV and other viral diseases (WO2015/089465), in nucleotide repeat disorders (WO2015/089351, WO2015/089354), of various diseases and conditions in WO2015/048577, engineering T cells for immunotherapy (WO2014/191128). Any of these therapeutic uses can be facilitated by the inventive sgRNA expression method.

Therefore, the invention also relates to the construct of the invention for use in a method of therapy as described herein or the use of said construct for the manufacture of a medicament for said method of therapy. A medicament may have a pharmaceutically acceptable carrier and/or delivery agent, such as a liposomal composition.

In a further preferred embodiments according to all aspects of the invention, at least two constructs with different or the same recombinase recognition sites and/or with different sgRNA sequences can be expressed. The at least two constructs can also be used to modify a target genome at different locations, depending on the sgRNA's DNA targeting sequences. Two or more sgRNA molecules can be produced according to the invention in one expression system (e.g. in vitro, a cell, etc.). Such more than one sgRNAs or constructs can be expressed from one or more than one polynucleotide, e.g. a vector or a modified genome. For example, WO2015/010114 discloses targeting multiple DNAs with at least two DNA targeting RNAs (crRNAs). A similar adaptation of the CRISPR/Cas9 system can be used according to the invention. Different recombinase systems as described above can be used to independently switch the expression of the constructs/sgRNAs. A Cas9 protein can be provided separately for both constructs, e.g. constitutively or under a separate regulation, or as part of a flanked sequences for excision upon recombinase action on one or more than one of these constructs.

Important aspects of the invention are uses of the inventive methods and constructs for screening purposes. Accordingly, the invention provides a screening method comprising introducing a plurality of constructs with different sgRNA into a plurality of expression systems, e.g. cells, wherein an expression system of interest is selected according to a property of interest. A DNA targeting sequence of an sgRNA (protospacer complementary) or a DNA target (protospacer) in a given expression system may be identified from said selected expression system, that may have a phenotype of interest. Konerman et al. (2015) describe a screening system to identify guide RNA sequences. Similar methods can be used according to the invention. However, the invention improves on such prior art methods since the inventive constructs can be used to modify expression during the life time of an expression system, in particular a cell. E.g. an sgRNA that may be lethal during a portion of the cells life cycle may be switched on during another part of its life cycle, wherein sgRNA activity may not be lethal anymore. Also activity during different stages of a cells life may be investigated. The same as said from cells applies to multicellular cell aggregates or organisms. Preferably, constructs are selected, in which the DNA targeting/guiding sequence remains in the construct after the switch for easier identification of the sgRNA target. Otherwise, the DNA target in the expression system itself must be identified, which may be more laborious. Such constructs are e.g. those with a flanked sequence (for both "on" and "off" variants) comprising at least parts of the promoter or within or after the tracrRNA:crRNA loop. Preferably, the inventive screening method is used to test mutations induced by the Cas9 mediated guided ds breaks. Such mutations may alter the function of a particular gene. A multitude of sgRNAs, e.g. at least 100 different, or 500 different or 1000 different or more sgRNA are introduced into the expression system and a reaction of the expression system is observed. The inventive screening method can also be used to test substances and their effects or environmental effects on mutations in the expression system, commonly cells. Such effects of mutations may be compared with the substance or environment effects without such a mutation, e.g. wild type expression system that was not subject to sgRNA mutation. For example, the inventive constructs and methods can be used to test a harmful compound and mutations that would alleviate said harmful effects. A cell having such an alleviating response will be selected and the mutation can be identified, practically by identifying the guide sequence of the sgRNA. Of course any other effect beside harmful reactions can be investigated as well. In general any loss or gain of function of any gene can be investigated during or without influence of screening substances/compounds or environmental effects.

One of the advantages of the inventive method controlling sgRNA in screening is that Cas9 expression may be kept constant. Inducible Cas9 systems have the drawback that Cas9 with or without sgRNA may have an effect on cell viability and this effect may mask any screening effect that relies on differential phenotype comparison of active Cas9 system (targeting a given DNA portion) next to a control system. sgRNA expression control by the inventive on-to-off or off-to-on systems avoids such drawbacks and allows a more sensitive observation and comparison of the screening object, i.e. cells.

Tight switch-off system for sgRNAs provides a possibility of temporal expression of sgRNA controlling the timing of genome editing and limiting the risk of off-targeting that obscures or falsifies results. It may also prevent harm to cells in case of unwanted reactions. In our system, the guide sequence of sgRNA is kept on the genome allowing subsequent identification in screening regimen. Tight induction or disruption of sgRNA expression in randomized library screens will allow for optimal screening regimen. In pool based screens, it allows for the ideal sample control. By quantifying representation of guides compared to non-induced control, relative enrichment subtracted by biases in the original cell population is achieved. Specific hits, e.g. identified by dropout in pool-based screens should be subtracted from lethal mutations as well as cellular background mutations resulting in dropout to generate a pure dataset. By tight inducibility of sgRNA expression, this can be achieved in systematic fashion. As an alternative to inducible Cas9 expression, the system can be used in already established Cas9 cell lines or primary cells derived from Cas9 expressing model organisms.

Preferably, especially preferred in the "or"—option B) as defined above, the nucleic acid portion flanked by recombinase recognition sites is either upstream or downstream of the DNA guiding element of the single guide RNA. This can maintain it in the construct/sgRNA for later identification during screening and identification processes.

In a further combinable aspect of the invention, the transcription disruption sequence contains a Cas9 sequence, thereby expressing the Cas9 sequence until the transcription disruption sequence is excised upon recombinase mediated recombination. This can be used to create limited activity of Cas9 protein at one time interval and of the sgRNA at another, usually overlapping, time interval. The overlap creates a short time span, wherein both Cas9 and the sgRNA are present in the expression system, e.g. cell, and act upon the sgRNA's target DNA. This is also referred to as "editing pulse" herein. Upon recombination, Cas9 expression is switched off and sgRNA—switched on. Only a short time window in which both components are present due to Cas9 mRNA and protein stability and rapid expression of sgRNA, allows for genome editing. Given the high activity of the guides fused to the scaffold structure presented herewith, this provides higher specificity of the system as off-targeting was shown to be associated with high and prolonged expression of Cas9 and sgRNA. Such an editing-pulse combines high specificity with superior efficiency.

The principle of temporal overlapping expression to regulate complex activity of the editing pulse can also be applied to all other complexes. The invention provides also a method of limiting activity of a complex by expressing at least two parts of said complex subsequently by expressing a construct encoding a first part of the complex and a second part of said complex, wherein said second part is disrupted by the first part flanked by site-specific recombinase recognition sites, whereby only the first part is expressed; excising the first part by recombinase mediated recombination of the recombinase recognition sites, thereby removing the disruption of the second part and allowing the second part to be expressed; allowing complex formation of the produced first part and second part to form a complex, preferably wherein said complex is a reaction complex or a binding complex or both. In the CRISPR/Cas9 system, the first and second parts are Cas9 protein and a single guide RNA with a Cas9 binding element. But of course any other complex members can be expressed in this way to limit activity to a time when both complex members are present. This can e.g. be advantageous when it is desired to remove a part of the complex from the cells. This should be the first part that is excised and removed from expression. Such a first part may e.g. be a harmful component to the cell.

For the CISPR embodiment, the invention provides a method of temporary limiting the activity of a Cas9-sgRNA complex comprising
  A) providing a cell with an expression construct comprising a promoter, an sgRNA sequence, wherein said sgRNA sequence is disrupted by a coding sequence of the Cas9 protein flanked by directly oriented recombinase recognition sites;
  B) culturing said cell under conditions suitable for the expression of the Cas9 protein,
  C) introducing or activating a recombinase in the cell, thereby removing the Cas9 sequence flanked by the recombination recognition sites and hence the disruption of the sgRNA sequence,
  D) culturing said cell under conditions suitable for the expression of the sgRNA, whereby said sgRNA forms a complex with the Cas9 protein formed in step B) and said complex potentially modifies a target DNA at a sequence site hybridizing to a DNA guiding element of the sgRNA.

sgRNA is expressed—as is common—by action of a promoter. Such a promoter may also be the target for excision by placing a recombinase site within or upstream (5') of it. For any embodiment of the invention, many possibilities for promoters exist. Preferably, the promoter is a polIII promoter, such as a U6, 7SK or H1 promoter. Preferably, the promoter comprises a TATA box and/or a PSE (Proximal Sequence Element). According to any embodiment of the invention, a TATA box may be placed inside or overlapping with a recombination recognition sites, especially a lox site.

The promoter can be a RNA Polymerase II (Pol II) or RNA Polymerase III (Pol III) promoter (see WO2015/099850). Preferably it is a Pol III promoter such as U6, 7SK or H1 promoter. Structures of Pol III promoters are disclosed in Ma et al. 2014. Use of a H1 promoter is e.g. shown in WO2015/195621 (incorporated herein by reference), which methods and construct designs can be used according to any aspect of the invention.

A Pol II promoter can be selected from the group consisting of retroviral Rous sarcoma virus (RSV) LTR promoter (optionally with the RSV enhancer), the cytomegalovirus (CMV) promoter (optionally with, the CMV enhancer), the SV40 promoter, the dihydro folate reductase promoter, the β-actin promoter, the phosphoglycerol kinase (PGK) promoter, the EFla promoter, and further any one of the CAG, EF1A, CAGGS, PGK, UbiC, CMV, B29, Desmin, Endoglin, FLT-1, GFPA, and SYN1 promoters. Pol II promoters can be used in combination with Csy4 cleavage sites flanking the guide RNA sequence as disclosed in WO2015/099850 or with a self-cleaving ribozyme. The use of pol II in guide expression is further described in WO2015/153940.

The result of the recombinase action leads to a modified sgRNA with altered Cas9 binding (either on to off, as described above). The unaltered or altered sgRNA can be subject to identification. A hallmark of the invention is that a recombinase recognition site remains in the sgRNA according to several embodiments of the invention. The invention provides a single guide RNA comprising a sequence of a recombinase site, preferably a loxP site or an FRT site. The recombinase site can be in any location as described above; preferably said recombinase recognition site is in a loop linking a stem of a Cas9 binding element and its complementary sequence (e.g. the repeat: antirepeat loop corresponding to those found in crRNA and tracrRNA). This sgRNA can be produced or be obtainable by a method of the invention. Furthermore, it can be used in the inventive screening method to identify a certain mutation via guide sequence identification. It can also be used to test a construct to identify if recombination has already occurred. Accordingly, this sgRNA can be used to monitor CRISPR or Cas9 activity.

In preferred embodiments of the invention, a marker gene with a promoter driving the marker expression is present in the sgRNA-coding sequence. Such a marker allows detection of cells encoding sgRNA. In a particular preferred embodiment, the marker gene is flanked by pair of recombinase recognition sites, such as the same pair of recombinase recognition sites that flanks the above described "flanked sequence", which may flank a transcription disruption sequence, such a transcription stop sequence. The marker may be a sequence that produces any kind of detectable signal. Preferably the marker is a cell selection marker, such as an antibiotic resistance gene, which allows selecting cells being resistant to an antibiotic for which the antibiotic resistance gene confers resistance. A preferred example of such a gene is PGK-blasticidin, but any expression marker or resistance gene (having a promoter and a coding sequence) is possible, in any orientation. In a preferred embodiment an antibiotic selection marker flanked by a pair of recombinase recognition sites is present within the sgRNA coding sequence disrupting transcription of sgRNA and allowing for strict selection of cells with intact transcription disruption cassette. Such an embodiment ensures tightness of the STOP cassette.

Preferably, the invention is defined according to the following embodiments:
  1. An expression cassette for expression of a single guide RNA (sgRNA) of a CRISPR/Cas9 system, said cassette comprises a promoter, an sgRNA sequence, and a sequence flanked by at least a pair of recombinase recognition sites, wherein recombinase activated recombination at the pair of recombinase recognition sites is capable of excising said flanked sequence, whereby either i) at least one of said recombinase recognition sites is located within the sgRNA sequence and said flanked sequence contains an transcription disruption sequence ("off-to-on switch") or ii) said flanked sequence is at least a part of the promoter or of the sgRNA sequence ("on-to-off switch").
  2. An expression cassette of 1 for expression of an sgRNA of the CRISPR/Cas9 system upon recombinase mediated activation, said cassette comprises a promoter, an sgRNA sequence, and a transcription disruption sequence flanked by at least a pair of recombinase recognition sites (with the same 5'-3' orientation), wherein said flanked transcription disruption sequence interrupts the sgRNA sequence or the promoter sequence.
  3. An expression cassette of 1 for expression of an sgRNA of the CRISPR/Cas9 system until recombinase mediated inactivation, said cassette comprises a promoter, an sgRNA sequence that contains a DNA guiding sequence, and at least a pair of recombination recognition sites, wherein said recombination sites are in the same orientation and flank either at least a part of the promoter upstream of the DNA guiding sequence or a at least a part of the sgRNA sequence downstream of the DNA guiding sequence.

4. Method of expressing an sgRNA of the CRISPR/Cas9 system upon recombinase stimulation, comprising
   A) providing a cell with an expression cassette comprising a promoter and an sgRNA sequence, wherein said sgRNA is interrupted by a transcription disruption sequence flanked by at least a pair of recombinase recognition sites (preferably with the same 5'-3' orientation);
   B) introducing or activating a recombinase in the cell, thereby removing the transcription disruption sequence,
   C) cultivating the cell under conditions allowing expression of the sgRNA sequence.
5. Method of expressing an sgRNA of the CRISPR/Cas9 system until recombinase stimulation, comprising
   A) providing a cell with an expression cassette comprising a promoter, an sgRNA sequence that contains a DNA guiding sequence, and at least a pair of recombination recognition sites, wherein said recombination recognition sites (are in the same orientation and) flank either at least a part of the promoter upstream of the DNA guiding sequence or a at least a part of the sgRNA sequence downstream of the DNA guiding sequence or both (i.e. flank the joining or intermediate region with parts of both, the promoter and the sgRNA);
   B) cultivating the cell under conditions allowing expression of the sgRNA sequence.
   C) introducing or activating a recombinase in the cell, thereby deleting the sequence flanked by the recombination recognition sites.
6. A method for conditionally modifying a target DNA comprising the step of
   providing a cell with an expression construct comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first site-specific recombinase site is located between the promoter and the loop of the Cas9 binding element of said single guide RNA coding element, and a second of said site-specific recombinase recognition sites is located either upstream or downstream of said first site-specific recombinase site:
   A) wherein the construct is prevented from expressing the sgRNA in a cell by placement of a transcription disruption sequence that disrupts expression of the sgRNA, between said site-specific recombinase recognition sites, said transcription disruption sequence is excised upon recombinase mediated recombination at the recombinase recognition sites, thereby allowing recombinase dependent conditional expression of the sgRNA; or
   B) wherein the construct allows expressing the sgRNA by lack of a disrupting element between the site-specific recombinase recognition sites, said expression is conditionally prevented upon contacting the construct with a recombinase, whereupon recombinase mediated recombination of the recombinase recognition sites excises a nucleic acid portion required for transcription of the sgRNA, said nucleic acid portion being selected from at least a part of the promotor or at least a part of the sgRNA sequence or both;

wherein in allowed expression configuration according to either A) or B) the single guide RNA is expressed and forms a complex with a Cas9 protein and said complex modifies the target DNA at a sequence site hybridizing to the DNA guiding element.
7. A construct for conditionally modifying a target DNA in a Cas9 complex, comprising i) a promoter for a RNA polymerase, ii) a single guide RNA (sgRNA) sequence with a DNA guiding element and one or more stem-loop(s) with a Cas9 binding element in a stem, and iii) a pair of site-specific recombinase recognition sites, wherein at least a first of said site-specific recombinase recognition sites is located between the promoter and the loop of the Cas9 binding element of said single guide RNA sequence, and a second of said site-specific recombinase recognition sites is located either upstream or downstream of said first site-specific recombinase site:
   A) wherein the construct is unsuitable for expressing the sgRNA sequence in a cell by a transcription disruption sequence between said site-specific recombinase recognition sites, which is excisable upon recombinase mediated recombination of the recombinase recognition sites, thereby allowing conditional expression of the sgRNA; or
   B) wherein the construct is suitable for expressing the sgRNA by lack of a transcription disruption sequence between the site-specific recombinase recognition sites, and said recombinase recognition sites flank a nucleic acid portion required for transcription of the single guide RNA, said nucleic acid portion being selected from at least a part of the promotor or at least a part of the coding element or both.
8. The construct on any one of 1, 2 or 7 or the method of any one of 4 or 6, wherein the transcription disruption sequence flanked by at least a pair of recombinase recognition sites is within 20 nt in length of the sgRNA start or is in a loop region of the sgRNA sequence, preferably a crRNA-tracrRNA linker loop (a repeat: antirepeat stem loop).
9. The construct on any one of 1, 2 or 7 or the method of any one of 4 or 6, wherein the transcription disruption sequence is completely in the promoter and prevents promoter activity on the start of the sgRNA sequence, preferably wherein the transcription disruption sequence has a length of at least 10 nt, preferably at least 20 nt.
10. The construct on any one of 1, 2, 7 or 8 or the method of any one of 4, 6 or 8, wherein the transcription disruption sequence is downstream (3' direction) of the start of the sgRNA sequence and contains a transcription stop sequence, such as a poly(T), e.g. a poly(T)$_{5-30}$ sequence.
11. The construct on any one of 1, 2, 7, 8 or 10 or the method of any one of 4, 6, 8 or 10, wherein the transcription disruption sequence is in a loop region of the sgRNA sequence, preferably a crRNA-tracrRNA linker loop.
12. The construct on any one of 1, 3 or 7 or the method of any one of 5 or 6, wherein the sequence flanked by the recombination recognition sites is a promoter sequence required for promoter activity.
13. The construct on any one of 1, 3 or 7 or the method of any one of 5 or 6, wherein the sequence flanked by the recombination recognition sites includes the transcription start of the sgRNA sequence, preferably wherein the flanked sequence includes at least a part of the promoter region, such as a TATA box and/or a Proximal Sequence Element (PSE).

14. The construct on any one of 1, 3 or 7 or the method of any one of 5 or 6, wherein the sequence flanked by the recombination recognition sites includes a loop of the sgRNA (preferably, but not necessarily, as defined in 8) and a region downstream (3' direction) from said loop of the sgRNA, preferably wherein said downstream region comprises at least a portion of 10, or 20 nt in length of said sgRNA and/or the stem portion of said loop, which is preferably the tracrRNA linker loop, with the stem portion being its antirepeat. The sequence flanked by the recombination recognition sites may be from the loop to the end of the sgRNA sequence.

15. Method according to any one of 4 to 6 and 8 to 14, wherein during allowed expression the expressed single guide RNA forms a complex with a Cas9 protein. The Cas9 protein can be endogenous or exogenous.

16. Method according to 15, wherein said complex modifies a target DNA at a site hybridizing to the DNA guiding element (called protospacer).

17. The method according to 6 or 16, wherein modifying a target DNA comprises cutting the target DNA.

18. The method according to claim 6 or 16 wherein modifying a target DNA comprises inserting a nucleic acid into the target DNA, deleting at least one nucleotide from the target DNA or methylation of at least one nucleotide from the target DNA.

19. The method according to 6 or 16, wherein modifying a target DNA comprises binding of the Cas9 protein to the target DNA in dependence of the sgRNA without cutting the target DNA, preferably wherein binding of Cas9 protein to the target DNA alters transcription of the target DNA, in particular preferred, wherein the Cas9 protein is a fusion protein with a non-Cas9 sequence, preferably with a transcription activator or suppressor or repressor.

20. The method according to 16, 17, 18 or 19, wherein a DNA molecule hybridizes with the modified, preferably cut, target DNA and undergoes homologous recombination.

21. The method of any one of 15 to 20, in a cell, wherein the cell can be an isolated cell.

22. The method of any one of 15 to 21 for gene repair in a cell or chromosome, wherein a defective gene in said cell is repaired by a functional version of said gene by said homologous recombination.

23. The method of 22 for somatic gene therapy, wherein said defective gene is in somatic cell of an organism.

24. The construct of any one of the preceding embodiments for use in a method of therapy according to 23 or use of said construct for the manufacture of such a medicament for said method of therapy.

25. The method of any one of 4 to 6 and 8 to 23, wherein at least two constructs with different or the same recombinase recognition sites and with different sgRNA sequences are expressed and preferably also used to modify a target genome at different locations, depending on the sgRNA's DNA targeting sequences.

26. The method of any one of 4 to 6, 8 to 23, and 24 for screening purposes, comprising introducing a plurality of constructs with different sgRNA into a plurality expression systems, preferably cells, wherein an expression system of interest is selected according to a property of interest and identifying a DNA targeting sequences of an sgRNA or a DNA target sequence of said selected cell.

27. The method or construct of any one of 6 to 26, wherein in "or"-option B) as defined in 6 or 7 the nucleic acid portion flanked by recombinase recognition sites is either upstream or downstream of the DNA guiding element of the single guide RNA. This can maintain it in the construct/sgRNA for later identification during screening and identification processes.

28. The method or construct of any one of 1, 2, 4, 6 to 27, wherein the transcription disruption sequence contains a Cas9 sequence, thereby expressing the Cas9 sequence until the transcription disruption sequence is excised upon recombinase mediated recombination.

29. A method of limiting activity of a complex by expressing at least two parts of said complex subsequently by expressing a construct encoding a first part of the complex and a second part of said complex, wherein said second part is disrupted by the first part flanked by site-specific recombinase recognition sites, whereby only the first part is expressed; excising the first part by recombinase mediated recombination of the recombinase recognition sites, thereby removing the disruption of the second part and allowing the second part to be expressed; allowing complex formation of the produced first part and second part to form a complex, preferably wherein said complex is a reaction complex or a binding complex or both.

30. The method of 29, wherein the first and second parts are Cas9 protein and a single guide RNA with a Cas9 binding element.

31. The method of 28 or 30 of temporary limiting the activity of a Cas9-sgRNA complex comprising
A) providing a cell with an expression construct comprising a promoter, an sgRNA sequence, wherein said sgRNA sequence is disrupted by a coding sequence of the Cas9 protein flanked by directly oriented recombinase recognition sites;
B) culturing said cell under conditions suitable for the expression of the Cas9 protein,
C) introducing or activating a recombinase in the cell, thereby removing the Cas9 sequence flanked by the recombination recognition sites and hence the disruption of the sgRNA sequence,
D) culturing said cell under conditions suitable for the expression of the sgRNA, whereby said sgRNA forms a complex with the Cas9 protein formed in step B) and said complex potentially modifies a target DNA at a sequence site hybridizing to a DNA guiding element of the sgRNA.

32. Construct or method of any one of 1 to 31, wherein the promoter is a polIII promoter, preferably selected from U6, 7SK or H1 promoters, especially preferred wherein the promoter comprises a TATA box and/or a PSE.

33. A single guide RNA comprising a sequence of a recombinase site, preferably a loxP site or a FRT site; preferably wherein said recombinase recognition site is in a loop linking a stem of a Cas9 binding element and its complementary (e.g. as in 8.). This sgRNA can be produced or be obtainable by a method of any one of 4 to 6 or 8 to 32.

34. Cassette, construct, method or sgRNA of any one of 1 to 33, wherein the recombinase recognition site is selected from frt or lox sequences, preferably loxP, lox 66 or lox 71 sequences.

35. Cassette, construct or method or sgRNA of any one of 1 to 34, comprising a marker gene and a promoter driving the marker gene expression that is flanked by a pair of recombinase recognition sites, preferably wherein the marker is an antibiotic resistance gene.

The present invention is further illustrated by the following figures and examples, without being limited to these embodiments of the invention.

FIGURES

FIG. 1. Switch-on and switch-off systems within U6 promoter. U6 promoter is shown in in box with PSE within. Recombination site is represented with a triangle. sgRNA is shown in thick black line with a +1 guanine (transcriptional start) indicated. Poly-T—transcriptional STOP signal. MCS—multiple cloning site.

Figure 2:
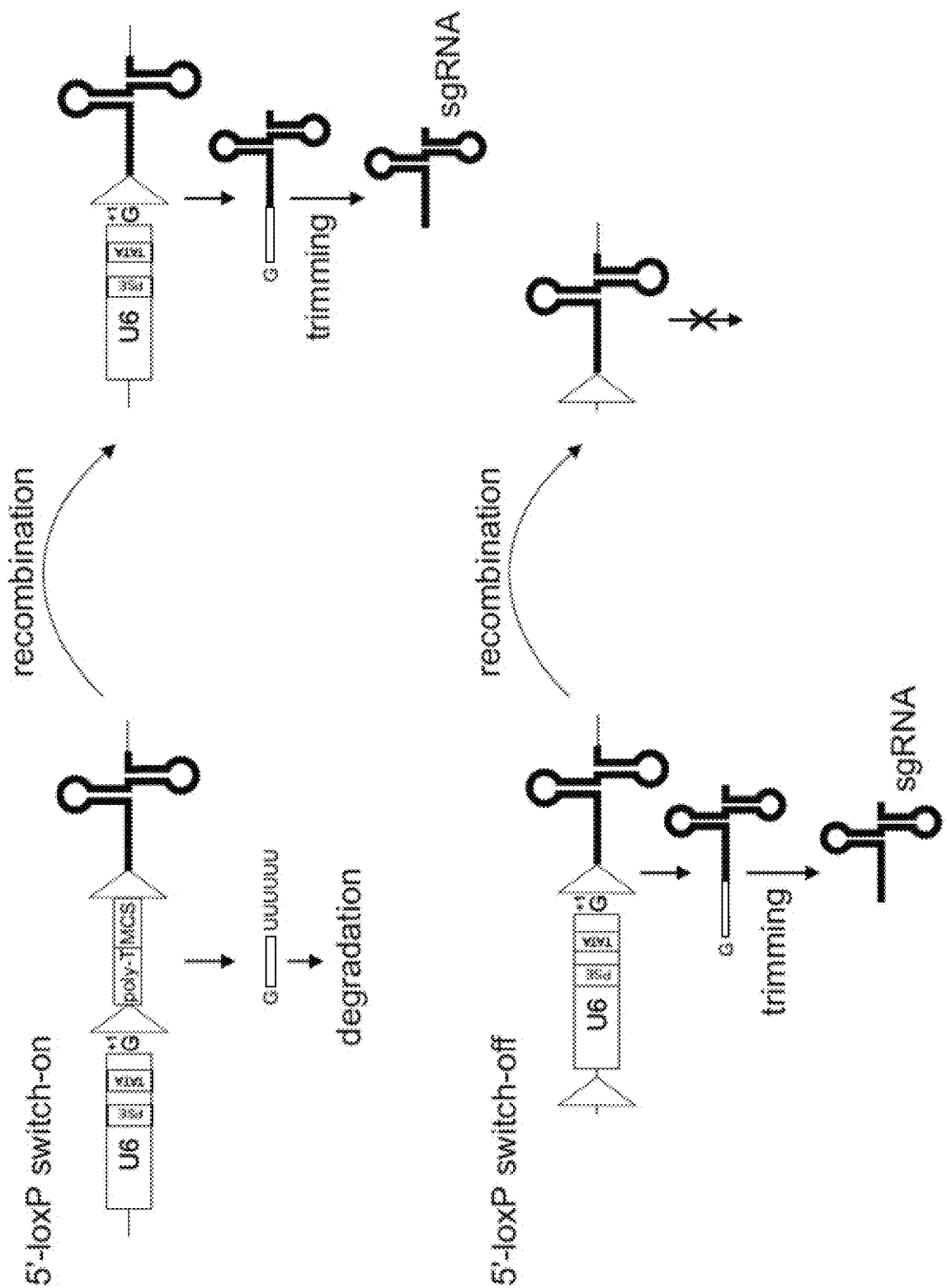

FIG. 2. Switch-on and switch-off systems with recombination site at the 5' start of sgRNA. Transcripts from recombination site will be either degraded as non-functional RNAs or trimmed off (white boxed line 5' part of transcript following G).

Figure 3:
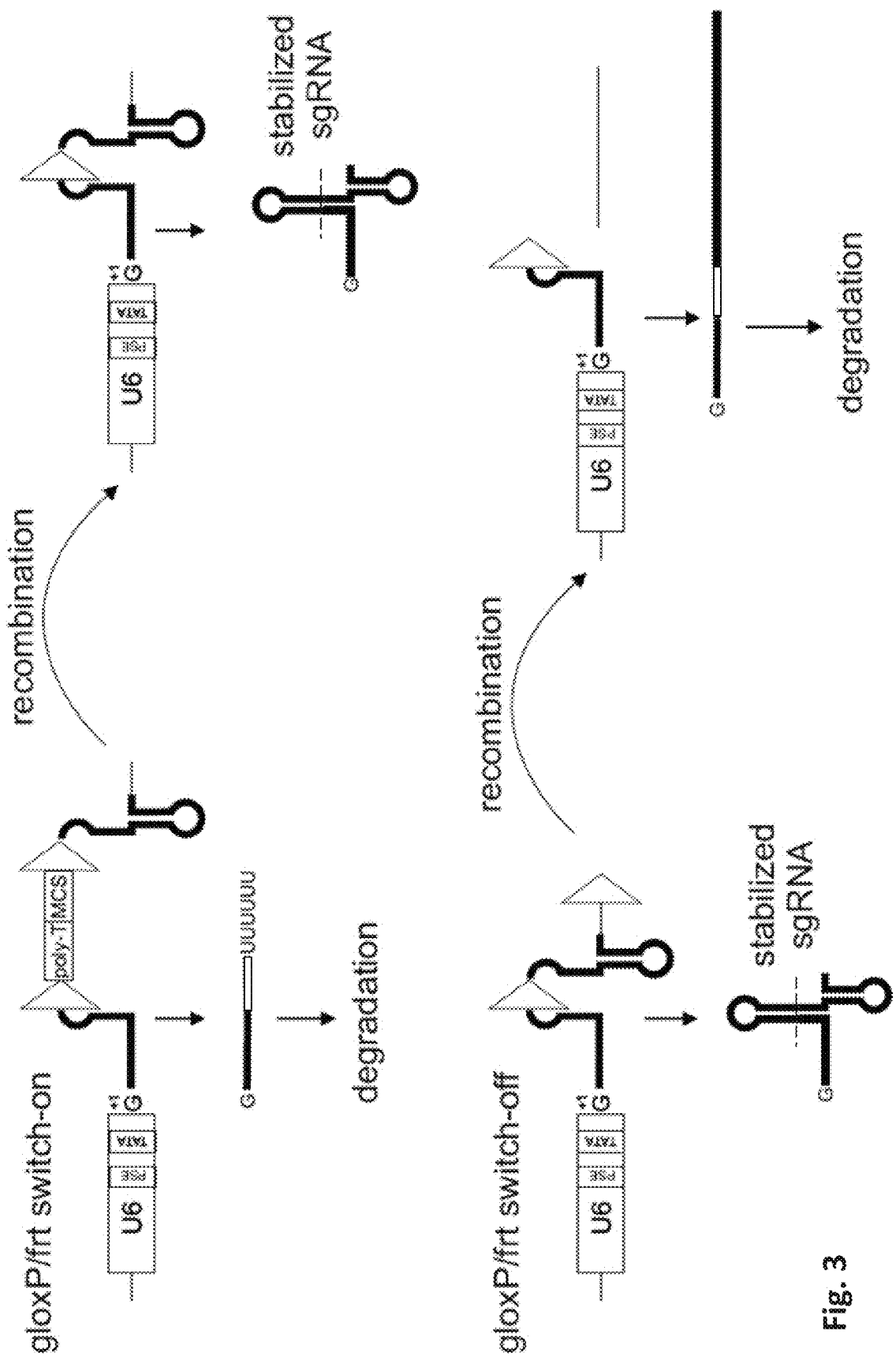

FIG. 3. gFRT scaffold switch on/off systems. The first stem-loop (white boxed line) represents stemloop structure formed by inserted recombination site that prolongs and stabilizes repeat:anti-repeat stemloop of sgRNA.

Figure 4:
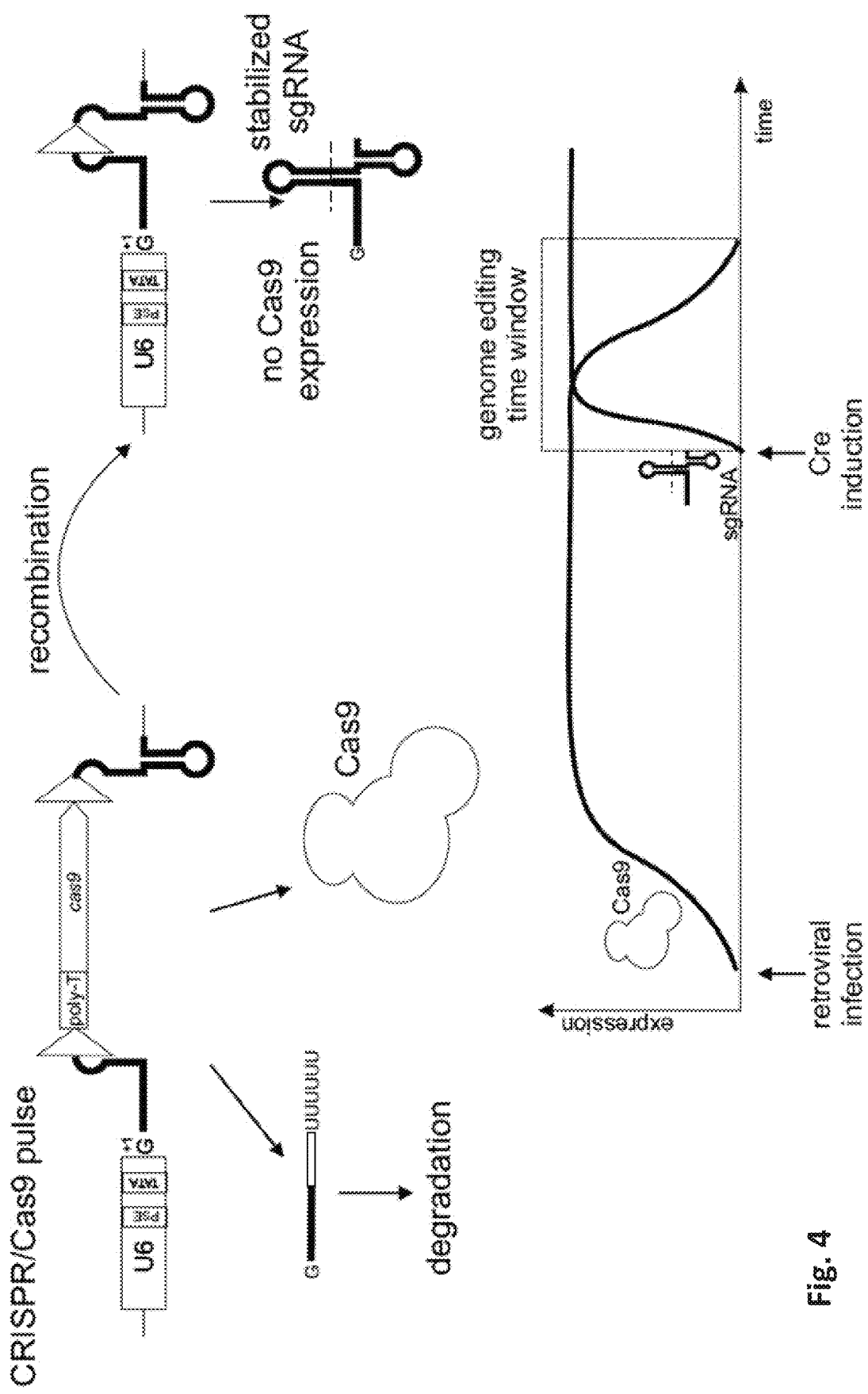

FIG. 4. CRISPR/Cas9 editing pulse system. Schematics of expression cassette prior and post recombination with RNA and protein products are shown on top. Cas9 is produced shortly after infection (bottom, thick line starting at "retroviral infection", reduced in box starting with "Cre induction"). After recombination Cas9 is still produced until Cas9 mRNA is degraded and functional proteins are present in a cell until degraded. Recombination allows production of functional sgRNA (thick line starting at "Cre induction"). Genome editing is possible only within short time window when both components are present.

FIG. 5: In silico folding of basic and novel sgRNA constructs
5A) Dual RNA hybrids of crRNA and tracrRNA fold into several hairpins recognized and bound by the Cas9 protein, including repeat:anti-repeat stemloop and 3 downstream stemloops within tracrRNA (SEQ ID NO: 1 and 2). While the fusion to a chimeric RNA by the standard scaffold shortened the repeat:anti-repeat hairpin structure (SEQ ID NO: 3), other modifications extended the stem regions. The optimized scaffold (SEQ ID NO: 4) is shown to enhance editing efficiency. gRNA 2.0 scaffold contains two MS2 sequences (SEQ ID NO: 5) 5B) Introduction into the optimized scaffold (SEQ ID NO: 4) of Flp recombination targets (FRT) (SEQ ID NO: 6) or loxP sites (SEQ ID NO: 7) on a top of a stemloop will also increase length and thermodynamic stability of the hairpin due to the palindromic nature of the sequence. Predicted secondary structures were prepared using RNAfold algorithm of Vienna RNA package with manual modifications within repeat: anti-repeat bulge and first stemloop of tracrRNA according to experimentally determined RNA structure. All structures were visualized with Varna software.

Figure 6:
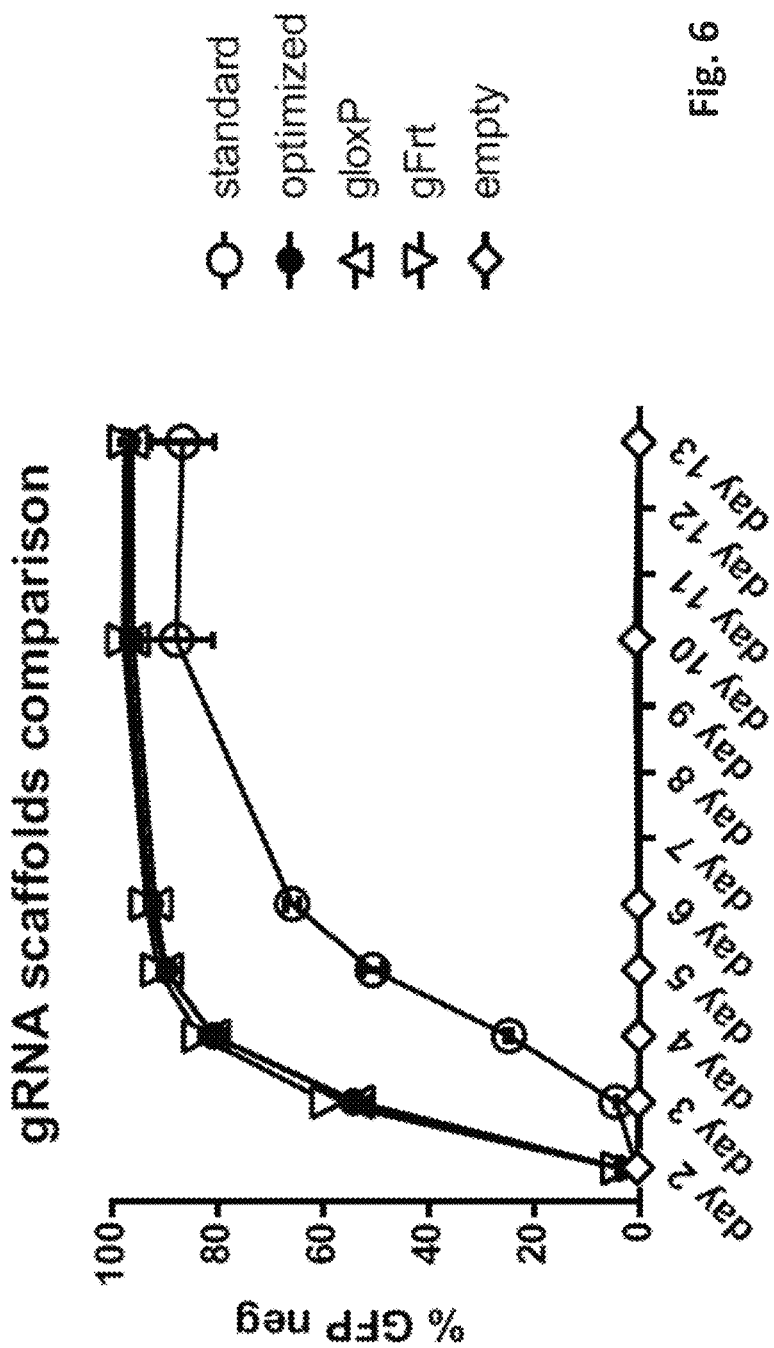

FIG. 6: Introduction of site sequence recombination sites into the scaffold does not reduce editing efficiency.
Shown is sgRNA targeting GFP-encoding gene present in 2 copies (homozygous) in mouse embryonic stem cells (ES cells) expressing Cas9. Kinetic analysis of GFP loss using flow cytometry revealed an outperformance of knock-out efficiency by all modifications compared to the standard sgRNA structure. Introduction of FRT showed even slightly increased efficiency over the optimized scaffold. Error bars are standard deviation in biological triplicates.

Figure 7:
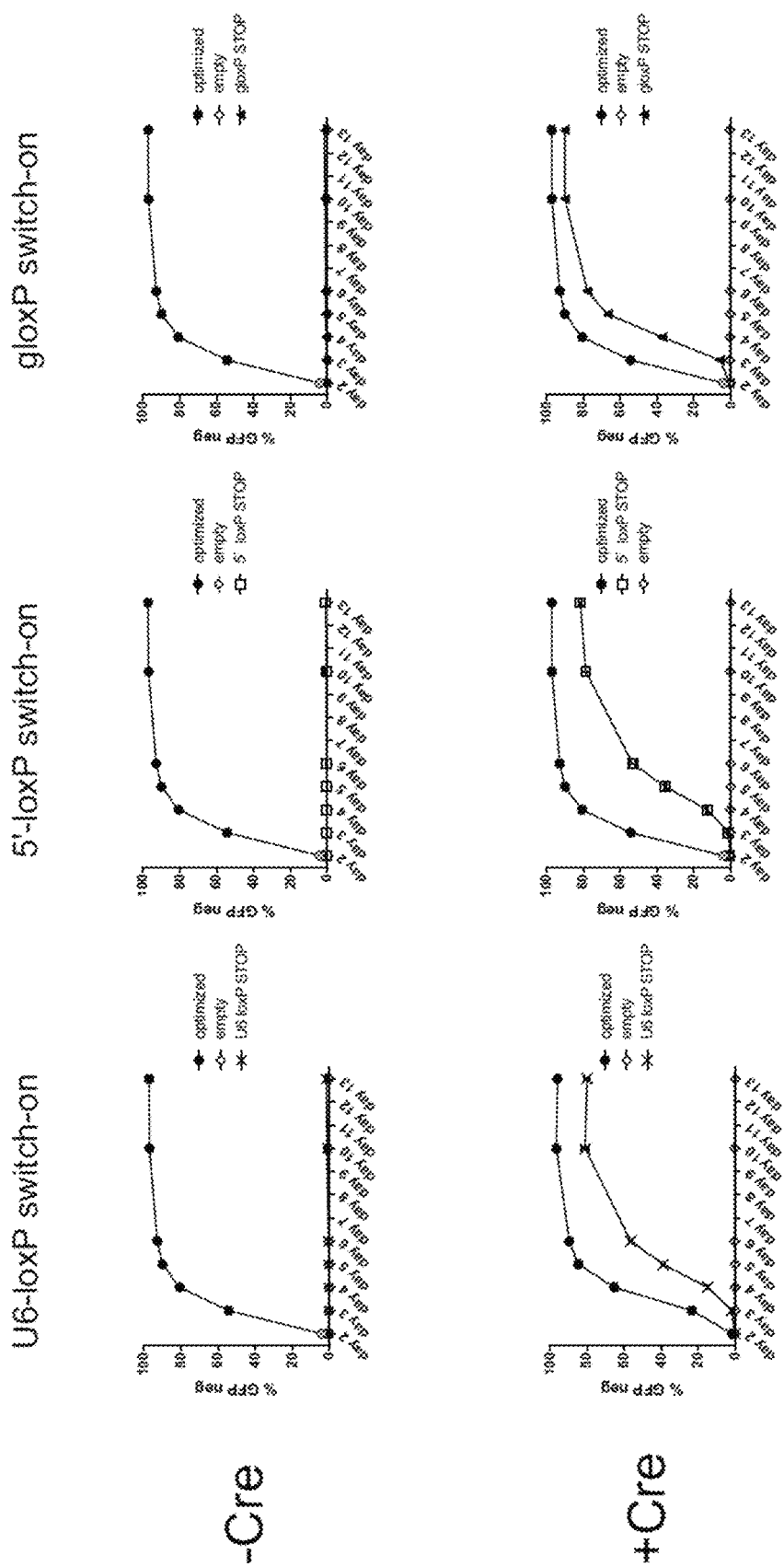

FIG. 7: Tight inducible guide expression using Cre recombinase.
Shown are sgRNA constructs carrying the guide against GFP in ES cells with stable Cas9 expression with or without additional stable expression of Cre recombinase. Three localizations of loxP-STOP-loxP cassette were tested: within U6 promoter, disturbing the distance between U6 promoter elements (left panel); at the 5'-start of gRNA, immediately following a +1G transcription start site (middle panel) and within the gRNA scaffold on the top of repeat: anti-repeat stemloop (right panel). The presence of a loxP-STOP-loxP cassette completely abrogated editing in all 3 positions in Cre-negative cells (top). Excision of the STOP signal by Cre recombinase resulted in robust editing (bottom). Error bars are standard deviation in biological triplicates.

Figure 8:
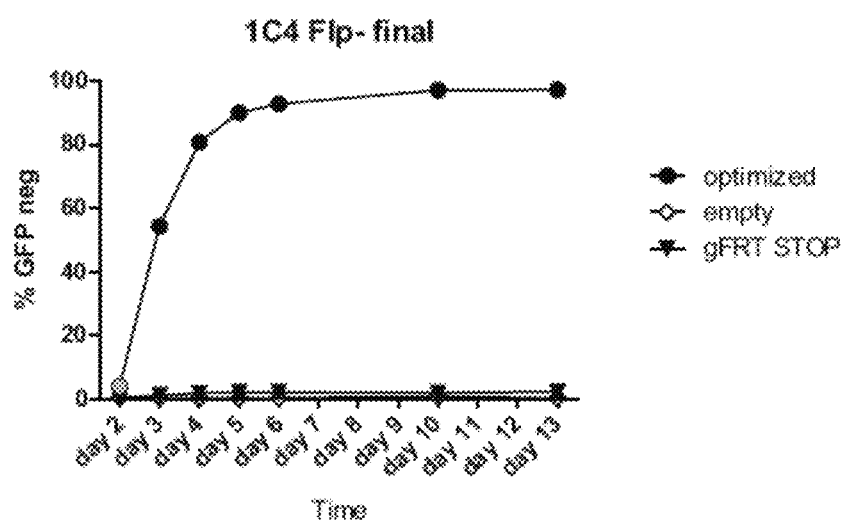
Figure 8:
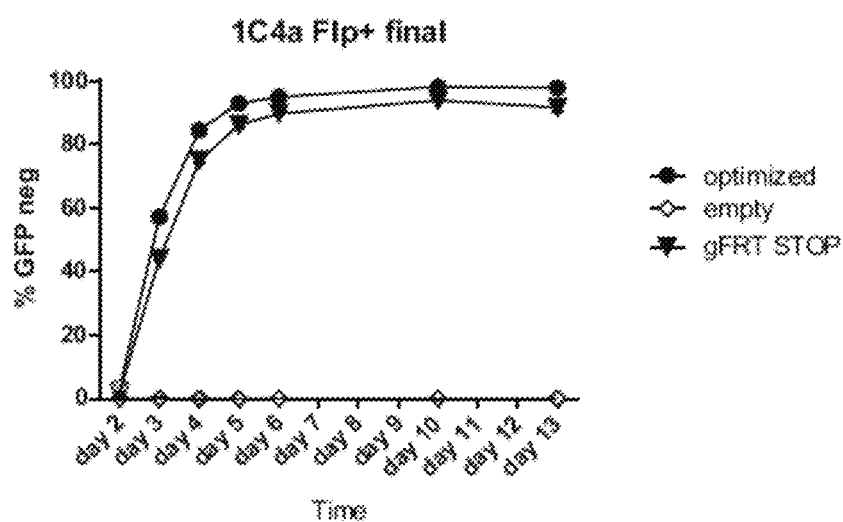

FIG. 8: Tight inducible guide expression using Flp recombinase.
Shown is an sgRNA construct carrying the guide against GFP in ES cells with stable Cas9 expression with or without additional expression of Flp recombinase. While the presence of an FRT-STOP-FRT cassette within the gRNA scaffold, on the top of repeat: anti-repeat stemloop completely abrogated editing (top), excision of the STOP signal by Flp recombinase resulted in robust editing (bottom). Error bars are standard deviation in biological triplicates.

Figure 9:
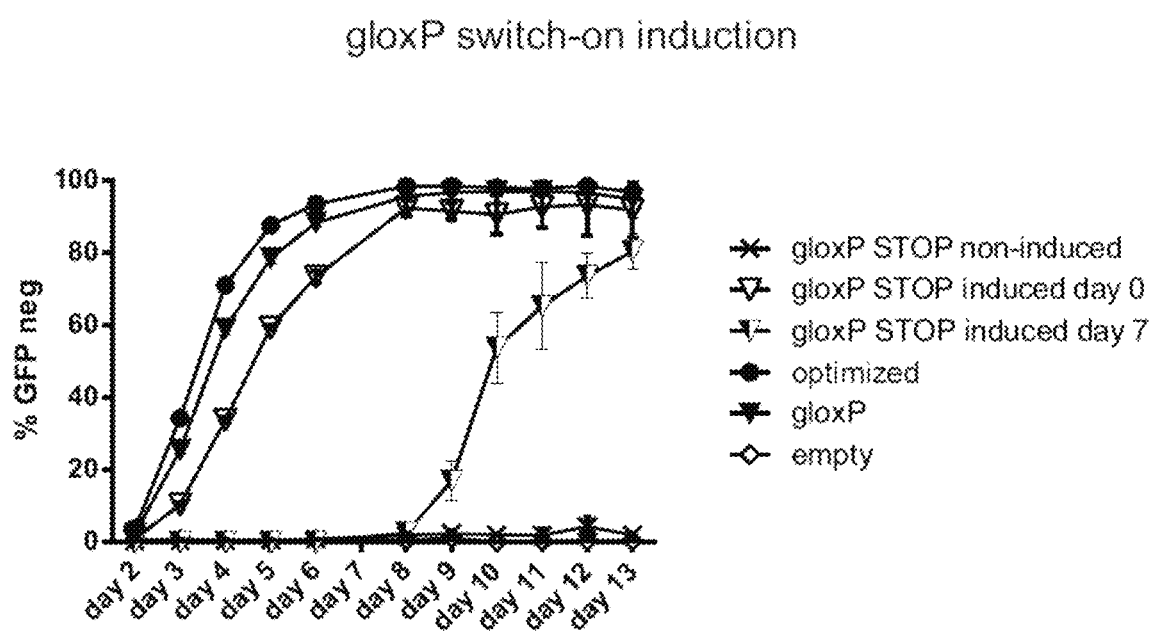

FIG. 9: Timed inducible guide expression using CreERT2.
Shown are sgRNA constructs carrying the guide against GFP and loxP-STOP-loxP cassettes at three different positions (see as well FIG. 7) in ES cells with stable Cas9 expression as well as expression of an inducible Cre recombinase, CreERT2. Addition of 40H-Tamoxifen on day 2 or 7 resulted in removal of a stop cassette, thus in initiation of editing. Error bars are standard deviation in biological triplicates.

Figure 10:
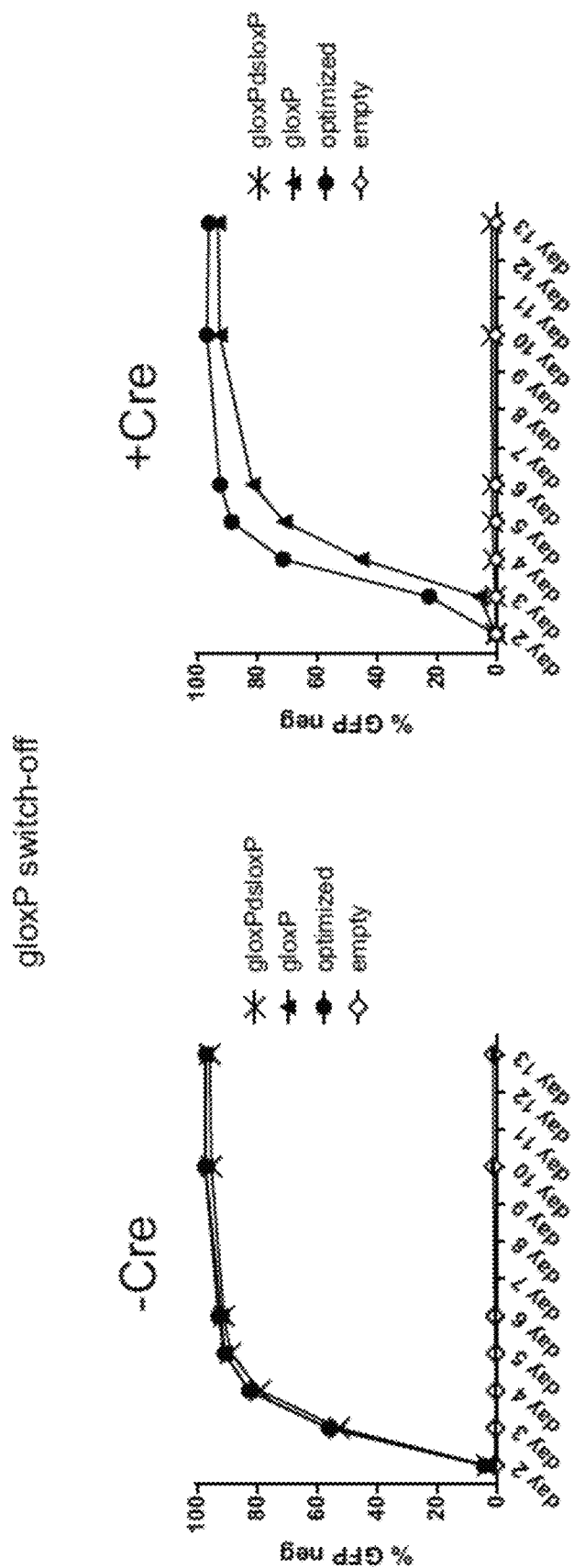

FIG. 10: Removal of 3' sgRNA part results in abrogation of editing
Shown are results of introducing a single loxP site within sgRNA scaffold (repeat:anti-repeat stem loop) and placing a second loxP site downstream of the scaffold. While such construct was capable of editing with the same kinetics as the optimized scaffold in absence of Cre recombinase, its expression efficiently removed sgRNA motifs responsible for Cas9 binding together with sgRNA transcription termination signal and thereby prevented any genome editing showing that the system allows for efficient termination of editing activity without compromising the efficiency of an active sgRNA form. Error bars are standard deviation in biological triplicates.

Figure 11:
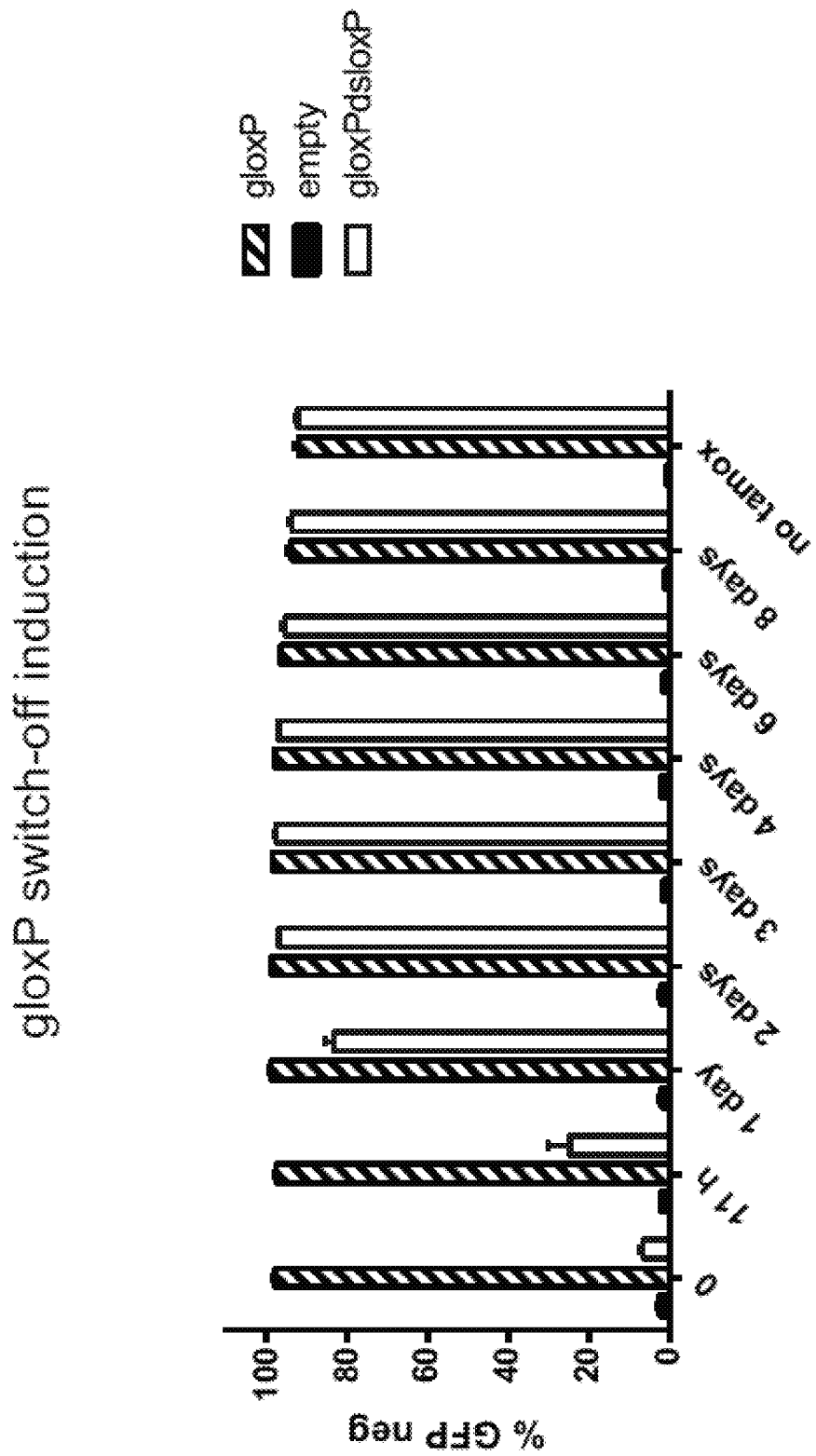

FIG. 11: Timed termination of editing by Cre recombinase
Tested is recombinase activity of CreERT2 using 40H-tamoxifen at different time points after infection of cells with retrovirus delivering the guide sequence containing loxP sites within and downstream of sgRNA scaffold (see as well FIG. 10). GFP loss was quantified at day 11. While editing was almost prevented upon addition of tamoxifen at time of infection, addition 24 h later already resulted in >80% editing and reached saturation after 2 days. Error bars are standard deviation in biological triplicates.

Figure 12A:
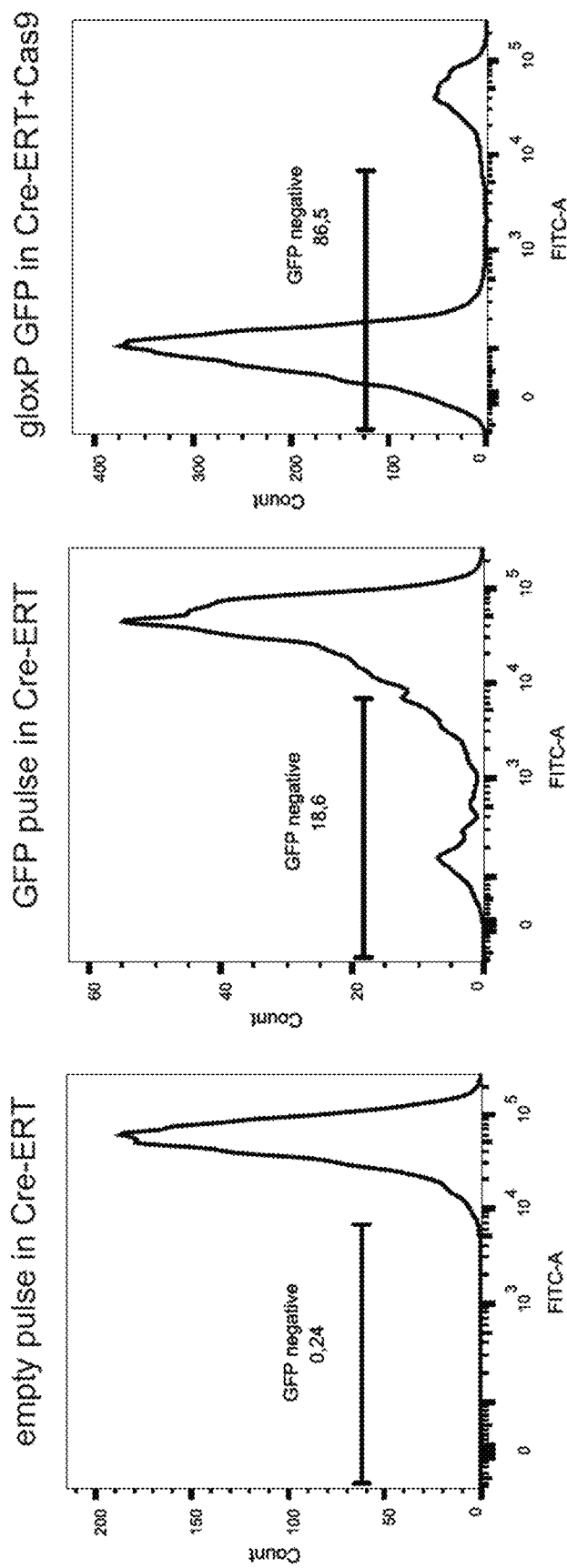
Figure 12B:
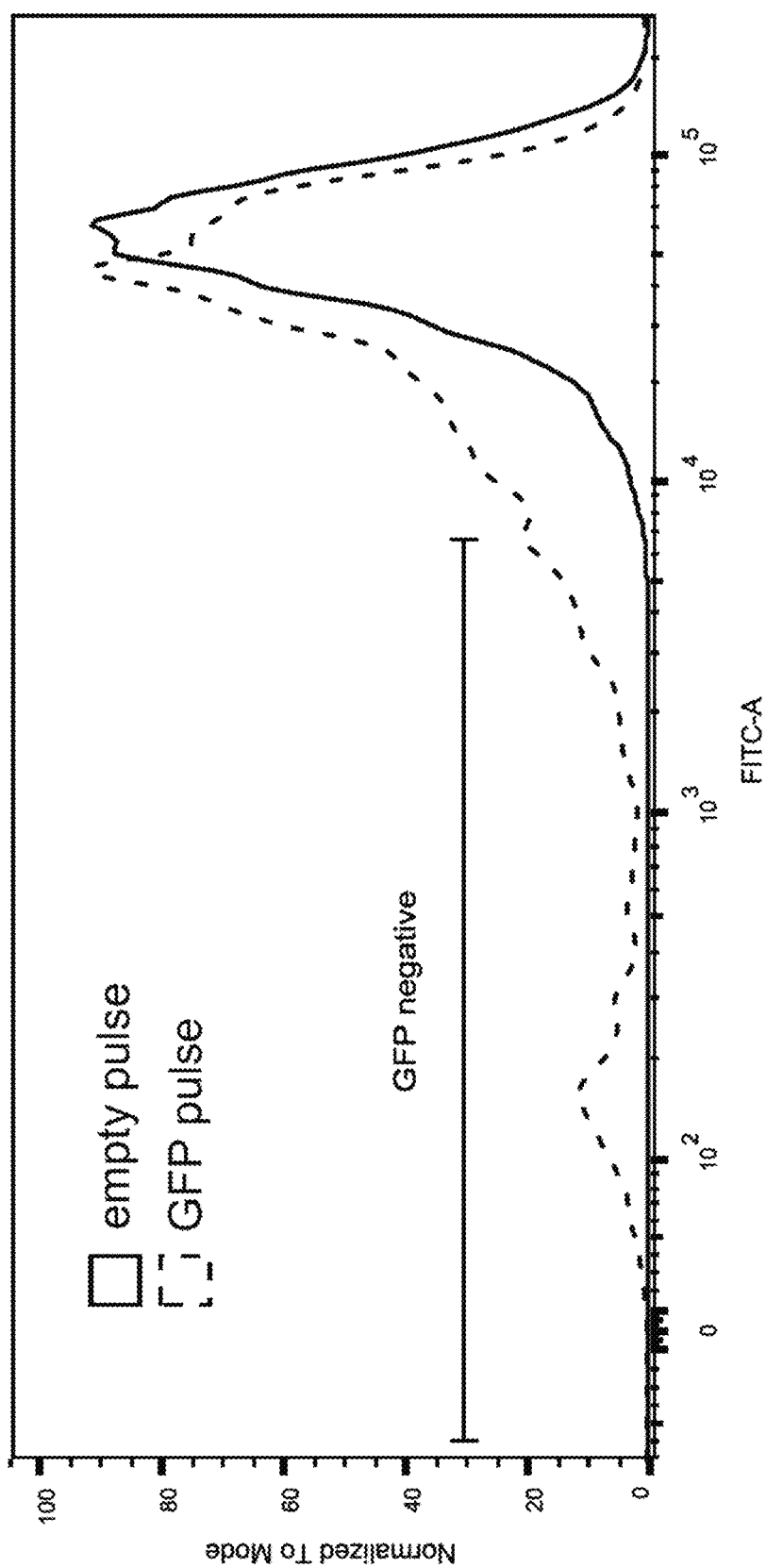
Figure 12C:
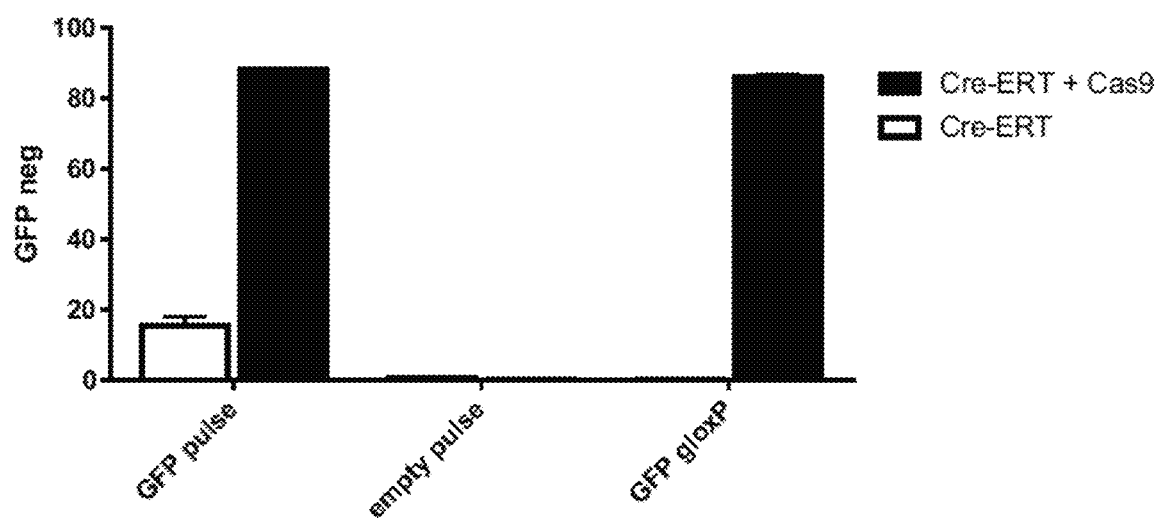

FIG. 12: Editing-pulse
Flow cytometric analysis of cell lines stably expressing tamoxifen inducible Cre recombinate (CreERT) as well as GFP in presence or absence of stable Cas9 expression.
A) Transfection with the editing-pulse construct without guide does not result in GFP editing, while cells carrying the GFP guide in the editing pulse show significant and partial loss of GFP upon tamoxifen treatment. Please note the big fraction of cells with only reduced GFP levels presumably due to heterozygous GFP loss and the smaller fraction of cells with complete loss. As control, the editing pulse was also transduced into cells with stable Cas9 expression resulting in the expected high degree of homozygous GFP loss. B) Overlay of GFP intensity distribution in cells transduced with an editing-pulse construct either empty or carrying the guide against GFP to illustrate the appearance of a cell population with lower GFP expression level.
C) Bar graph summarizing the results of 3 biological replicates with error bars representing standard deviation. Editing of the CreERT cell line without Cas9 (white bars) can only be detected in presence of the CRISPR pulse and does not reach saturation of editing as the control does with stable Cas9 expression.

Figure 13A:
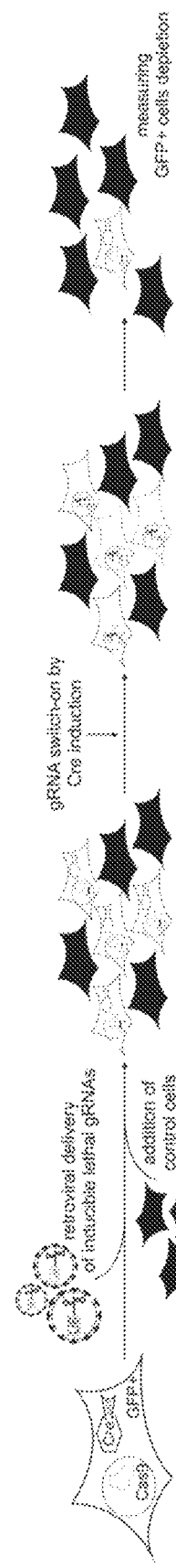
Figure 13B:
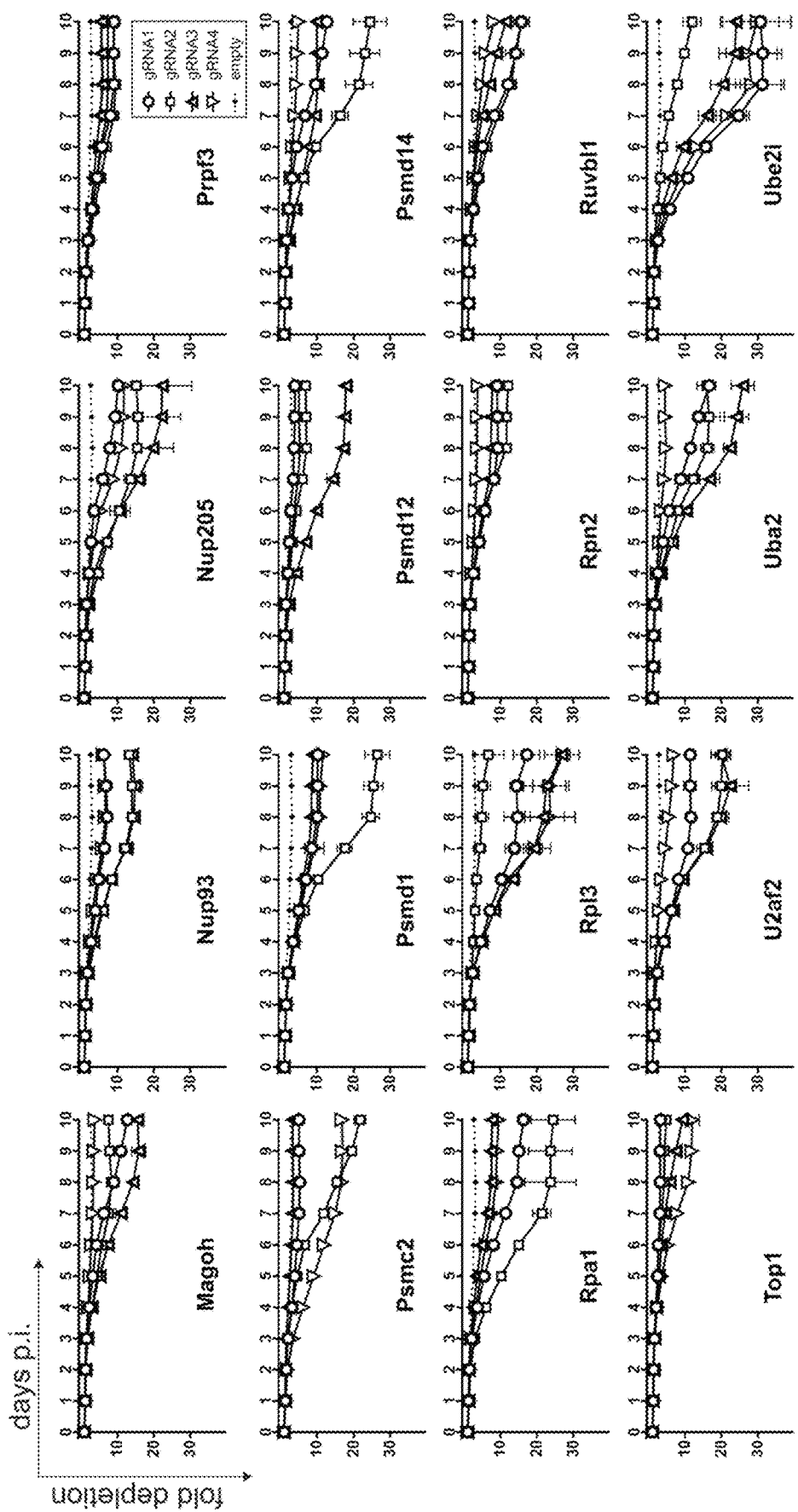

FIG. 13—Timed deletion of essential genes
a. Experimental setup; EGFP+ cells encoding Cas9 and Cre-ERT2 (white cells) were infected with retroviruses containing gloxP-STOP constructs of sgRNAs against essential genes. mCherry+ cells (black cells) were subsequently added as a control for unspecific cell death. Lethal sgRNAs in EGFP+ cells were then switched-on by Cre-ERT2 induction with 4OH-Tamoxifen. sgRNAs activity was assessed by measurement of fold GFP depletion (EGFP+ cell number/mCherry+ cell number). b. Total 64 sgRNAs against 16 essential genes were used as indicated. The graphs represent EGFP+ cells fold depletion over 10 days post induction (days p.i.).

Figure 14:
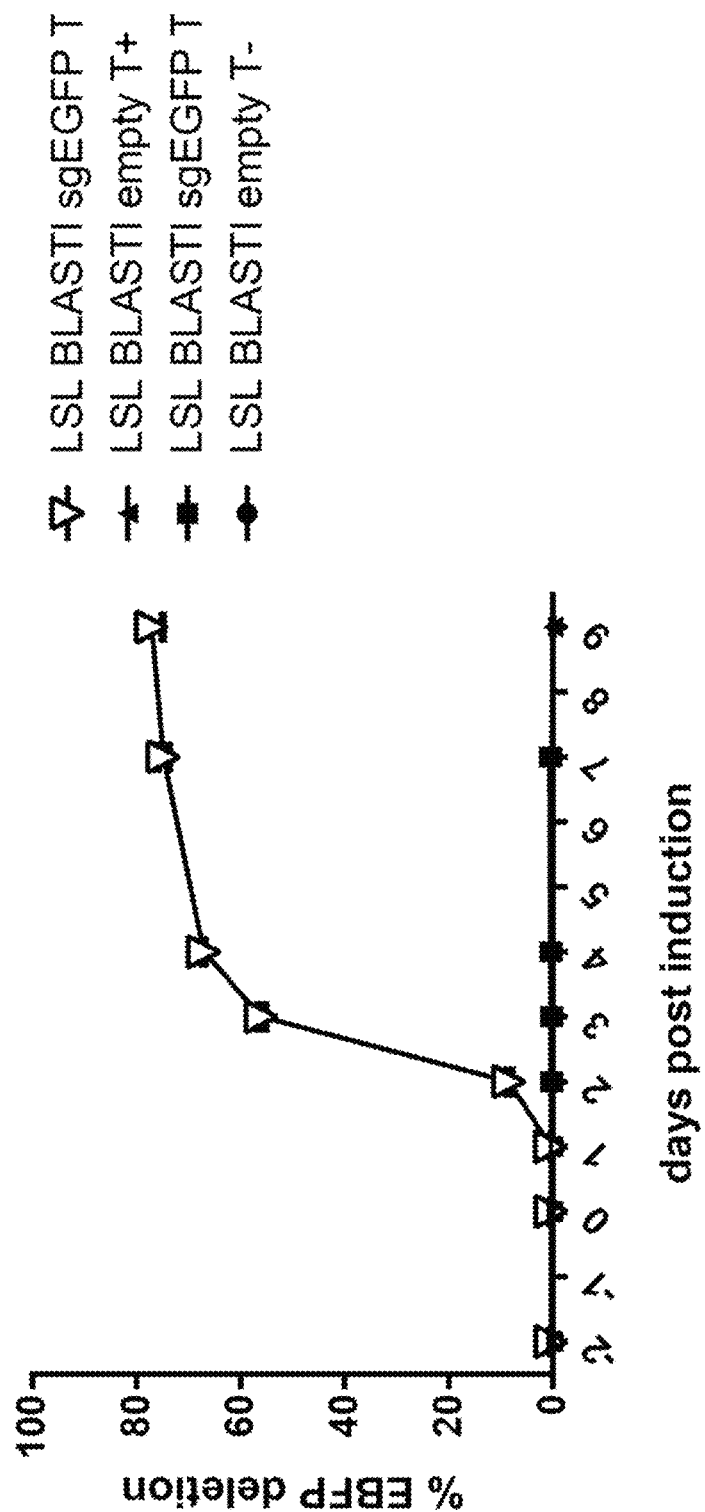

FIG. 14—Highly efficient LSL BLASTI cassette.
EBFP loss was monitored before (days −2 and 0) and after sgRNA switch-on by Cre-ERT2 induction over 9 days. LSL BLASTI, SEQ ID No. 22; T+, 4OH Tamoxifen induction on day 0; T−, no induction. Note high rate of EBFP loss in switched-on construct and very low leakiness observed in non-induced construct.

Figure 15:
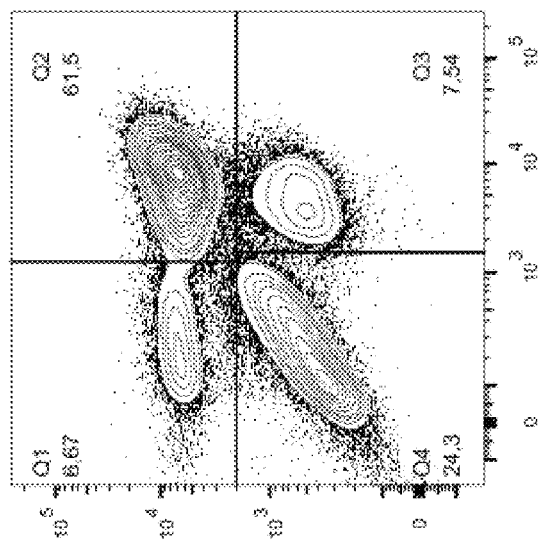
Figure 15:
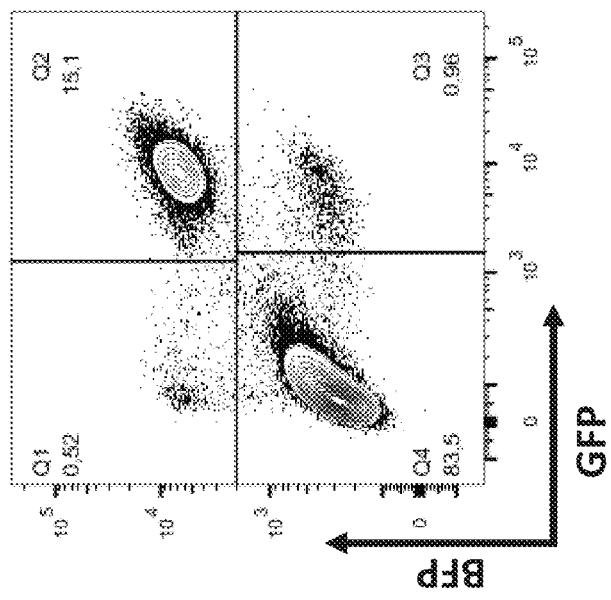

FIG. 15—Editing pulse allows for efficient creation of heterozygous deletion mutants.
GFP and EBFP loss was checked in cells with constitutive expression of Cas9 and sgRNA (left) and in cells treated with editing pulse (See FIG. 4 and Example 18) (right). Note that although the overall editing efficiency of the editing pulse is lower it can create single (heterozygous) deletions with 10 times higher efficiency.

EXAMPLES

Example 1: Cell Culture and Media

Packaging cells (Platinum-E Retroviral Packaging Cell Line and LentiX lentiviral packaging cell line) for producing Retrovirus and Lentivirus were cultured in DMEM supplemented with 15% FBS, 100 Um$^{-1}$ penicillin, 100 ugml$^{-1}$ streptomycin, sodium pyruvate (1 mM) and L-glutamine (4 mM) at 37° C. with 5% CO2.
Murine ES cells were maintained in DMEM supplemented with 15% FBS, 100 Uml$^{-1}$ penicillin, 100 μgml$^{-1}$ streptomycin, sodium pyruvate (1 mM), L-glutamine (4 mM), 1× NEAA (Sigma), 1000 U/ml LIF, 0.1 mM 2-mercaptoethanol at 37° C. with 5% CO2.

Example 2: Retrovirus Production

Retroviral constructs were introduced into Platinium-E Retroviral Packaging cells using calcium phosphate transfection. In brief, 20 ug of DNA and 5 ug of helper plasmid were mixed with 125 ul 1 M CaCl$_2$ and brought to 500 ul volume. This mixture was added to 500 ul 2× HBS under agitation. Precipitate formation was allowed for 15 minutes at room temperature and added to PlatinumE cells at 50% confluency in a 10 cm dish. Medium was changed to target cell medium after 16-20 hours and virus was harvested 32-60 hours after transfection at 8-12 hour intervals. Before infection of ES cells, virus containing supernatant was filtrated through 0.45 um pores.

Example 3: Lentivirus Production

Lentiviral constructs were introduced into Lenti X lentiviral packaging cells using the polyethylenimine (PEI)-mediated transient transfection method. In brief, 6 ug of DNA, 3 ug of gagpol packaging helper plasmid and 1.5 ug of VSV-G envelope helper plasmid were mixed in 1 ml DMEM and 33 ul PEI (1 mg/ml PEI in water) were added and vortexed. After 15 minutes at room temperature the mixture was added to Lenti X cells at 50% confluency in a 10 cm dish. Medium was changed to target cell medium after 16-20 hours and virus was harvested 32-60 hours after transfection at 8-12 hour intervals. Before infection of ES cells, virus containing supernatant was filtrated through 0.45 um pores.

Example 4: Flow Cytometry

Cells were sorted on a BD Aria-III and gated for FSC, SSC, GFP, mCherry, and DAPI. Cells were analyzed for GFP expression using a FACS BD LSR Fortessa (BD Biosciences).

Example 5: Modification of U6 Promoter

Elements essential for U6 promoter activity (TATA cassette and Proximal Sequence Element (PSE)) are located at the 3'-end of the U6 sequence (Geiduschek & Kassavetis, 2001). The distances between PSE, TATA and transcription start position are selected for the promoter functioning. Therefore we reasoned, that recombination mediated modification of the promoter represents a potential entry point for the generation of inducibility. We chose to insert the floxed cassette in between those sequences to disrupt the sgRNA transcription. As the distances between PSE, TATA and transcription start site are shorter than single loxP or FRT site, we chose to mutate the U6 promoter sequence at and around TATA box introducing a loxP site engineered to mimic the conserved TATA element by manipulation of non-conserved sequence of loxP loop (see below). Such design allows for insertion of a cassette that disrupts the U6 promoter by changing the distance between PSE and TATA and its recombination mediated removal would represent a switch-on setup. Furthermore, introduction of a single loxP site within U6 promoter and a second loxP site upstream of the promoter sequence would allow for a switch-off system where 5' sequence of the U6 promoter including PSE is deleted upon Cre recombination (FIG. 1)
3' part of U6 promoter sequence was mutated to contain the engineered loxP site with a sequence designed within variable loop to mimic the U6 promoter TATA box as illustrated below. loxP insertion does not change the distance between TATA box and Proximal Essential Element of U6 promoter.

U6 promoter sequence:
(SEQ ID NO: 8)
TTTCCCATGATTCCTTCATATTTGCATATACGATACAAGGCTGTTAGAG

AGATAATTGGAATTAATTTGACTGTAAACACAAAGATATTAGTACAAAA

-continued

```
TACGTGACGTAGAAAGTAATAATTTCTTGGGTAGTTTGCAGTTTTAAAA

TTATGTTTTAAAATGGACTATCATATGCTTACCGTAACTTGAAAGTA

TTTCGATTTCTTGGCTTTATATATCTTGTGGAAAGGACGAAACACC

Engineered U6 promoter with loxP in TATA box:
                                           (SEQ ID NO: 9)
TTTCCCATGATTCCTTCATATTTGCATATACGATACAAGGCTGTTAGAG

AGATAATTGGAATTAATTTGACTGTAAACACAAAGATATTAGTACAAAA

TACGTGACGTAGAAAGTAATAATTTCTTGGGTAGTTTGCAGTTTTAAAA

TTATGTTTTAAAATGGACTATCATATGCTTACCGTAACTTGAAAGTAT

ATAACTTCGTATACTTTATATTATACGAAGTTATGACGAAACACC
```

(TATA box shown in bold; Proximal Sequence Element (PSE) of U6 promoter shown italic and bold; loxP: underlined)

Example 6: Switch-on and Switch-Off Systems with Recombination Site at the 5' Start of sgRNA In a naturally occurring type II CRISPR system, the guiding crRNA (corresponding to guiding sequence of sgRNA) is first expressed as an intermediate that is further trimmed at 5' end to form a guide of 20 nt (Deltcheva et al., 2011). The mechanism is unknown, but it is believed that the trimming is catalyzed by unspecific ribonucleases that cleave 5' part of the guide not protected by Cas9. Consistently, it was shown that in eukaryotic cells the sgRNA with longer, 30 nt guiding sequence is trimmed at the 5' end to form a canonical sgRNA with 20 nt guiding sequence (Ran, Hsu, Lin, et al., 2013). Thus, for the switch-on setup we designed the floxed STOP cassette with polythymidine tract recognized by RNA pol III as a termination signal is inserted at the 5' end of the sgRNA sequence immediately downstream of the +1 guanine (transcription start site of the U6 promoter; see FIG. 2). In the ON state, resulting from Cre-recombination the sgRNA will be expressed with a single loxP sequence at the 5'-end that should be degraded leading to formation of canonical sgRNA. Also this system can be used as a conditional OFF switch. A single recombination site at the 5'-start of sgRNA (ON state) and the second recombination site upstream of the U6 promoter allows for deletion of a whole promoter sequence abrogating sgRNA expression.

Example 7: gFrt and gloxP Scaffold Switch on/Off Systems

It has been shown previously that sgRNA scaffold sequence can be modified by introduction of RNA aptamer sequences at the tops of sgRNA repeat:antirepeat stem-loop and stem-loop II of tracrRNA-derived scaffold without disrupting sgRNA function (Konermann et al., 2015). Both, loxP as well as FRT sites are palindromic sequence with a spacer (loop) element in between. We modified the repeat-antirepeat stem-loop of sgRNA itself by insertion of a recombination site (FIG. 3). Resulting constructs thus have a prolonged stem. Strong secondary structure of sgRNA scaffold were not negatively affected by the insertion, but rather further stabilized. Introduction of a floxed stop cassette within the repeat-antirepeat stem-loop led to expression of sgRNA without essential parts of the scaffold, thus no functional sgRNA will be produced. Removal thus leads to a switch-on system. A system in which a single recombination site is inserted into the scaffold and the second recombination site is inserted downstream of the sgRNA sequence produces a switch-off system by conditionally depleting essential sequence of the tracrRNA structure including the transcriptional terminator.

Predicted secondary structure of canonical sgRNA (also, FIG. 5B top) and sgRNA with an FRT site inserted into repeat: antirepeat (also, FIG. 5B center) is shown with a dot-bracket notation. N20 represents guiding sequence. Repeat: antirepeat stem-loop and 3 scaffold stem-loops (I, II and III) are indicated in bracket notation. The letters "x" represent the base flip proposed by Chen et al.

```
                                                        (SEQ ID NO: 4)
N20((((((.((((((((....)))))))))...))))))..(((..).))......(((....))))
N20GUUUAAGAGCUAUGCUGGAAACAGCAUAGCAAGUUUAAAUAAGGCUAGUCCGUUAUCAACUUGAAAAAGU
     x                                                        x
.(((((((...))))))......
GGCACCGAGUCGGUGCUUUUUU (SEQ ID NO: 6)
N20((((((.((((((((((((((((((.((......)).)))))))))))))))))))...))))))
N20GUUUAAGAGCUAUGCUGGAAGUUCCUAUUCUCUAGAAAGUAUAGGAACUUCCAGCAUAGCAAGUUUAAA
     x            -------------FRTsite-------------            x
)..(((..).))......(((....)))).(((((((...))))))......
UAAGGCUAGUCCGUUAUCAACUUGAAAAAGUGGCACCGAGUCGGUGCUUUUUU
```

Example 8: Proof-of-Concept

In an initial experiment we benchmarked published scaffold structures in a polyclonally Cas9 expressing cell line. We assembled the identical retroviral setup and the same guide expressed with a scaffold that had previously been shown to lead to improved expression levels in imaging studies (Chen et al., 2013) as well as a scaffold carrying aptamer integrations in 2 stem structures (gRNA2.0, Konermann et al., 2015) used for recruitment of proteins via MS2 binding to the aptamer. As negative control we used retrovirus without guide. Selection for retroviral integration was started 24 hours post infection with retroviral particles. On day 4, at completion of selection, Venus-GFP expression level was quantified using flow cytometry. We observed cutting with all scaffolds and even increased cutting efficiency of the "Chen" backbone with 2 modifications, namely a basepair flip removing a four thymidine stretch at the beginning of the scaffold that could be read as a premature termination signal by RNA polymerase III as well as a stabilizing extension of the repeat:antirepeat stemloop structure.

To check the feasibility of our approach to design inducible guides, we set up a proof of concept experiment where we introduced single loxP and/or FRT sites (scars that would result from successful recombination) into above described locations within U6 promoter and sgRNA on a retroviral entry vector. Additionally, we introduced a loxP-STOP-loxP cassette at the 5'-start of sgRNA to check for the tightness of the polythymidine termination system. For direct quantitative readout we used the same sgRNA targeting EGFP. We produced retroviral particles with control constructs and modified constructs and infected Cas9-expressing GFP positive cells. Empty sgRNA construct with standard U6 promoter and Chen scaffold was used as a negative control. Cas9 (wt) as well as Venus-GFP (2 alleles) were expressed stably within the cells from two independent clonal integrations in murine embryonic stem cells.

All loxP/FRT scar constructs used were able to induce GFP loss in 45-77% cells on day 5 compared to 70% loss for the previously published optimized scaffold structure. This is a remarkable efficiency of deletion of two Venus-GFP alleles, as it suggests that due to Venus-GFP mRNA and protein stability, efficient allele loss was reached within about two days. 0.5% of cells were GFP-negative in the negative control. loxP-STOP-loxP construct showed 0.5% GFP-negative cells as the negative control experiment. 8 days post infection, all loxP/FRT scar constructs showed comparable levels of GFP loss of around 80%. loxP-STOP-loxP construct-transfected cells were 1.5% GFP-negative compared to 0.7% GFP-negative cells in the negative control. We therefore concluded that all three proposed sites are feasible locations for the integration of recombination targets.

Furthermore, we identified one specific location, namely the positioning of FRT within the scaffold, to outperform cutting efficiency of previously published optimized scaffold, most likely due to stabilization of sgRNA secondary structure. Thus, our system might provide a further added value of higher activity. These results provide the confirmation, that tight expression switches of sgRNA are possible with this system.

Expression construct illustrations:

```
Standard empty:
U6 promoter-BbsI-XhoI-BbsI-scaffold Standard-PGK-neo
U6 (underlined)-BbsI (GTCTTC/GAAGAC) XhoI (CTCGAG)-scaffold
Standard (bold) part:
                                                            (SEQ ID NO: 10)
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCGGGTCTTCGCTCGAGAGAAGACCTGTTTTAGAGCTAGAAATAGCAAG

TTAAAATAAGGCTAGTCCGTTATCAACTTGAAAAAGTGGCACCGAGTCGGTGCTTTTTTGTTTTAGAGCTAGAAATA

GCAAGTTAAAATAAGGCTAGTCCGTTTTTAGCGCGTGCGCCAATTCTGCAGACAAATGGCTCTAGAGGTACCCGTTA

AGATCGGAAGAGCACACGTCTGAACTCCAGTCACAAAATTATCTCGTATGCCGTCTTATGCTTGTTAATTAACAATT

GCTGGACGA 2.0 empty
U6 promoter-BbsI-XhoI-BbsI-scaffold 2.0-PGK-neo
U6 (underlined)-BbsI (GTCTTC/GAAGAC) XhoI (CTCGAG)-scaffold
2.0 (bold) part:
                                                            (SEQ ID NO: 11)
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCGGGTCTTCGCTCGAGAGAAGACCTGTTTTAGAGCTAGGCCAACATGA

GGATCACCCATGTCTGCAGGGCCTAGCAAGTTAAAATAAGGCTAGTCCGTTATCAACTTGGCCAACATGAGGATCAC

CCATGTCTGCAGGGCCAAGTGGCACCGAGTCGGTGCTTTTTTGTTTTAGAGCTAGAAATAGCAAGTTAAAATAAGGC

TAGTCCGTTTTTAGCGCGTGCGCCAATTCTGCAGACAAATGGCTCTAGAGGTACCCGTTAAGATCGGAAGAGCACAC

GTCTGAACTCCAGTCACAAAATTATCTCGTATGCCGTCTTATGCTTGTTAATTAACAATTGCTGGACGA

Optimized scaffold empty:
U6 promoter-BbsI-XhoI-BbsI-optimized scaffold-PGK-neo
U6 (underlined)-BbsI (GTCTTC/GAAGAC) XhoI (CTCGAG)-optimized scaffold
(bold) part:
                                                            (SEQ ID NO: 12)
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT
```

TTATATATCTTGTGGAAAGGACGAAACACCGGGTCTTCGCTCGAGAGAAGACCTGTTTAAGAGCTATGCTGGAAACA

GCATAGCAAGTTTAAATAAGGCTAGTCCGTTATCAACTTGAAAAAGTGGCACCGAGTCGGTGCTTTTTTGTTTTAGA

GCTAGAAATAGCAAGTTAAAATAAGGCTAGTCCGTTTTTAGCGCGTGCGCCAATTCTGCAGACAAATGGCTCTAGAG

GTACCCGTTAAGATCGGAAGAGCACACGTCTGAACTCCAGTCACAAAATTATCTCGTATGCCGTCTTATGCTTGTTA

ATTAACAATTGCTGGACGA

Standard scaffold sgEGFP:
U6 promoter-guide-scaffold Standard-PGK-neo
U6 (underlined)-EGFP guide (italic)-scaffold Standard (bold) part:
(SEQ ID NO: 13)
AGGTCGTAGATCTCCGCGGTTAATTAAAATGATACGGCGACCACCGAGATCTGTCTTGATCTAGGAGCTACTCATCA ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACCG</u>*GAGCTGGACGGCGACGTAAA*GTTTTAGAGCTAGAAATAGCAAGTTA

AAATAAGGCTAGTCCGTTATCAACTTGAAAAAGTGGCACCGAGTCGGTGCTTTTTTGTTTTAGAGCTAGAAATAGCA

AGTTAAAATAAGGCTAGTCCGTTTTTAGCGCGTGCGCCAATTCTGCAGACAAATGGCTCTAGAGGTACCCGTTAAGA

TCGGAAGAGCACACGTCTGAACTCCAGTCACAAAATTATCTCGTATGCCGTCTTATGCTTGTTAATTAACAATTGCT

GGACGA 2.0 sgEGFP:
U6 promoter-guide-scaffold 2.0-PGK-neo
U6 (underlined)-EGFP guide (italic)-scaffold 2.0 (bold) part:
(SEQ ID NO: 14)
AGGTCGTAGATCTCCGCGGTTAATTAAAATGATACGGCGACCACCGAGATCTGTCTTGATCTAGGAGCTACTCATCA ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACCG</u>*GAGCTGGACGGCGACGTAAA*GTTTTAGAGCTAGGCCAACATGAGGA

TCACCCATGTCTGCAGGGCCTAGCAAGTTAAAATAAGGCTAGTCCGTTATCAACTTGGCCAACATGAGGATCACCCA

TGTCTGCAGGGCCAAGTGGCACCGAGTCGGTGCTTTTTTGTTTTAGAGCTAGAAATAGCAAGTTAAAATAAGGCTAG

TCCGTTTTTAGCGCGTGCGCCAATTCTGCAGACAAATGGCTCTAGAGGTACCCGTTAAGATCGGAAGAGCACACGTC

TGAACTCCAGTCACAAAATTATCTCGTATGCCGTCTTATGCTTGTTAATTAACAATTGCTGGACGA

Optimized scaffold sgEGFP:
U6 promoter-guide-scaffold-PGK-neo
U6 (underlined)-EGFP guide (italic)-optimized scaffold (bold) part:
(SEQ ID NO: 15)
AGGTCGTAGATCTCCGCGGTTAATTAAAATGATACGGCGACCACCGAGATCTGTCTTGATCTAGGAGCTACTCATCA ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACCG</u>*GAGCTGGACGGCGACGTAAA*GTTTAAGAGCTATGCTGGAAACAGCA

TAGCAAGTTTAAATAAGGCTAGTCCGTTATCAACTTGAAAAAGTGGCACCGAGTCGGTGCTTTTTTGTTTTAGAGCT

AGAAATAGCAAGTTAAAATAAGGCTAGTCCGTTTTTAGCGCGTGCGCCAATTCTGCAGACAAATGGCTCTAGAGGTA

CCCGTTAAGATCGGAAGAGCACACGTCTGAACTCCAGTCACAAAATTATCTCGTATGCCGTCTTATGCTTGTTAATT

AACAATTGCTGGACGA

-continued

5' loxP sgEGFP
U6 promoter-G-loxP-guide-optimized scaffold-PGK-neo
U6 (underlined)-G-loxP (underlined, bold)-EGFP guide (italic)-optimized
scaffold (bold) part:

(SEQ ID NO: 16)

AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCGATAACTTCGTATAGCATACATTATACGAAGTTATGAGCTGGACGGC

GACGTAAAGTTTAAGAGCTATGCTGGAAACAGCATAGCAAGTTTAAATAAGGCTAGTCCGTTATCAACTTGAAAAAG

TGGCACCGAGTCGGTGCTTTTTTGTTTTAGAGCTAGAAATAGCAAGTTAAAATAAGGCTAGTCCGTTTTTAGCGCGT

GCGCCAATTCTGCAGACAAATGGCTCTAGAGGTACCCGTTAAGATCGGAAGAGCACACGTCTGAACTCCAGTCACAA

AATTATCTCGTATGCCGTCTTATGCTTGTTAATTAACAATTGCTGGACGA

5' loxP-STOP-loxP sgEGFP
U6 promoter-G-loxP-UUUUUUUU-loxP-guide-optimized scaffold-PGK-neo
U6 (underlined)-G-loxP (underlined, bold)-tc STOP (under-lined, italic)-loxP
(underlined, bold)-EGFP guide (italic)-optimized scaffold (bold) part:

(SEQ ID NO: 17)

AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCGATAACTTCGTATAGCATACATTATACGAAGTTATTTTTTTTTATAA

CTTCGTATAGCATACATTATACGAAGTTATGAGCTGGACGGCGACGTAAAGTTTAAGAGCTATGCTGGAAACAGCAT

AGCAAGTTTAAATAAGGCTAGTCCGTTATCAACTTGAAAAAGTGGCACCGAGTCGGTGCTTTTTTGTTTTAGAGCTA

GAAATAGCAAGTTAAAATAAGGCTAGTCCGTTTTTAGCGCGTGCGCCAATTCTGCAGACAAATGGCTCTAGAGGTAC

CCGTTAAGATCGGAAGAGCACACGTCTGAACTCCAGTCACAAAATTATCTCGTATGCCGTCTTATGCTTGTTAATTA

ACAATTGCTGGACGA gFRTEGFP:
U6 promoter-guide-scaffold FRT-PGK-neo
U6 (underlined)-EGFP guide (italic)-scaffold Chen (bold)-FRT (underlined,
bold) part:

(SEQ ID NO: 18)

AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCGGAGCTGGACGGCGACGTAAAGTTTAAGAGCTATGCTGGAAGTTCCT

ATTCTCTAGAAAGTATAGGAACTTCCAGCATAGCAAGTTTAAATAAGGCTAGTCCGTTATCAACTTGAAAAAGTGGC

ACCGAGTCGGTGCTTTTTTGTTTTAGAGCTAGAAATAGCAAGTTAAAATAAGGCTAGTCCGTTTTTAGCGCGTGCGC

CAATTCTGCAGACAAATGGCTCTAGAGGTACCCGTTAAGATCGGAAGAGCACACGTCTGAACTCCAGTCACAAAATT

ATCTCGTATGCCGTCTTATGCTTGTTAATTAACAATTGCTGGACGA

U6 loxP sgEGFP
U6 promoter-PSE-loxP-TATA box-guide-optimized scaffold-PGK-neo
U6 (underlined)-Proximal Essential Element (underlined, italic)-consensus
loxP (underlined, bold) with TATA box (TTTATA in italic)-EGFP guide
(italic)-optimized scaffold (bold) part:

(SEQ ID NO: 19)

AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

-continued

```
TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACGGTAACTTGAAAGTATATAACTTCGTATACT

TTATATTATACGAAGTTATGACGAAACACCGGAGCTGGACGGCGACGTAAAGTTTAAGAGCTATGCTGGAAACAGCA

TAGCAAGTTTAAATAAGGCTAGTCCGTTATCAACTTGAAAAAGTGGCACCGAGTCGGTGCTTTTTTGTTTTAGAGCT

AGAAATAGCAAGTTAAAATAAGGCTAGTCCGTTTTTAGCGCGTGCGCCAATTCTGCAGACAAATGGCTCTAGAGGTA

CCCGTTAAGATCGGAAGAGCACACGTCTGAACTCCAGTCACAAAATTATCTCGTATGCCGTCTTATGCTTGTTAATT

AACAATTGCTGGACGA
```

We produced retroviral particles with control constructs Standard and Chen empty and with sgEGFP and the modified constructs 5' loxP sgEGFP, 5' loxP-STOP-loxP sgEGFP, gFRT sgEGFP and U6 loxP in Platinum E cells according to the manufacturers protocol. Empty sgRNA construct with standard U6 promoter and a cognate scaffold was used as a negative control. Cas9-expressing Venus-GFP positive murine embryonic stem cells, that expressed wt Cas9 and two copies of Venus-GFP stably from two previous independent clonal integrations, were infected with retrovirus. Selection with G418 for retroviral integration was started 24 hours after the infection. On day 4, at completion of selection, GFP expression level was quantified using flow cytometry (FITC, pregated for living cells).

The ESC medium contained 82% DMEM, 13.5% FCS, 1x Pen/Strep (Sigma), 2 mM L-Glutamine (Sigma), 1× NEAA (Sigma), 1 mM Na-Pyruvate (Sigma), LIF, 3.5*10$^{-4}$% beta-ME (Sigma).

Expression constructs variants can be used as alternatives to those mentioned above. In particular, it is possible to add an antibiotic resistance sequence between recombinase recognition sites (loxP sites), e.g. in loxP-STOP-loxP constructs instead of just a STOP sequence. Additional expression construct variant illustrations:

```
Standard empty:
U6 (underlined)-transcriptional start +1G (g)-BbsI
(GTCTTC/GAAGAC) XhoI (CTCGAG)-scaffold Standard(bold):
                                                            (SEQ ID NO: 20)
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCgGGTCTTCGCTCGAGAGAAGACCTGTTTTAGAGCTAGAAATAGCAAG

TTAAAATAAGGCTAGTCCGTTATCAACTTGAAAAAGTGGCACCGAGTCGGTGCTTTTTTGTTTTAGAGCTAGAAATA

GCAAGTTAAAATAAGGCTAGTCCGTTTTTAGCGCGTGCGCCAATTCTGCAGACAAATGGCTCTAGAGGTACCCGTTA

AGATCGGAAGAGCACACGTCTGAACTCCAGTCACAAAATTATCTCGTATGCCGTCTTATGCTTGTTAATTAACAATT

GCTGGACGA 2.0 empty:
U6 (underlined)-transcriptional start +1G (g)-BbsI
(GTCTTC/GAAGAC) XhoI (CTCGAG)-scaffold 2.0 (bold):
                                                            (SEQ ID NO: 21)
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCgGGTCTTCGCTCGAGAGAAGACCTGTTTTAGAGCTAGGCCAACATGA

GGATCACCCATGTCTGCAGGGCCTAGCAAGTTAAAATAAGGCTAGTCCGTTATCAACTTGGCCAACATGAGGATCAC

CCATGTCTGCAGGGCCAAGTGGCACCGAGTCGGTGCTTTTTTGTTTTAGAGCTAGAAATAGCAAGTTAAAATAAGGC

TAGTCCGTTTTTAGCGCGTGCGCCAATTCTGCAGACAAATGGCTCTAGAGGTACCCGTTAAGATCGGAAGAGCACAC

GTCTGAACTCCAGTCACAAAATTATCTCGTATGCCGTCTTATGCTTGTTAATTAACAATTGCTGGACGA
```

Optimized scaffold empty:
U6 (underlined)-transcriptional start +1G (g)-BbsI
(GTCTTC/GAAGAC) XhoI (CTCGAG)-optimized scaffold (bold):

(SEQ ID NO: 22)
AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACC</u>gGGTCTTCGCTCGAGAGAAGACCTGTTTAAGAGCTATGCTGGAAACA

GCATAGCAAGTTTAAATAAGGCTAGTCCGTTATCAACTTGAAAAAGTGGCACCGAGTCGGTGCTTTTTTGTTTTAGA

GCTAGAAATAGCAAGTTAAAATAAGGCTAGTCCGTTTTTAGCGCGTGCGCCAATTCTGCAGACAAATGGCTCTAGAG

GTACCCGTTAAGATCGGAAGAGCACACGTCTGAACTCCAGTCACAAAATTATCTCGTATGCCGTCTTATGCTTGTTA

ATTAACAATTGCTGGACGA

Standard scaffold sgEGFP:
U6 (underlined)-transcriptional start +1G (g)-EGFP guide
(italic)-scaffold Standard (bold):

(SEQ ID NO: 23)
AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACC</u>g*GAGCTGGACGGCGACGTAAA*GTTTTAGAGCTAGAAATAGCAAGTTA

AAATAAGGCTAGTCCGTTATCAACTTGAAAAAGTGGCACCGAGTCGGTGCTTTTTTGTTTTAGAGCTAGAAATAGCA

AGTTAAAATAAGGCTAGTCCGTTTTTAGCGCGTGCGCCAATTCTGCAGACAAATGGCTCTAGAGGTACCCGTTAAGA

TCGGAAGAGCACACGTCTGAACTCCAGTCACAAAATTATCTCGTATGCCGTCTTATGCTTGTTAATTAACAATTGCT

GGACGA 2.0 sgEGFP:
U6 (underlined)-transcriptional start +1G (g)-EGFP guide
(italic)-scaffold 2.0 (bold):

(SEQ ID NO: 24)
AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACC</u>g*GAGCTGGACGGCGACGTAAA*GTTTTAGAGCTAGGCCAACATGAGGA

TCACCCATGTCTGCAGGGCCTAGCAAGTTAAAATAAGGCTAGTCCGTTATCAACTTGGCCAACATGAGGATCACCCA

TGTCTGCAGGGCCAAGTGGCACCGAGTCGGTGCTTTTTTGTTTTAGAGCTAGAAATAGCAAGTTAAAATAAGGCTAG

TCCGTTTTTAGCGCGTGCGCCAATTCTGCAGACAAATGGCTCTAGAGGTACCCGTTAAGATCGGAAGAGCACACGTC

TGAACTCCAGTCACAAAATTATCTCGTATGCCGTCTTATGCTTGTTAATTAACAATTGCTGGACGA

Optimized scaffold sgEGFP:
U6 (underlined)-transcriptional start +1G (g)-EGFP guide
(italic)-optimized scaffold (bold) part:

(SEQ ID NO: 25)
AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACC</u>g*GAGCTGGACGGCGACGTAAA*GTTTAAGAGCTATGCTGGAAACAGCA

-continued

TAGCAAGTTTAAATAAGGCTAGTCCGTTATCAACTTGAAAAAGTGGCACCGAGTCGGTGCTTTTTTGTTTTAGAGCT

AGAAATAGCAAGTTAAAATAAGGCTAGTCCGTTTTTAGCGCGTGCGCCAATTCTGCAGACAAATGGCTCTAGAGGTA

CCCGTTAAGATCGGAAGAGCACACGTCTGAACTCCAGTCACAAAATTATCTCGTATGCCGTCTTATGCTTGTTAATT

AACAATTGCTGGACGA

U6 loxP-STOP-loxP sgEGFP:
U6 promoter (all underlined)-Proximal Essential Element
(small, underlined)-consensus loxP (underlined, bold) with TA-TA box
(*TTTATA* underline, bold, italic)-STOP (underlined, italic)-consensus loxP
(underlined, bold) with TATA box (*TTTATA* underline, bold, italic); all
within U6 promoter-transcrip-tional start +1G (g)-EGFP guide (italic)-
optimized scaffold (bold):

(SEQ ID NO: 26)

AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATG</u>cttaccgtaacttgaaagTATATAACTTCGTATACT

TTATATTATACGAAGTTAT*TTTTTTT*ATAACTTCGTATACTTTATATTATACGAAGTTATGACGAAACACCg*GAGC*

*TGGACGGCGACGTAAAG*TTTAAGAGCTATGCTGGAAACAGCATAGCAAGTTTAAATAAGGCTAGTCCGTTATCAACT

TGAAAAAGTGGCACCGAGTCGGTGCTTTTTTGTTTTAGAGCTAGAAATAGCAAGTTAAAATAAGGCTAGTCCGTTTT

TAGCGCGTGCGCCAATTCTGCAGACAAATGGCTCTAGAGGTACCCGTTAAGATCGGAAGAGCACACGTCTGAACTCC

AGTCACAAAATTATCTCGTATGCCGTCTTATGCTTGTTAATTAACAATTGCTGGACGA

U6 loxP sgEGFP:
U6 promoter (all underlined)-Proximal Essential Element
(small underlined)-consensus loxP (underlined, bold) with TA-TA box
(*TTTATA* underline, bold, italic); all within U6 promoter-transcriptional start
+1G (g)-EGFP guide (italic)-optimized scaffold (bold):

(SEQ ID NO: 27)

AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATG</u>cttaccgtaacttgaaagTATATAACTTCGTATACT

*TTATATTATACGAAGTTAT*GACGAAACACCg*GAGCTGGACGGCGACGTAAA*GTTTAAGAGCTATGCTGGAAACAGCA

TAGCAAGTTTAAATAAGGCTAGTCCGTTATCAACTTGAAAAAGTGGCACCGAGTCGGTGCTTTTTTGTTTTAGAGCT

AGAAATAGCAAGTTAAAATAAGGCTAGTCCGTTTTTAGCGCGTGCGCCAATTCTGCAGACAAATGGCTCTAGAGGTA

CCCGTTAAGATCGGAAGAGCACACGTCTGAACTCCAGTCACAAAATTATCTCGTATGCCGTCTTATGCTTGTTAATT

AACAATTGCTGGACGA

5' loxP-STOP-loxP sgEGFP:
U6 (underlined)-transcriptional start +1G (g)-loxP (underlined, bold)-STOP
(underlined, italic)-loxP (underlined, bold)-EGFP guide (italic)-optimized
scaffold (bold):

(SEQ ID NO: 28)

AGGTCGTAGATCTCCGCGGTTAATTAAAATGATACGGCGACCACCGAGATCTGTCTTGATCTAGGAGCTACTCATCA

ACGGTCACATGTGAGGGCCTA<u>TTTCCCATGATTCCTTCATATTTGCATATACGATACAAGGCTGTTAGAGAGATAAT</u>

<u>TGGAATTAATTTGACTGTAAACACAAAGATATTAGTACAAAATACGTGACGTAGAAAGTAATAATTTCTTGGGTAGT</u>

<u>TTGCAGTTTTAAAATTATGTTTTAAAATGGACTATCATATGCTTACCGTAACTTGAAAGTATTTCGATTTCTTGGCT</u>

<u>TTATATATCTTGTGGAAAGGACGAAACACCg</u>ATAACTTCGTATAGCATACATTATACGAAGTTAT*TTTTTTT*TAA

CTTCGTATAGCATACATTATACGAAGTTAT*GGAGCTGGACGGCGACGTAAA*GTTTAAGAGCTATGCTGGAAACAGCA

TAGCAAGTTTAAATAAGGCTAGTCCGTTATCAACTTGAAAAAGTGGCACCGAGTCGGTGCTTTTTTGTTTTAGAGCT

```
AGAAATAGCAAGTTAAAATAAGGCTAGTCCGTTTTTAGCGCGTGCGCCAATTCTGCAGACAAATGGCTCTAGAGGTA

CCCGTTAAGATCGGAAGAGCACACGTCTGAACTCCAGTCACAAAATTATCTCGTATGCCGTCTTATGCTTGTTAATT

AACAATTGCTGGACGA
```

5' loxP sgEGFP:
U6 (underlined)-transcriptional start +1G (g)-loxP (underlined, bold)-EGFP
guide (italic)-optimized scaffold (bold):

(SEQ ID NO: 29)

```
AGGTCGTAGATCTCCGCGGTTAATTAAAATGATACGGCGACCACCGAGATCTGTCTTGATCTAGGAGCTACTCATCA

ACGGTCACATGTGAGGGCCTATTTCCCATGATTCCTTCATATTTGCATATACGATACAAGGCTGTTAGAGAGATAAT

TGGAATTAATTTGACTGTAAACACAAAGATATTAGTACAAAATACGTGACGTAGAAAGTAATAATTTCTTGGGTAGT

TTGCAGTTTTAAAATTATGTTTTAAAATGGACTATCATATGCTTACCGTAACTTGAAAGTATTTCGATTTCTTGGCT

TTATATATCTTGTGGAAAGGACGAAACACCgATAACTTCGTATAGCATACATTATACGAAGTTATGGAGCTGGACGG

CGACGTAAAGTTTAAGAGCTATGCTGGAAACAGCATAGCAAGTTTAAATAAGGCTAGTCCGTTATCAACTTGAAAAA

GTGGCACCGAGTCGGTGCTTTTTTGTTTTAGAGCTAGAAATAGCAAGTTAAAATAAGGCTAGTCCGTTTTTAGCGCG

TGCGCCAATTCTGCAGACAAATGGCTCTAGAGGTACCCGTTAAGATCGGAAGAGCACACGTCTGAACTCCAGTCACA

AAATTATCTCGTATGCCGTCTTATGCTTGTTAATTAACAATTGCTGGACGA
``` g loxP-STOP-loxP sgEGFP:
U6 (underlined)-transcriptional start +1G (g)-EGFP guide (italic)-optimized
scaffold (all bold)-loxP (underlined, bold)-STOP (underlined, bold, italic)-
loxP (underlined, bold); all within optimized scaffold:

(SEQ ID NO: 30)

```
AggtcgtAGATCTCCGCGGTTAATTAAAATGATACGGCGACCACCGAGATCTGTCTTGATCtaggagctactcatca acggtcacatgtgagggcctatttcccatgattccttcatatttgcatatacgatacaaggctgttagagagataat tggaattaatttgactgtaaacacaaagatattagtacaaaatacgtgacgtagaaagtaataatttcttgggtagt ttgcagttttaaaattatgttttaaaatggactatcatatgcttaccgtaacttgaaagtatttcgatttcttggct ttatatatcttGTGGAAAGGACGAAACACCgGAGCTGGACGGCGACGTAAAgtttaagagctatgctgataacttcg tatagcatacattatacgaagttatTTTTTTTTTataacttcgtatagcatacattatacgaagttatcagcatagca agtttaaataaggctagtccgttatcaacttgaaaaagtggcaccgagtcggtgcTTTTTTgttttagagctagaaa tagcaagttaaaataaggctagtccgtTTTTagcgcgtgcgccaattctgcagacaaatggctctagaggtacccgt taAGATCGGAAGAGCACACGTCTGAACTCCAGTCACaaaattATCTCGTATGCCGTCTTaTGCTTGTTAATTAACAA TTGctggacga
``` g loxP-STOP + MCS-loxP sgEGFP:
U6 (underlined)-transcriptional start +1G (g)-EGFP guide (italic)-optimized
scaffold (all bold)-loxP (underlined, bold)-STOP (underlined, bold, italic)-
MCS: NotI (gcggccgc) EcoRI (gaattc) SbfI (cctgcagg)-loxP (underlined, bold);
all within optimized scaffold:

(SEQ ID NO: 31)

```
AggtcgtAGATCTCCGCGGTTAATTAAAATGATACGGCGACCACCGAGATCTGTCTTGATCtaggagctactcatca acggtcacatgtgagggcctatttcccatgattccttcatatttgcatatacgatacaaggctgttagagagataat tggaattaatttgactgtaaacacaaagatattagtacaaaatacgtgacgtagaaagtaataatttcttgggtagt ttgcagttttaaaattatgttttaaaatggactatcatatgcttaccgtaacttgaaagtatttcgatttcttggct ttatatatcttGTGGAAAGGACGAAACACCgGAGCTGGACGGCGACGTAAAgtttaagagctatgctgataacttcg tatagcatacattatacgaagttatTTTTTTTTTTgcggccgcCCAgaattcTGGcctgcaggataacttcgtata gcatacattatacgaagttatcagcatagcaagtttaaataaggctagtccgttatcaacttgaaaaagtggcaccg agtcggtgcTTTTTTgttttagagctagaaatagcaagttaaaataaggctagtccgtTTTTagcgcgtgcgccaat tctgcagacaaatggctctagaggtacccgttaAGATCGGAAGAGCACACGTCTGAACTCCAGTCACaaaattATCT CGTATGCCGTCTTaTGCTTGTTAATTAACAATTGctggacga
```

-continued g loxP-STOP + Blasti-loxP (LSL BLASTI) sgEGFP:
U6 (underlined)-transcriptional start +1G (g)-EGFP guide (italic)-optimized
scaffold (all bold)-loxP (underlined, bold)-STOP (underlined, bold, italic)-
pgk (small, bold)-blasti (small, bold, underlined)-loxP (underlined, bold);
all within optimized scaffold:

(SEQ ID NO: 32)

AggtcgtAGATCTCCGCGGTTAATTAAAATGATACGGCGACCACCGAGATCTGTCTTGATCtaggagctactcatca acggtcacatgtgagggcctatttcccatgattccttcatatttgcatatacgatacaaggctgttagagagataat tggaattaatttgactgtaaacacaaagatattagtacaaaatacgtgacgtagaaagtaataatttcttgggtagt ttgcagttttaaaattatgttttaaaatggactatcatatgcttaccgtaacttgaaagtatttcgatttcttggct ttatatatcttGTGGAAAGGACGAAACACCg*GAGCTGGACGGCGACGTAAA*gtttaagagctatgctgataacttcg tatagcatacattatacgaagttat_TTTTTTTT_gacgcgtaattctaccgggtaggggaggcgcttttcccaaggca gtctggagcatgcgctttagcagccccgctgggcacttggcgctacacaagtggcctctggcctcgcacacattcca catccaccggtaggcgccaaccggctccgttctttggtggccccttcgcgccaccttctactcctcccctagtcagg aagttccccccccgccccgcagctcgcgtcgtgcaggacgtgacaaatggaagtagcacgtctcactagtctcgtgca gatggacagcaccgctgagcaatggaagcgggtaggcctttggggcagcggccaatagcagctttgctccttcgctt tctgggctcagaggctgggaaggggtgggtccggggcgggctcaggggcgggctcaggggcggggcgggcgcccga aggtcctccggaggcccggcattctgcacgcttcaaaagcgcacgtctgccgcgctgttctcctcttcctcatctcc gggcctttcgacctgcagccaatatggccaagcctttgtctcaagaagaatccaccctcattgaaagagcaacggct acaatcaacagcatccccatctctgaggattacagcgtcgccagcgcagctctctctagcgacggccgcatcttcac tggtgtcaatgtatatcattttactggggaccttgtgcagaactcgtggtgctgggcactgctgctgctgcggcag ctggcaacctgacttgtatcgtcgcgatcggaaatgagaacaggggcatcttgagcccctgcggacggtgccgacag gtgcttctcgatctgcatcctgggatcaaagccatagtgaaggacagtgatggacagccgacggcagttgggattcg tgaattgctgccctctggttatgtgtgggagggctgaggggatcataacttcgtatagcatacattatacgaagtta tcagcatagcaagtttaaataaggctagtccgttatcaacttgaaaaagtggcaccgagtcggtgcTTTTTTatcat cagtggtccaggctctagttttgactcaacaatatcaccagctgaagcctatagag g loxP sgEGFP:
U6 (underlined)-transcriptional start +1G (g)-EGFP guide (italic)-optimized
scaffold (bold)-loxP (underlined, bold) within optimized scaffold:

(SEQ ID NO: 33)

AggtcgtAGATCTCCGCGGTTAATTAAAATGATACGGCGACCACCGAGATCTGTCTTGATCtaggagctactcatca acggtcacatgtgagggcctatttcccatgattccttcatatttgcatatacgatacaaggctgttagagagataat tggaattaatttgactgtaaacacaaagatattagtacaaaatacgtgacgtagaaagtaataatttcttgggtagt ttgcagttttaaaattatgttttaaaatggactatcatatgcttaccgtaacttgaaagtatttcgatttcttggct ttatatatcttGTGGAAAGGACGAAACACCg*GAGCTGGACGGCGACGTAAA*gtttaagagctatgctgataacttcg tatagcatacattatacgaagttatcagcatagcaagtttaaataaggctagtccgttatcaacttgaaaaagtggc accgagtcggtgcTTTTTTgttttagagctagaaatagcaagttaaaataaggctagtccgtTTTTagcgcgtgcgc caattctgcagacaaatggctctagaggtacccgttaAGATCGGAAGAGCACACGTCTGAACTCCAGTCACaaaatt ATCTCGTATGCCGTCTTaTGCTTGTTAATTAACAATTGctggacga g FRT-STOP-FRT sgEGFP:
U6 (underlined)-transcriptional start +1G (g)-EGFP guide (italic)-optimized
scaffold (all bold)-FRT (underlined, bold)-STOP (underlined, bold, italic)-
FRT(underlined, bold); all within optimized scaffold:

(SEQ ID NO: 34)

AggtcgtAGATCTCCGCGGTTAATTAAAATGATACGGCGACCACCGAGATCTGTCTTGATCtaggagctactcatca acggtcacatgtgagggcctatttcccatgattccttcatatttgcatatacgatacaaggctgttagagagataat tggaattaatttgactgtaaacacaaagatattagtacaaaatacgtgacgtagaaagtaataatttcttgggtagt ttgcagttttaaaattatgttttaaaatggactatcatatgcttaccgtaacttgaaagtatttcgatttcttggct -continued <u>ttatatatcttGTGGAAAGGACGAAACACCg</u>*GAGCTGGACGGCGACGTAAA*gtttaagagctatgctggaagttcct attctctagaaagtataggaacttc<u>*TTTTTTT*</u>gaagttcctattctctagaaagtataggaacttcagcatagca agtttaaataaggctagtccgttatcaacttgaaaaagtggcaccgagtcggtgcTTTTTTgttttagagctagaaa tagcaagttaaaataaggctagtccgtTTTTagcgcgtgcgccaattctgcagacaaatggctctagaggtacccgt taAGATCGGAAGAGCACACGTCTGAACTCCAGTCACaaaattATCTCGTATGCCGTCTTaTGCTTGTTAATTAACAA TTGctggacga g FRTsgEGFP:
U6 (underlined)-transcriptional start +1G (g)-EGFP guide (italic)-optimized
scaffold (bold)-FRT (underlined, bold) within optimized scaffold:

(SEQ ID NO: 35)

Aggtcgt<u>AGATCTCCGCGGTTAATTAAAATGATACGGCGACCACCGAGATCTGTCTTGATCt</u>aggagctactcatca acggtcacatgtgagggccta<u>tttcccatgattccttcatatttgcatatacgatacaaggctgttagagagataat</u>

<u>tggaattaatttgactgtaaacacaaagatattagtacaaaatacgtgacgtagaaagtaataatttcttgggtagt</u>

<u>ttgcagttttaaaattatgttttaaaatggactatcatatgcttaccgtaacttgaaagtatttcgatttcttggct</u>

<u>ttatatatcttGTGGAAAGGACGAAACACC</u>g*GAGCTGGACGGCGACGTAAA*gtttaagagctatgctggaagttcct attctctagaaagtataggaacttccagcatagcaagtttaaataaggctagtccgttatcaacttgaaaaagtggc accgagtcggtgcTTTTTTgttttagagctagaaatagcaagttaaaataaggctagtccgtTTTTagcgcgtgcgc caattctgcagacaaatggctctagaggtacccgttaAGATCGGAAGAGCACACGTCTGAACTCCAGTCACaaaatt ATCTCGTATGCCGTCTTaTGCTTGTTAATTAACAATTGctggacga g loxP-ds loxP sgEGFP:
U6 (underlined)-transcriptional start +1G (g)-EGFP guide (italic)-optimized
scaffold (bold)-loxP (underlined, bold) within optimized scaffold-loxP
(underlined, bold):

(SEQ ID NO: 36)

Aggtcgt<u>AGATCTCCGCGGTTAATTAAAATGATACGGCGACCACCGAGATCTGTCTTGATCt</u>aggagctactcatca acggtcacatgtgagggccta<u>tttcccatgattccttcatatttgcatatacgatacaaggctgttagagagataat</u>

<u>tggaattaatttgactgtaaacacaaagatattagtacaaaatacgtgacgtagaaagtaataatttcttgggtagt</u>

<u>ttgcagttttaaaattatgttttaaaatggactatcatatgcttaccgtaacttgaaagtatttcgatttcttggct</u>

<u>ttatatatcttGTGGAAAGGACGAAACACC</u>g*GAGCTGGACGGCGACGTAAA*gtttaagagctatgctg<u>ataacttcg</u>

<u>tatagcatacattatacgaagttat</u>cagcatagcaagtttaaataaggctagtccgttatcaacttgaaaaagtggc accgagtcggtgcTTTTTTgttttagagctagaaatagcaagttaaaataaggctagtccgtTTTTagcgcgtgcgc caattctgcag<u>ataacttcgtatagcatacattatacgaagttat</u>acaaatggctctagaggtacccgttaAGATCG GAAGAGCACACGTCTGAACTCCAGTCACaaaattATCTCGTATGCCGTCTTaTGCTTGTTAATTAACAATTGctgga cga g loxP-ds loxP sgEGFP switched-off:
U6 (underlined)-transcriptional start +1G (g)-EGFP guide
(italic)-optimized scaffold partial (bold)-loxP (underlined, bold):

(SEQ ID NO: 37)

Aggtcgt<u>AGATCTCCGCGGTTAATTAAAATGATACGGCGACCACCGAGATCTGTCTTGATCt</u>aggagctactcatca acggtcacatgtgagggccta<u>tttcccatgattccttcatatttgcatatacgatacaaggctgttagagagataat</u>

<u>tggaattaatttgactgtaaacacaaagatattagtacaaaatacgtgacgtagaaagtaataatttcttgggtagt</u>

<u>ttgcagttttaaaattatgttttaaaatggactatcatatgcttaccgtaacttgaaagtatttcgatttcttggct</u>

<u>ttatatatcttGTGGAAAGGACGAAACACC</u>g*GAGCTGGACGGCGACGTAAA*gtttaagagctatgctg<u>ataacttcg</u>

<u>tatagcatacattatacgaagttat</u>acaaatggctctagaggtacccgttaAGATCGGAAGAGCACACGTCTGAACT CCAGTCACaaaattATCTCGTATGCCGTCTTaTGCTTGTTAATTAACAATTGctggacga

Example 9: Editing Pulse

Insertion of cas9 into the floxed cassette creates a system in which Cas9 and sgRNA cannot be expressed simultaneously but will overlap due to mRNA and protein stability. Upon recombination, Cas9 expression is switched off and sgRNA—switched on. Only a short time window in which both components are present due to Cas9 mRNA and protein stability and rapid expression of sgRNA, allows for genome editing (FIG. 4). Given the high activity of the guides fused to our scaffold structure presented herewith, this should provide higher specificity of the system as off-targeting was shown to be associated with high and prolonged expression of Cas9 and sgRNA.

A very tight temporal control of genome editing improves on-target to off-target ratio dramatically. This is best illustrated by transfection of purified recombinant Cas9 protein complexed with in vitro synthesized sgRNA, a method shown to assure up to 20-fold higher on- to off-target cleavage ratio compared to standard expression of Cas9 from DNA vectors (Cho et al., 2014; Zuris et al., 2015). However, delivery of Cas9 protein is not feasible in many biological settings.

To generate the editing pulse construct, Cas9-P2A-blasticidin resistance was cloned into the multiple cloning site within the loxP-STOP-loxP cassette integrated in the gloxP scaffold. The construct was integrated into a lentiviral backbone, packaged using standard lentiviral packaging protocols, and transduced into ES cells. Cells were selected for blasticidin resistance for 5 days at 5 microgram/ml blasticidin. Subsequently, cells were subjected to tamoxifen for 48 hours, cultivated for additional 5 days, and GFP expression levels were measured using a BD Fortessa. Results are shown in FIG. 12.

Location of the floxed cas9 expression cassette within the guide scaffold allows for timed, rapid and transient expression of the Cas9:sgRNA complex (See FIG. 4, 12). Cas9 is produced shortly after introduction of the construct into the cells, however sgRNA transcription is terminated at the cassette containing the polythymidine tract. Upon Cre/Flippase induction, the cas9 cassette is removed thus stopping the Cas9 de novo expression and allowing for expression of sgRNA with FRT/loxP stabilizing sequence. In this setup, both Cas9 and sgRNA are present in cells only within a short time window until Cas9 mRNA and Cas9 protein degradation. We expect this system to provide higher cleavage specificity, comparable with introduction of purified recombinant Cas9.

When multiplexing is desired, the risk of off-targeting increases with every introduced sgRNA. In the inventive system, multiple constructs can be introduced and switched off simultaneously. Moreover, this system removes cas9 from the genome protecting the cell from potential unspecific Cas9 activity or unwanted spread and uncontrolled crossing of cas9 bearing model organisms strains.

Example 10: Introduction of Site Sequence Recombination Sites into the Scaffold does not Reduce Editing Efficiency sgRNA targeting GFP-encoding gene present in 2 copies (homozygous) was introduced with a retrovirus into mouse embryonic stem cells (ES cells) expressing Cas9. Kinetic analysis of GFP loss using flow cytometry revealed an outperformance of knock-out efficiency by all modifications compared to the standard sgRNA structure (FIG. 6). Introduction of FRT showed even slightly increased efficiency over the optimized scaffold.

Example 11: Tight Inducible Guide Expression Using Cre Recombinase sgRNA constructs carrying the guide against GFP were introduced into ES cells with stable Cas9 expression with or without additional stable expression of Cre recombinase. Three localizations of loxP-STOP-loxP cassette were tested: within U6 promoter, disturbing the distance between U6 promoter elements (FIG. 1); at the 5'-start of gRNA, immediately following a +1G transcription start site (FIG. 2) and within the gRNA scaffold on the top of repeat:anti-repeat stem-loop (FIG. 3). Successful excision of a stop cassette would leave loxP scar within U6 promoter at the TATA box, at the 5'-start of gRNA (transcribed) and on the top of repeat:anti-repeat stem-loop. While the presence of a loxP-STOP-loxP cassette completely abrogated editing in all 3 positions in Cre-negative cells, excision of the STOP signal by Cre recombinase resulted in robust editing (FIG. 7). Best editing kinetics were observed in the gloxP construct carrying the loxP-STOP-loxP cassette within the scaffold. Here, editing was delayed by about 24 hours due to the requirement of Cre.

Example 12: Tight Inducible Guide Expression Using Flp Recombinase

An sgRNA construct carrying the guide against GFP was introduced into ES cells with stable Cas9 expression with or without additional expression of Flp recombinase. While the presence of an FRT-STOP-FRT cassette within the gRNA scaffold, on the top of repeat:anti-repeat stem-loop completely abrogated editing, excision of the STOP signal by Flp recombinase resulted in robust editing (FIG. 8).

Example 13: Timed Inducible Guide Expression Using CreERT2 sgRNA constructs carrying the guide against GFP and loxP-STOP-loxP cassettes at three different positions (FIG. 9, see as well FIG. 7) were introduced into ES cells with stable Cas9 expression as well as expression of an inducible Cre recombinase, CreERT2. Addition of 4OH-Tamoxifen on day 2 or 7 resulted in removal of a stop cassette, thus in initiation of editing (FIG. 9). Thereby, editing can be induced at different time points in cells, previously not displaying any noticeable leaky editing activity.

Example 14: Removal of 3' sgRNA Part Results in Abrogation of Editing

In order to test if excision of the 3' part of the sgRNA scaffold would result in abrogation of editing, we introduced a single loxP site within sgRNA scaffold (repeat:anti-repeat stem loop) and placed a second loxP site downstream of the scaffold. While such construct was capable of editing with the same kinetics as the optimized scaffold in absence of Cre recombinase, its expression efficiently removed sgRNA motifs responsible for Cas9 binding together with sgRNA transcription termination signal and thereby prevented any genome editing showing that the system allows for efficient termination of editing activity without compromising the efficiency of an active sgRNA form (FIG. 10).

Example 15: Timed termination of editing by Cre recombinase

To test if we could terminate editing before saturation and also measure editing kinetics we induced recombinase activity of CreERT2 using 4OH-tamoxifen at different time points after infection of cells with retrovirus delivering the guide sequence containing loxP sites within and downstream of sgRNA scaffold (FIG. 11, see as well FIG. 10). GFP loss was quantified at day 11 While editing was almost prevented upon addition of tamoxifen at time of infection, addition 24 h later already resulted in >80% editing and reached saturation after 2 days (FIG. 11). Continuous guide expression beyond day 2 does not influence the on-target activity of a highly active sgRNA but can result in off-target activity. The kinetics detected here are much faster than the kinetics of GFP loss in Examples 10-14 as it was measured at end point after dilution of GFP signal, while remaining GFP protein in previous figures delays loss of signal during continuous analysis.

Example 16: Switch-on on a Larger Set of Genes—Timed Deletion of Essential Genes Retroviruses were produced in PlatinumE cells as described earlier. For control cell preparation, haploid mouse ESC (creERT+, Cas9+, puroR, EGFP+) were infected with a retrovirus encoding sgEGFP, neomycin resistance and mCherry. Following antibiotic selection (neomycin, 0.5 mg/ml) cells were sorted for EGFP- and mCherry+.

Haploid mouse ESC (creERT+, Cas9+, puroR, EGFP+) were infected with retroviruses encoding sgRNAs against essential genes (SEQ ID No 38-101) in gloxP-STOP-gloxP constructs in 96-well plates in triplicate. One day after infection neomycin (0.5 mg/ml final concentration) selection was started. Five days after infection, neomycin-selected GFP+ ESC containing sgRNAs against essential genes or empty control sgRNAs were mixed with GFP- mCherry+ control cells (day -1). 24 hours later 4OH-Tamoxifen (here and later 0.5 µM final concentration) was added to the cell mixture (day 0) (See FIG. 13a).

As expected, upon 4OH-Tamoxifen-induced expression of sgRNAs against essential genes we observed cell death of EGFP+ ESCs. mCherry+ cells were used to control for unspecific cell death. Experimental readout was the ratio of GFP+ cells over mCherry+ control cells measured by flow cytometry on day 0 and every day until day 10 post induction with 4OH-Tamoxifen normalized to day 0 ratio (See FIG. 13b).

| gene name | identifier | gRNA number | gRNA sequence |
| --- | --- | --- | --- |
| magoh | SEQ ID NO 38 | gRNA1 | GAGTTTGAATTCCGACCTGA |
|  | SEQ ID NO 39 | gRNA2 | GGACTGGTTGACATCAATAA |
|  | SEQ ID NO 40 | gRNA3 | GCCGGCCCACGCGATCAGGA |
|  | SEQ ID NO 41 | gRNA4 | TTGTGTTTTAGGGATCCGGA |
| nup93 | SEQ ID NO 42 | gRNA1 | GCATCTCTAATGGATACTGA |
|  | SEQ ID NO 43 | gRNA2 | GTGTCCTTCACAGGCTCGAG |
|  | SEQ ID NO 44 | gRNA3 | TGTCTGCTATTGAAGAGTCC |
|  | SEQ ID NO 45 | gRNA4 | GCTTGTGATAGAAAGTCGAG |
| nup205 | SEQ ID NO 46 | gRNA1 | TTTTATACTGGGATGGAAAG |
|  | SEQ ID NO 47 | gRNA2 | GCAGCTTGTTGACACTGCGA |
|  | SEQ ID NO 48 | gRNA3 | CATTTCCCTGGCCTCACCAG |
|  | SEQ ID NO 49 | gRNA4 | CTTTATAGACCAAAGCACAG |
| prpf3 | SEQ ID NO 50 | gRNA1 | TCTTCTACCTCCTCAAAACG |
|  | SEQ ID NO 51 | gRNA2 | GGAGCTTTGTTAGCATGCCA |
|  | SEQ ID NO 52 | gRNA3 | GGCTGAATAGTGTTGCCGAT |
|  | SEQ ID NO 53 | gRNA4 | GATCTCAAAGGAATCATCGG |
| psmc2 | SEQ ID NO 54 | gRNA1 | GCTGTGTAATCACCGAGACG |
|  | SEQ ID NO 55 | gRNA2 | CTTGGAATCGAGCCTCCAAA |
|  | SEQ ID NO 56 | gRNA3 | CTTCCGGTGGGGAAGAGAAA |
|  | SEQ ID NO 57 | gRNA4 | GGACCAGCGGAAAACCAAAG |
| psmd1 | SEQ ID NO 58 | gRNA1 | GAGACTCCTCAAAAGCCCCC |
|  | SEQ ID NO 59 | gRNA2 | AAACACTTTCGAGGCCACCA |
|  | SEQ ID NO 60 | gRNA3 | GGCAGTAATAGACAACACAG |
|  | SEQ ID NO 61 | gRNA4 | GATCCTGGAGAAGTGTCCTT |
| psmd12 | SEQ ID NO 62 | gRNA1 | TTATGCTTCTGTCAAAACGA |
|  | SEQ ID NO 63 | gRNA2 | GGAAGTGGACTACAGCGCCA |
|  | SEQ ID NO 64 | gRNA3 | GCAGTGCTGTACTTACGTGG |
|  | SEQ ID NO 65 | gRNA4 | GCGCATTGTGAAGATGGAAG |
| psmd14 | SEQ ID NO 66 | gRNA1 | CCTTACCTTTAGCAAGGCCA |
|  | SEQ ID NO 67 | gRNA2 | ATTAGACCCATAACTTCCAT |
|  | SEQ ID NO 68 | gRNA3 | ACCTACAGATGCTCCTGCCG |
|  | SEQ ID NO 69 | gRNA4 | TTAGGATCCCAAACGTCATT |
| rpa1 | SEQ ID NO 70 | gRNA1 | TATTCCCTGTAGAAATGGGA |
|  | SEQ ID NO 71 | gRNA2 | GCACCTGGAGTAATTCCCGG |
|  | SEQ ID NO 72 | gRNA3 | GTTCCGGCAGGTTTTCCAAA |
|  | SEQ ID NO 73 | gRNA4 | CTACAGGGAATAGGTCACCC |
| rpl3 | SEQ ID NO 74 | gRNA1 | CCGAACAGAGATTAACAAGA |
|  | SEQ ID NO 75 | gRNA2 | TTTTGGCCCATAGTCCTTGC |
|  | SEQ ID NO 76 | gRNA3 | GCGAGTACTTACTCTTCGTA |
|  | SEQ ID NO 77 | gRNA4 | CCGCATCATTGCCCACACTC |
| rpn2 | SEQ ID NO 78 | gRNA1 | CATCTGGCACCTGTACCCCA |
|  | SEQ ID NO 79 | gRNA2 | GCTCGGCTGGATGAACTAGG |
|  | SEQ ID NO 80 | gRNA3 | AGGGCTTCATTGGATGCCAA |
|  | SEQ ID NO 81 | gRNA4 | CTACAAGCTCATGGACCACG |
| ruvbl1 | SEQ ID NO 82 | gRNA1 | AACACCTTGCCAGTTCCAGG |
|  | SEQ ID NO 83 | gRNA2 | ACATCTAGATAAACTTCGAG |
|  | SEQ ID NO 84 | gRNA3 | CCACTTGGCTCACCTCAGAG |
|  | SEQ ID NO 85 | gRNA4 | CCACCTCTCTCGCGTTCTCC |
| top1 | SEQ ID NO 86 | gRNA1 | TTTCTTTCCTCAGATCGAAG |
|  | SEQ ID NO 87 | gRNA2 | GGTTCATCTTTAATTCGTGG |
|  | SEQ ID NO 88 | gRNA3 | GGGCACACTCACCATTCAAT |
|  | SEQ ID NO 89 | gRNA4 | CACGCCGGCCGACATGAGCG |
| u2af2 | SEQ ID NO 90 | gRNA1 | TCGTCGTCTCCTATCCCGAG |
|  | SEQ ID NO 91 | gRNA2 | TCTGACCATAGGCCATTGCG |
|  | SEQ ID NO 92 | gRNA3 | GTACCTCAGTAATGCCAAAA |
|  | SEQ ID NO 93 | gRNA4 | CAGCTCAACGAGAATAAACA |
| uba2 | SEQ ID NO 94 | gRNA1 | CCAGACACATCCTATTCACG |
|  | SEQ ID NO 95 | gRNA2 | GTCACCCTAAGCCTACCCAG |
|  | SEQ ID NO 96 | gRNA3 | GCAGTCCCGCTCTCAATGAG |
|  | SEQ ID NO 97 | gRNA4 | GCTCGAGCATCTAATGAAGA |
| ube2i | SEQ ID NO 98 | gRNA1 | GAGTGCTCCTTACAAAAGGG |
|  | SEQ ID NO 99 | gRNA2 | GCTACTCCATACCTGTTTGA |
|  | SEQ ID NO 100 | gRNA3 | CGCTATCCCTGGAAAGAAGG |
|  | SEQ ID NO 101 | gRNA4 | TCCCTCCCACAGACTCCAT |

Example 17: STOP Cassette Improved by Addition of Blasticidin Resistance Gene Retroviruses encoding sgRNA constructs with LSL BLASTI (SEQ ID No 22) with either no guiding RNA sequence or sgEGFP (targeting as well EBFP) were used for infection of mouse iPS cells constitutively expressing Cas9, EGFP, EBFP and Cre-ERT2 in 24-well plate format in triplicate. One day after infection blasticidin selection (10 µg/ml final concentration) was started and continued for one week. iPSCs were then split into two plates and 4OH-Tamoxifen was added to one of the plates. EBFP loss was monitored by flow cytometry every day for five days (days 0-4) and later at days 7 and 9.

High rate of EBFP loss (90% of overall activity on day 4 post induction) and very low leakiness (<0.5% in all the controls) were observed. See FIG. 14. Compare to FIG. 9.

Example 18: Editing Pulse for Creation of Heterozygous Deletion Mutants

NIH 3T3 MEF cells encoding creERT2 and single copies of GFP and EBFP were infected with a lentivirus encoding for the sgEGFP editing pulse construct (see FIG. 4) and blasticidin resistance gene or with a control lentivirus encoding Cas9-blasticidin and sgEGFP (both constitutively expressed). 1 day post infection blasticidin selection was started and two days later the editing pulse was induced with 4OH-Tamoxifen. GFP and EBFP loss was measured by flow cytometry over one week after induction. sgEGFP RNA targets both GFP and EBFP due to an identical sequence present in the 5' regions of their gene sequences. Such an experimental set-up allows for detection of either a single or double editing event in every cell and thus can be used for assessment of efficiency in creating homozygous or heterozygous deletions of bi-allelic genes.

See FIG. 15. Constitutive expression of Cas9 and sgRNA resulted in deletion of both GFP and EBFP in 83.5% of cells and only about 1.5% cells lost either GFP or EBFP. The editing pulse exhibited generally lower editing efficiency and created a double KO in 24% of cells but in over 15% only one of the genes was deleted. Thus, the editing pulse can be used for efficient creation of heterozygous deletions.

LITERATURE REFERENCES

Anton et al., *Nucleus* 2014, 5(2):163-172Aubrey et al. (2015) *Cell Rep,* 10(8), 1422-1432. doi:10.1016/j.celrep.2015.02.002
Brandon et al., *Cell Reports* 10 (8) (2015): 1422-1432
Briner et al., *Molecular Cell* 2014, 56: 333-339
Cell. Mol. *Life Sci.* (2015) 72:383-399
Chavez et al., *Nature Methods* 2015, 12(4): 326;
Chen et al. (2013) *Cell,* 155(7), 1479-1491. doi:10.1016/j.cell.2013.12.001
Chen et al. *GigaScience* 2014, 3:24
Chen et al. (2014) *Methods in Enzymology,* 546:337
Chen et al., *Cell Research* (2016) doi: 10.1038/cr.2016.3
Cho et al. (2014) *Genome Res,* 24(1), 132-141. doi:10.1101/gr.162339.113
Chylinski et al. (2014) *Nucleic Acids Res,* 42(10), 6091-6105. doi:10.1093/nar/gku241
Cong et al. (2013) *Science,* 339, 819-823.
Deltcheva et al. (2011) *Nature,* 471(7340), 602-607. doi:10.1038/nature09886
Deng et al. (2015) *PNAS,* 112(38): 11870-11875.
Dominguez et al., *Nature Reviews* 2015, doi:10.1038/nrm.2015.2
Doudna, J. A., & Charpentier, E. (2014) *Science,* 346(6213), 1258096. doi:10.1126/science. 1258096
Dow et al. (2015) *Nat Biotechnol,* 33(4), 390-394. doi:10.1038/nbt.3155
Du et al. 2016, Cold Spring Harb Protoc; doi:10.1101/pdb.top086835;
East-Seletsky et al., *Nature* 2016, 538: 270-273
Esvelt et al., *Nature Methods* 2013, 10(11): 1116;
Fonfara et al., *Nucleic Acids Research,* 2014, 42(4): 2577-2590
Geiduschek, E. P., & Kassavetis, G. a. (2001) *Journal of Molecular Biology,* 310(1), 1-26. doi:10.1006/jmbi.2001.4732
Gilbert et al., *Cell* 2013, 154: 442-451;
Guilinger et al., *Nature Biotech* 2014, 32(6): 577
Hendriks et al., *Cell Stem Cell* 2016 18: 53
Hilton et al., *Nature Biotechnology* 2015, 33(5):510;
Hsu et al. (2014) *Cell,* 157(6), 1262-1278. doi:10.1016/j.cell.2014.05.010
Jinek et al. (2012) *Science,* 337(6096), 816-821. doi:10.1126/science.1225829
Kearns et al., *Nature methods* 2015, 12(5):401;
Kleinstiver et al., *Nature* 2015, 523: 481;
Kleinstiver et al. *Nature Biotech* 2015, 33(12):1293.
Kleinstiver et al., *Nature* 2016, doi:10.1038/nature16526
Konermann et al. (2015) *Nature,* 517(7536), 583-588. doi:10.1038/nature14136
Nihongaki et al., *Nature,* 2015, 33(7): 755-760
Nishimasu et al., *Cell* 2014, 156: 935-949
Ma et al. (2014) *Am Soc Gene & Cell Ther,* 3, e161.
Mali et al., *Nature Biotech* 2013, 31(9): 833;
Müller et al., *Mol. Ther.* 2015, doi:10.1038/mt.2015.218Ran et al. (2013) *Cell,* 154(6), 1380-1389. doi:10.1016/j.cell.2013.08.021
Perez-Pinera et al., *Nature Methods* 2013 10(10):973,
Qi et al., *Cell* 2013, 152: 1173-1183
Ran et al. (2013) *Nat Protoc,* 8(11), 2281-2308. doi:10.1038/nprot.2013.143
Savic et al., *Translational Research* 2016, 168: 15-21
Shechner et al., *Nature Methods* 2015, 12(7): 664
Slaymaker et al., *Science* 2016, 351(5268): 84-88;
Steinert et al., *The Plant Journal* 2015, 84: 1295-1305
Truong et al., *Nucleic Acids Research,* 2015, 43(13): 6450
Tsai et al., *Nature Biotech,* 2014, 32(6):569
Ventura et al., *PNAS* 191 (28) (2004): 10380-10385
Wiles et al., *Mamm Genome* (2015) 26:501-510
Wright et al. (2015). *Proc Natl Acad Sci USA,* 112(10), 2984-2989. doi:10.1073/pnas.1501698112
Zalatan et al., *Cell* 2015, 160, 339-350
Zetsche et al. (2015). *Nat Biotechnol,* 33(2), 139-142. doi:10.1038/nbt.3149
Zhang et al. (2015) *Cell,* 163: 759-771.
Zuris et al. (2015). *Nat Biotechnol,* 33(1), 73-80. doi:10.1038/nbt.3081

The invention claimed is:

1. An expression cassette for expression of a single guide RNA (sgRNA) of a clustered regularly interspaced short palindromic repeats (CRISPR)/Cas9 system, said sgRNA having a stem of 15 nucleotides or more, said cassette comprises: a promoter, an sgRNA-encoding sequence that is interrupted by a transcription disruption sequence, and a sequence flanked by at least a pair of recombinase recognition sites, wherein said recombinase recognition sites are in the same orientation and wherein recombinase activated recombination at the pair of recombinase recognition sites is capable of excising said flanked sequence, wherein said flanked sequence contains the transcription disruption sequence, wherein the sgRNA-encoding sequence comprises a stem sequence and a loop sequence with a sequence encoding a Cas9 binding element located in the stem sequence, and wherein the sgRNA-encoding sequence that is interrupted by the transcription disruption sequence is capable of expressing the sgRNA through the recombinase activated recombination, and wherein a first site-specific recombinase recognition site of the pair of recombinase recognition sites is located in a sequence that encodes the stem sequence and the loop sequence of the sgRNA sequence and wherein a second site-specific recombinase recognition site of the pair of recombinase recognition sites is located in the sequence that encodes the stem sequence and the loop sequence of the sgRNA sequence.

2. The expression cassette of claim 1, wherein the length of the stem is at least 17 nucleotides or more.

3. The expression cassette of claim 1, wherein the recombinase recognition site is selected from frt, loxP, lox 66 or lox 71.

4. A construct comprising the cassette of claim 1.

5. The construct of claim 4, wherein the recombinase recognition site is selected from frt, loxP, lox 66 or lox 71.

6. A method of expressing an sgRNA of the CRISPR/Cas9 system upon recombinase stimulation, comprising:
  A) providing a cell with an expression cassette of claim 1;
  B) introducing or activating a recombinase in the cell, thereby removing the transcription disruption sequence; and
  C) cultivating the cell under conditions allowing expression of the sgRNA sequence.

7. The method according to claim 6, wherein during allowed expression the expressed single guide RNA forms a complex with a Cas9 protein.

8. The method of claim 6,
  wherein the expressed sgRNA forms a complex with a Cas9 protein and said complex modifies a target DNA at a sequence site hybridizing to the sgRNA.

9. The method of claim 6, wherein the transcription disruption sequence contains a Cas9 sequence, thereby expressing the Cas9 sequence until the transcription disruption sequence is excised upon recombinase mediated recombination.

* * * * *

SEQUENCE LISTING

```
<160> NUMBER OF SEQ ID NOS: 101

<210> SEQ ID NO 1
<211> LENGTH: 22
<212> TYPE: RNA
<213> ORGANISM: Artificial Sequence
<220> FEATURE:
<223> OTHER INFORMATION: crRNA
```

<400> SEQUENCE: 1
guuuuagagc uaugcuguuu ug                                              22

<210> SEQ ID NO 2
<211> LENGTH: 74
<212> TYPE: RNA
<213> ORGANISM: Artificial Sequence
<220> FEATURE:
<223> OTHER INFORMATION: tracrRNA

<400> SEQUENCE: 2
aaacagcaua gcaaguuaaa auaaggcuag uccguuauca acuugaaaaa guggcaccga      60
gucggugcuu uuuu                                                       74

<210> SEQ ID NO 3
<211> LENGTH: 82
<212> TYPE: RNA
<213> ORGANISM: Artificial Sequence
<220> FEATURE:
<223> OTHER INFORMATION: artificial sgRNA construct

<400> SEQUENCE: 3
guuuuagagc uagaaauagc aaguuaaaau aaggcuaguc cguuaucaac uugaaaaagu      60
ggcaccgagu cggugcuuuu uu                                              82

<210> SEQ ID NO 4
<211> LENGTH: 92
<212> TYPE: RNA
<213> ORGANISM: Artificial Sequence
<220> FEATURE:
<223> OTHER INFORMATION: artificial sgRNA construct

<400> SEQUENCE: 4
guuuaagagc uaugcuggaa acagcauagc aaguuuaaau aaggcuaguc cguuaucaac      60
uugaaaaagu ggcaccgagu cggugcuuuu uu                                   92

<210> SEQ ID NO 5
<211> LENGTH: 142
<212> TYPE: RNA
<213> ORGANISM: Artificial Sequence
<220> FEATURE:
<223> OTHER INFORMATION: artificial sgRNA construct

<400> SEQUENCE: 5
guuuuagagc uaggccaaca ugaggaucac ccaugucugc agggccuagc aaguuaaaau      60
aaggcuaguc cguuaucaac uuggccaaca ugaggaucac ccaugucugc agggccaagu     120
ggcaccgagu cggugcuuuu uu                                             142

<210> SEQ ID NO 6
<211> LENGTH: 122
<212> TYPE: RNA
<213> ORGANISM: Artificial Sequence
<220> FEATURE:
<223> OTHER INFORMATION: artificial sgRNA construct

<400> SEQUENCE: 6
guuuaagagc uaugcuggaa guccuauuc ucuagaaagu auaggaacuu ccagcauagc       60
aaguuuaaau aaggcuaguc cguuaucaac uugaaaaagu ggcaccgagu cggugcuuuu     120
uu                                                                   122

```
<210> SEQ ID NO 7
<211> LENGTH: 122
<212> TYPE: RNA
<213> ORGANISM: Artificial Sequence
<220> FEATURE:
<223> OTHER INFORMATION: artificial sgRNA construct

<400> SEQUENCE: 7
guuuaagagc uaugcugaua acuucguaua gcauacauua uacgaaguua ucagcauagc      60
aaguuuaaau aaggcuaguc cguuaucaac uugaaaaagu ggcaccgagu cggugcuuuu    120
uu                                                                   122

<210> SEQ ID NO 8
<211> LENGTH: 240
<212> TYPE: DNA
<213> ORGANISM: Artificial Sequence
<220> FEATURE:
<223> OTHER INFORMATION: artificial sgRNA construct

<400> SEQUENCE: 8
tttcccatga ttccttcata tttgcatata cgatacaagg ctgttagaga gataattgga      60
attaatttga ctgtaaacac aaagatatta gtacaaaata cgtgacgtag aaagtaataa    120
tttcttgggt agtttgcagt tttaaaatta tgttttaaaa tggactatca tatgcttacc    180
gtaacttgaa agtatttcga tttcttggct ttatatatct tgtggaaagg acgaaacacc    240

<210> SEQ ID NO 9
<211> LENGTH: 240
<212> TYPE: DNA
<213> ORGANISM: Artificial Sequence
<220> FEATURE:
<223> OTHER INFORMATION: artificial sgRNA construct

<400> SEQUENCE: 9
tttcccatga ttccttcata tttgcatata cgatacaagg ctgttagaga gataattgga      60
attaatttga ctgtaaacac aaagatatta gtacaaaata cgtgacgtag aaagtaataa    120
tttcttgggt agtttgcagt tttaaaatta tgttttaaaa tggactatca tatgcttacc    180
gtaacttgaa agtatataac ttcgtatact ttatattata cgaagttatg acgaaacacc    240

<210> SEQ ID NO 10
<211> LENGTH: 625
<212> TYPE: DNA
<213> ORGANISM: Artificial Sequence
<220> FEATURE:
<223> OTHER INFORMATION: artificial sgRNA construct

<400> SEQUENCE: 10
aggtcgtaga tctccgcggt taattaaaat gatacggcga ccaccgagat ctgtcttgat      60
ctaggagcta tcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg tcttcgctc gagagaagac    360 ctgttttaga gctagaaata gcaagttaaa ataaggctag tccgttatca acttgaaaaa    420
gtggcaccga gtcggtgctt ttttgtttta gagctagaaa tagcaagtta aaataaggct    480
agtccgtttt tagcgcgtgc gccaattctg cagacaaatg gctctagagg tacccgttaa    540
```

```
gatcggaaga gcacacgtct gaactccagt cacaaaatta tctcgtatgc cgtcttatgc    600
ttgttaatta acaattgctg gacga                                          625

<210> SEQ ID NO 11
<211> LENGTH: 685
<212> TYPE: DNA
<213> ORGANISM: Artificial Sequence
<220> FEATURE:
<223> OTHER INFORMATION: artificial sgRNA construct

<400> SEQUENCE: 11
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg gtcttcgctc gagagaagac    360
ctgttttaga gctaggccaa catgaggatc acccatgtct gcagggccta gcaagttaaa    420
ataaggctag tccgttatca acttggccaa catgaggatc acccatgtct gcagggccaa    480
gtggcaccga gtcggtgctt ttttgtttta gagctagaaa tagcaagtta aaataaggct    540
agtccgtttt tagcgcgtgc gccaattctg cagacaaatg gctctagagg tacccgttaa    600
gatcggaaga gcacacgtct gaactccagt cacaaaatta tctcgtatgc cgtcttatgc    660
ttgttaatta acaattgctg gacga                                          685

<210> SEQ ID NO 12
<211> LENGTH: 635
<212> TYPE: DNA
<213> ORGANISM: Artificial Sequence
<220> FEATURE:
<223> OTHER INFORMATION: artificial sgRNA construct

<400> SEQUENCE: 12
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg gtcttcgctc gagagaagac    360
ctgtttaaga gctatgctgg aaacagcata gcaagtttaa ataaggctag tccgttatca    420
acttgaaaaa gtggcaccga gtcggtgctt ttttgtttta gagctagaaa tagcaagtta    480
aaataaggct agtccgtttt tagcgcgtgc gccaattctg cagacaaatg gctctagagg    540
tacccgttaa gatcggaaga gcacacgtct gaactccagt cacaaaatta tctcgtatgc    600
cgtcttatgc ttgttaatta acaattgctg gacga                               635

<210> SEQ ID NO 13
<211> LENGTH: 622
<212> TYPE: DNA
<213> ORGANISM: Artificial Sequence
<220> FEATURE:
<223> OTHER INFORMATION: artificial sgRNA construct
```

<400> SEQUENCE: 13

```
aggtcgtaga tctccgcggt taattaaaat gatacggcga ccaccgagat ctgtcttgat      60
ctaggagcta ctcatcaacg gtcacatgtg agggcctatt cccatgatt ccttcatatt     120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
ttttagagct agaaatagca agttaaaata aggctagtcc gttatcaact gaaaaagtg     420
gcaccgagtc ggtgcttttt tgttttagag ctagaaatag caagttaaaa taaggctagt    480
ccgttttag cgcgtgcgcc aattctgcag acaaatggct ctagaggtac ccgttaagat     540
cggaagagca cacgtctgaa ctccagtcac aaaattatct cgtatgccgt cttatgcttg    600
ttaattaaca attgctggac ga                                             622
```

<210> SEQ ID NO 14
<211> LENGTH: 682
<212> TYPE: DNA
<213> ORGANISM: Artificial Sequence
<220> FEATURE:
<223> OTHER INFORMATION: artificial sgRNA construct

<400> SEQUENCE: 14

```
aggtcgtaga tctccgcggt taattaaaat gatacggcga ccaccgagat ctgtcttgat      60
ctaggagcta ctcatcaacg gtcacatgtg agggcctatt cccatgatt ccttcatatt     120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
ttttagagct aggccaacat gaggatcacc catgtctgca gggcctagca agttaaaata    420
aggctagtcc gttatcaact ggccaacat gaggatcacc catgtctgca gggccaagtg     480
gcaccgagtc ggtgcttttt tgttttagag ctagaaatag caagttaaaa taaggctagt    540
ccgttttag cgcgtgcgcc aattctgcag acaaatggct ctagaggtac ccgttaagat     600
cggaagagca cacgtctgaa ctccagtcac aaaattatct cgtatgccgt cttatgcttg    660
ttaattaaca attgctggac ga                                             682
```

<210> SEQ ID NO 15
<211> LENGTH: 632
<212> TYPE: DNA
<213> ORGANISM: Artificial Sequence
<220> FEATURE:
<223> OTHER INFORMATION: artificial sgRNA construct

<400> SEQUENCE: 15

```
aggtcgtaga tctccgcggt taattaaaat gatacggcga ccaccgagat ctgtcttgat      60
ctaggagcta ctcatcaacg gtcacatgtg agggcctatt cccatgatt ccttcatatt     120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
```

```
tttaagagct atgctggaaa cagcatagca agtttaaata aggctagtcc gttatcaact    420
tgaaaaagtg gcaccgagtc ggtgcttttt tgttttagag ctagaaatag caagttaaaa    480
taaggctagt ccgttttag cgcgtgcgcc aattctgcag acaaatggct ctagaggtac    540
ccgttaagat cggaagagca cacgtctgaa ctccagtcac aaaattatct cgtatgccgt    600
cttatgcttg ttaattaaca attgctggac ga                                  632
```

```
<210> SEQ ID NO 16
<211> LENGTH: 666
<212> TYPE: DNA
<213> ORGANISM: Artificial Sequence
<220> FEATURE:
<223> OTHER INFORMATION: artificial sgRNA construct

<400> SEQUENCE: 16
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccga taacttcgta tagcatacat    360
tatacgaagt tatgagctgg acggcgacgt aaagtttaag agctatgctg aaacagcat     420 agcaagttta ataaggcta gtccgttatc aacttgaaaa agtggcaccg agtcggtgct     480
tttttgtttt agagctagaa atagcaagtt aaaataaggc tagtccgttt ttagcgcgtg    540
cgccaattct gcagacaaat ggctctagag gtacccgtta agatcggaag agcacacgtc    600
tgaactccag tcacaaaatt atctcgtatg ccgtcttatg cttgttaatt aacaattgct    660
ggacga                                                               666
```

```
<210> SEQ ID NO 17
<211> LENGTH: 708
<212> TYPE: DNA
<213> ORGANISM: Artificial Sequence
<220> FEATURE:
<223> OTHER INFORMATION: artificial sgRNA construct

<400> SEQUENCE: 17
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccga taacttcgta tagcatacat    360
tatacgaagt tatttttttt tataacttcg tatagcatac attatacgaa gttatgagct    420
ggacggcgac gtaaagttta agagctatgc tggaaacagc atagcaagtt taaataaggc    480
tagtccgtta tcaacttgaa aaagtggcac cgagtcggtg cttttttgtt ttagagctag    540
aaatagcaag ttaaaataag gctagtccgt ttttagcgcg tgcgccaatt ctgcagacaa    600
atggctctag aggtacccgt taagatcgga agagcacacg tctgaactcc agtcacaaaa    660
ttatctcgta tgccgtctta tgcttgttaa ttaacaattg ctggacga                708
```

<210> SEQ ID NO 18
<211> LENGTH: 662
<212> TYPE: DNA
<213> ORGANISM: Artificial Sequence
<220> FEATURE:
<223> OTHER INFORMATION: artificial sgRNA construct

<400> SEQUENCE: 18

```
aggtcgtaga tctccgcggt taattaaaat gatacggcga ccaccgagat ctgtcttgat        60
ctaggagcta ctcatcaacg gtcacatgtg agggcctatt tcccatgatt ccttcatatt       120
tgcatatacg atacaaggct gttagagaga taattggaat taatttgact gtaaacacaa       180
agatattagt acaaaatacg tgacgtagaa agtaataatt tcttgggtag tttgcagttt       240
taaaattatg ttttaaaatg gactatcata tgcttaccgt aacttgaaag tatttcgatt       300
tcttggcttt atatatcttg tggaaaggac gaaacaccgg agctggacgg cgacgtaaag       360
tttaagagct atgctggaag ttcctattct ctagaaagta taggaacttc agcatagca        420
agtttaaata aggctagtcc gttatcaact tgaaaaagtg gcaccgagtc ggtgcttttt       480
tgttttagag ctagaaatag caagttaaaa taaggctagt ccgttttag cgcgtgcgcc        540
aattctgcag acaaatggct ctagaggtac ccgttaagat cggaagagca cacgtctgaa       600
ctccagtcac aaaattatct cgtatgccgt cttatgcttg ttaattaaca attgctggac       660
ga                                                                      662
```

<210> SEQ ID NO 19
<211> LENGTH: 632
<212> TYPE: DNA
<213> ORGANISM: Artificial Sequence
<220> FEATURE:
<223> OTHER INFORMATION: artificial sgRNA construct

<400> SEQUENCE: 19

```
aggtcgtaga tctccgcggt taattaaaat gatacggcga ccaccgagat ctgtcttgat        60
ctaggagcta ctcatcaacg gtcacatgtg agggcctatt tcccatgatt ccttcatatt       120
tgcatatacg atacaaggct gttagagaga taattggaat taatttgact gtaaacacaa       180
agatattagt acaaaatacg tgacgtagaa agtaataatt tcttgggtag tttgcagttt       240
taaaattatg ttttaaaatg gactatcata tgcttaccgt aacttgaaag tatataactt       300
cgtatacttt atattatacg aagttatgac gaaacaccgg agctggacgg cgacgtaaag       360
tttaagagct atgctggaaa cagcatagca agtttaaata aggctagtcc gttatcaact       420
tgaaaaagtg gcaccgagtc ggtgcttttt tgttttagag ctagaaatag caagttaaaa       480
taaggctagt ccgttttag cgcgtgcgcc aattctgcag acaaatggct ctagaggtac        540
ccgttaagat cggaagagca cacgtctgaa ctccagtcac aaaattatct cgtatgccgt       600
cttatgcttg ttaattaaca attgctggac ga                                     632
```

<210> SEQ ID NO 20
<211> LENGTH: 625
<212> TYPE: DNA
<213> ORGANISM: Artificial Sequence
<220> FEATURE:
<223> OTHER INFORMATION: artificial sgRNA construct

<400> SEQUENCE: 20

```
aggtcgtaga tctccgcggt taattaaaat gatacggcga ccaccgagat ctgtcttgat        60
ctaggagcta ctcatcaacg gtcacatgtg agggcctatt tcccatgatt ccttcatatt       120
```

```
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg tcttcgctc gagagaagac     360 ctgttttaga gctagaaata gcaagttaaa ataaggctag tccgttatca acttgaaaaa    420
gtggcaccga tcggtgctt ttttgtttta gagctagaaa tagcaagtta aaataaggct     480
agtccgtttt tagcgcgtgc gccaattctg cagacaaatg gctctagagg tacccgttaa    540
gatcggaaga gcacacgtct gaactccagt cacaaaatta tctcgtatgc cgtcttatgc    600
ttgttaatta acaattgctg gacga                                          625
```

<210> SEQ ID NO 21
<211> LENGTH: 685
<212> TYPE: DNA
<213> ORGANISM: Artificial Sequence
<220> FEATURE:
<223> OTHER INFORMATION: artificial sgRNA construct

<400> SEQUENCE: 21

```
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg tcttcgctc gagagaagac     360 ctgttttaga gctaggccaa catgaggatc acccatgtct gcagggccta gcaagttaaa    420
ataaggctag tccgttatca acttggccaa catgaggatc acccatgtct gcagggccaa    480
gtggcaccga tcggtgctt ttttgtttta gagctagaaa tagcaagtta aaataaggct     540
agtccgtttt tagcgcgtgc gccaattctg cagacaaatg gctctagagg tacccgttaa    600
gatcggaaga gcacacgtct gaactccagt cacaaaatta tctcgtatgc cgtcttatgc    660
ttgttaatta acaattgctg gacga                                          685
```

<210> SEQ ID NO 22
<211> LENGTH: 635
<212> TYPE: DNA
<213> ORGANISM: Artificial Sequence
<220> FEATURE:
<223> OTHER INFORMATION: artificial sgRNA construct

<400> SEQUENCE: 22

```
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg tcttcgctc gagagaagac     360 ctgttttaaga gctatgctgg aaacagcata gcaagtttaa ataaggctag tccgttatca    420
acttgaaaaa gtggcaccga tcggtgctt ttttgtttta gagctagaaa tagcaagtta     480
```
aaataaggct agtccgtttt tagcgcgtgc gccaattctg cagacaaatg gctctagagg    540
tacccgttaa gatcggaaga gcacacgtct gaactccagt cacaaaatta tctcgtatgc    600
cgtcttatgc ttgttaatta acaattgctg gacga                              635

<210> SEQ ID NO 23
<211> LENGTH: 622
<212> TYPE: DNA
<213> ORGANISM: Artificial Sequence
<220> FEATURE:
<223> OTHER INFORMATION: artificial sgRNA construct

<400> SEQUENCE: 23
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
ttttagagct agaaatagca agttaaaata aggctagtcc gttatcaact tgaaaaagtg    420
gcaccgagtc ggtgcttttt tgttttagag ctagaaatag caagttaaaa taaggctagt    480 ccgttttag cgcgtgcgcc aattctgcag acaaatggct ctagaggtac ccgttaagat    540
cggaagagca cacgtctgaa ctccagtcac aaaattatct cgtatgccgt cttatgcttg    600
ttaattaaca attgctggac ga                                            622

<210> SEQ ID NO 24
<211> LENGTH: 682
<212> TYPE: DNA
<213> ORGANISM: Artificial Sequence
<220> FEATURE:
<223> OTHER INFORMATION: artificial sgRNA construct

<400> SEQUENCE: 24
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
ttttagagct aggccaacat gaggatcacc catgtctgca gggcctagca agttaaaata    420
aggctagtcc gttatcaact tggccaacat gaggatcacc catgtctgca gggccaagtg    480
gcaccgagtc ggtgcttttt tgttttagag ctagaaatag caagttaaaa taaggctagt    540 ccgttttag cgcgtgcgcc aattctgcag acaaatggct ctagaggtac ccgttaagat    600
cggaagagca cacgtctgaa ctccagtcac aaaattatct cgtatgccgt cttatgcttg    660
ttaattaaca attgctggac ga                                            682

<210> SEQ ID NO 25
<211> LENGTH: 632
<212> TYPE: DNA
<213> ORGANISM: Artificial Sequence
<220> FEATURE:
<223> OTHER INFORMATION: artificial sgRNA construct

<400> SEQUENCE: 25

```
aggtcgtaga tctccgcggt taattaaaat gatacggcga ccaccgagat ctgtcttgat    60
ctaggagcta ctcatcaacg gtcacatgtg agggcctatt tcccatgatt ccttcatatt   120
tgcatatacg atacaaggct gttagagaga taattggaat taatttgact gtaaacacaa   180
agatattagt acaaaatacg tgacgtagaa agtaataatt tcttgggtag tttgcagttt   240
taaaattatg ttttaaaatg gactatcata tgcttaccgt aacttgaaag tatttcgatt   300
tcttggcttt atatatcttg tggaaaggac gaaacaccgg agctggacgg cgacgtaaag   360
tttaagagct atgctggaaa cagcatagca agtttaaata aggctagtcc gttatcaact   420
tgaaaaagtg gcaccgagtc ggtgcttttt tgttttagag ctagaaatag caagttaaaa   480
taaggctagt ccgttttttag cgcgtgcgcc aattctgcag acaaatggct ctagaggtac   540
ccgttaagat cggaagagca cacgtctgaa ctccagtcac aaaattatct cgtatgccgt   600
cttatgcttg ttaattaaca attgctggac ga                                 632
```

<210> SEQ ID NO 26
<211> LENGTH: 674
<212> TYPE: DNA
<213> ORGANISM: Artificial Sequence
<220> FEATURE:
<223> OTHER INFORMATION: artificial sgRNA construct

<400> SEQUENCE: 26

```
aggtcgtaga tctccgcggt taattaaaat gatacggcga ccaccgagat ctgtcttgat    60
ctaggagcta ctcatcaacg gtcacatgtg agggcctatt tcccatgatt ccttcatatt   120
tgcatatacg atacaaggct gttagagaga taattggaat taatttgact gtaaacacaa   180
agatattagt acaaaatacg tgacgtagaa agtaataatt tcttgggtag tttgcagttt   240
taaaattatg ttttaaaatg gactatcata tgcttaccgt aacttgaaag tatataactt   300
cgtatacttt atattatacg aagttatttt tttttataac ttcgtatact ttatattata   360
cgaagttatg acgaaacacc ggagctggac ggcgacgtaa agtttaagag ctatgctgga   420
aacagcatag caagtttaaa taaggctagt ccgttatcaa cttgaaaaag tggcaccgag   480
tcggtgcttt tttgttttag agctagaaat agcaagttaa ataaggctag tccgttttt   540
agcgcgtgcg ccaattctgc agacaaatgg ctctagaggt acccgttaag atcggaagag   600
cacacgtctg aactccagtc acaaaattat ctcgtatgcc gtcttatgct tgttaattaa   660
caattgctgg acga                                                    674
```

<210> SEQ ID NO 27
<211> LENGTH: 632
<212> TYPE: DNA
<213> ORGANISM: Artificial Sequence
<220> FEATURE:
<223> OTHER INFORMATION: artificial sgRNA construct

<400> SEQUENCE: 27

```
aggtcgtaga tctccgcggt taattaaaat gatacggcga ccaccgagat ctgtcttgat    60
ctaggagcta ctcatcaacg gtcacatgtg agggcctatt tcccatgatt ccttcatatt   120
tgcatatacg atacaaggct gttagagaga taattggaat taatttgact gtaaacacaa   180
agatattagt acaaaatacg tgacgtagaa agtaataatt tcttgggtag tttgcagttt   240
taaaattatg ttttaaaatg gactatcata tgcttaccgt aacttgaaag tatataactt   300
```

```
cgtatacttt atattatacg aagttatgac gaaacaccgg agctggacgg cgacgtaaag      360
tttaagagct atgctggaaa cagcatagca agtttaaata aggctagtcc gttatcaact      420
tgaaaaagtg gcaccgagtc ggtgcttttt tgttttagag ctagaaatag caagttaaaa      480
taaggctagt ccgttttag cgcgtgcgcc aattctgcag acaaatggct ctagaggtac       540
ccgttaagat cggaagagca cacgtctgaa ctccagtcac aaaattatct cgtatgccgt      600
cttatgcttg ttaattaaca attgctggac ga                                    632
```

<210> SEQ ID NO 28
<211> LENGTH: 709
<212> TYPE: DNA
<213> ORGANISM: Artificial Sequence
<220> FEATURE:
<223> OTHER INFORMATION: artificial sgRNA construct

<400> SEQUENCE: 28

```
aggtcgtaga tctccgcggt taattaaaat gatacggcga ccaccgagat ctgtcttgat       60
ctaggagcta ctcatcaacg gtcacatgtg agggcctatt tcccatgatt ccttcatatt      120
tgcatatacg atacaaggct gttagagaga taattggaat taatttgact gtaaacacaa      180
agatattagt acaaaatacg tgacgtagaa agtaataatt tcttgggtag tttgcagttt      240
taaaattatg ttttaaaatg gactatcata tgcttaccgt aacttgaaag tatttcgatt      300
tcttggcttt atatatcttg tggaaaggac gaaacaccga aacttcgta tagcatacat       360 tatacgaagt tatttttttt tataacttcg tatagcatac attatacgaa gttatggagc      420
tggacggcga cgtaaagttt aagagctatg ctggaaacag catagcaagt ttaaataagg      480
ctagtccgtt atcaacttga aaaagtggca ccgagtcggt gctttttgt tttagagcta      540 gaaatagcaa gttaaaataa ggctagtccg ttttagcgc gtgcgccaat tctgcagaca       600
aatggctcta gaggtacccg ttaagatcgg aagagcacac gtctgaactc cagtcacaaa      660
attatctcgt atgccgtctt atgcttgtta attaacaatt gctggacga                  709
```

<210> SEQ ID NO 29
<211> LENGTH: 667
<212> TYPE: DNA
<213> ORGANISM: Artificial Sequence
<220> FEATURE:
<223> OTHER INFORMATION: artificial sgRNA construct

<400> SEQUENCE: 29

```
aggtcgtaga tctccgcggt taattaaaat gatacggcga ccaccgagat ctgtcttgat       60
ctaggagcta ctcatcaacg gtcacatgtg agggcctatt tcccatgatt ccttcatatt      120
tgcatatacg atacaaggct gttagagaga taattggaat taatttgact gtaaacacaa      180
agatattagt acaaaatacg tgacgtagaa agtaataatt tcttgggtag tttgcagttt      240
taaaattatg ttttaaaatg gactatcata tgcttaccgt aacttgaaag tatttcgatt      300
tcttggcttt atatatcttg tggaaaggac gaaacaccga aacttcgta tagcatacat       360 tatacgaagt tatggagctg acggcgacg taaagtttaa gagctatgct ggaaacagca      420
tagcaagttt aaataaggct agtccgttat caacttgaaa aagtggcacc gagtcggtgc      480
ttttttgttt tagagctaga aatagcaagt taaaataagg ctagtccgtt tttagcgcgt      540
gcgccaattc tgcagacaaa tggctctaga ggtacccgtt aagatcggaa gagcacacgt      600
ctgaactcca gtcacaaaat tatctcgtat gccgtcttat gcttgttaat taacaattgc      660
tggacga                                                                667
```

<210> SEQ ID NO 30
<211> LENGTH: 704
<212> TYPE: DNA
<213> ORGANISM: Artificial Sequence
<220> FEATURE:
<223> OTHER INFORMATION: artificial sgRNA construct

<400> SEQUENCE: 30

```
aggtcgtaga tctccgcggt taattaaaat gatacggcga ccaccgagat ctgtcttgat      60
ctaggagcta ctcatcaacg gtcacatgtg agggcctatt tcccatgatt ccttcatatt     120
tgcatatacg atacaaggct gttagagaga taattggaat taatttgact gtaaacacaa     180
agatattagt acaaaatacg tgacgtagaa agtaataatt tcttgggtag tttgcagttt     240
taaaattatg ttttaaaatg gactatcata tgcttaccgt aacttgaaag tatttcgatt     300
tcttggcttt atatatcttg tggaaaggac gaaacaccgg agctggacgg cgacgtaaag     360
tttaagagct atgctgataa cttcgtatag catacattat acgaagttat ttttttttat     420
aacttcgtat agcatacatt atacgaagtt atcagcatag caagtttaaa taaggctagt     480
ccgttatcaa cttgaaaaag tggcaccgag tcggtgcttt tttgttttag agctagaaat     540
agcaagttaa ataaggcta gtccgttttt agcgcgtgcg ccaattctgc agacaaatgg     600
ctctagaggt acccgttaag atcggaagag cacacgtctg aactccagtc acaaaattat     660
ctcgtatgcc gtcttatgct tgttaattaa caattgctgg acga                     704
```

<210> SEQ ID NO 31
<211> LENGTH: 735
<212> TYPE: DNA
<213> ORGANISM: Artificial Sequence
<220> FEATURE:
<223> OTHER INFORMATION: artificial sgRNA construct

<400> SEQUENCE: 31

```
aggtcgtaga tctccgcggt taattaaaat gatacggcga ccaccgagat ctgtcttgat      60
ctaggagcta ctcatcaacg gtcacatgtg agggcctatt tcccatgatt ccttcatatt     120
tgcatatacg atacaaggct gttagagaga taattggaat taatttgact gtaaacacaa     180
agatattagt acaaaatacg tgacgtagaa agtaataatt tcttgggtag tttgcagttt     240
taaaattatg ttttaaaatg gactatcata tgcttaccgt aacttgaaag tatttcgatt     300
tcttggcttt atatatcttg tggaaaggac gaaacaccgg agctggacgg cgacgtaaag     360
tttaagagct atgctgataa cttcgtatag catacattat acgaagttat ttttttttt     420
tgcggccgcc cagaattctg gcctgcagga taacttcgta tagcatacat tatacgaagt     480
tatcagcata gcaagtttaa ataaggctag tccgttatca acttgaaaaa gtggcaccga     540
gtcggtgctt ttttgtttta gagctagaaa tagcaagtta aataaggct agtccgtttt     600
tagcgcgtgc gccaattctg cagacaaatg gctctagagg tacccgttaa gatcggaaga     660
gcacacgtct gaactccagt cacaaaatta tctcgtatgc cgtcttatgc ttgttaatta     720
acaattgctg gacga                                                     735
```

<210> SEQ ID NO 32
<211> LENGTH: 1519
<212> TYPE: DNA
<213> ORGANISM: Artificial Sequence
<220> FEATURE:
<223> OTHER INFORMATION: artificial sgRNA construct

<400> SEQUENCE: 32

```
aggtcgtaga tctccgcggt taattaaaat gatacggcga ccaccgagat ctgtcttgat      60
ctaggagcta ctcatcaacg gtcacatgtg agggcctatt cccatgatt ccttcatatt     120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
tttaagagct atgctgataa cttcgtatag catacattat acgaagttat ttttttttga    420
cgcgtaattc taccgggtag gggaggcgct tttcccaagg cagtctggag catgcgcttt    480
agcagcccg ctgggcactt ggcgctacac aagtggcctc tggcctcgca cacattccac     540
atccaccggt aggcgccaac cggctccgtt ctttggtggc cccttcgcgc caccttctac    600
tcctcccta gtcaggaagt tcccccccgc ccgcagctc gcgtcgtgca ggacgtgaca      660
aatggaagta gcacgtctca ctagtctcgt gcagatggac agcaccgctg agcaatggaa    720
gcgggtaggc ctttggggca gcggccaata gcagctttgc tccttcgctt tctgggctca    780
gaggctggga aggggtgggt ccggggggcgg gctcaggggc gggctcaggg gcggggcggg   840
cgcccgaagg tcctccggag gcccggcatt ctgcacgctt caaaagcgca cgtctgccgc    900
gctgttctcc tcttcctcat ctccgggcct ttcgacctgc agccaatatg gccaagcctt    960
tgtctcaaga agaatccacc ctcattgaaa gagcaacggc tacaatcaac agcatcccca   1020
tctctgagga ttacagcgtc gccagcgcag ctctctctag cgacggccgc atcttcactg   1080
gtgtcaatgt atatcatttt actggggggac cttgtgcaga actcgtggtg ctgggcactg   1140
ctgctgctgc ggcagctggc aacctgactt gtatcgtcgc gatcggaaat gagaacaggg    1200
gcatcttgag cccctgcgga cggtgccgac aggtgcttct cgatctgcat cctgggatca   1260
aagccatagt gaaggacagt gatggacagc cgacggcagt tgggattcgt gaattgctgc   1320
cctctggtta tgtgtgggag ggctgagggg atcataactt cgtatagcat acattatacg   1380
aagttatcag catagcaagt ttaaataagg ctagtccgtt atcaacttga aaaagtggca   1440
ccgagtcggt gcttttttat catcagtggt ccaggctcta gttttgactc aacaatatca   1500
ccagctgaag cctatagag                                                 1519
```

<210> SEQ ID NO 33
<211> LENGTH: 662
<212> TYPE: DNA
<213> ORGANISM: Artificial Sequence
<220> FEATURE:
<223> OTHER INFORMATION: artificial sgRNA construct

<400> SEQUENCE: 33

```
aggtcgtaga tctccgcggt taattaaaat gatacggcga ccaccgagat ctgtcttgat      60
ctaggagcta ctcatcaacg gtcacatgtg agggcctatt cccatgatt ccttcatatt     120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
tttaagagct atgctgataa cttcgtatag catacattat acgaagttat cagcatagca    420
agtttaaata aggctagtcc gttatcaact tgaaaaagtg gcaccgagtc ggtgcttttt    480
```

```
tgttttagag ctagaaatag caagttaaaa taaggctagt ccgttttag cgcgtgcgcc    540 aattctgcag acaaatggct ctagaggtac ccgttaagat cggaagagca cacgtctgaa    600
ctccagtcac aaaattatct cgtatgccgt cttatgcttg ttaattaaca attgctggac    660
ga                                                                   662

<210> SEQ ID NO 34
<211> LENGTH: 704
<212> TYPE: DNA
<213> ORGANISM: Artificial Sequence
<220> FEATURE:
<223> OTHER INFORMATION: artificial sgRNA construct

<400> SEQUENCE: 34
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
tttaagagct atgctggaag ttcctattct ctagaaagta taggaacttc ttttttttga    420
agttcctatt ctctagaaag tataggaact tccagcatag caagtttaaa taaggctagt    480
ccgttatcaa cttgaaaaag tggcaccgag tcggtgcttt tttgttttag agctagaaat    540
agcaagttaa ataaggcta gtccgttttt agcgcgtgcg ccaattctgc agacaaatgg    600
ctctagaggt acccgttaag atcggaagag cacacgtctg aactccagtc acaaaattat    660
ctcgtatgcc gtcttatgct tgttaattaa caattgctgg acga                    704

<210> SEQ ID NO 35
<211> LENGTH: 662
<212> TYPE: DNA
<213> ORGANISM: Artificial Sequence
<220> FEATURE:
<223> OTHER INFORMATION: artificial sgRNA construct

<400> SEQUENCE: 35
aggtcgtaga tctccgcggt taattaaaat gatacggcga ccaccgagat ctgtcttgat     60
ctaggagcta ctcatcaacg gtcacatgtg agggcctatt tcccatgatt ccttcatatt    120
tgcatatacg atacaaggct gttagagaga taattggaat taatttgact gtaaacacaa    180
agatattagt acaaaatacg tgacgtagaa agtaataatt tcttgggtag tttgcagttt    240
taaaattatg ttttaaaatg gactatcata tgcttaccgt aacttgaaag tatttcgatt    300
tcttggcttt atatatcttg tggaaaggac gaaacaccgg agctggacgg cgacgtaaag    360
tttaagagct atgctggaag ttcctattct ctagaaagta taggaacttc cagcatagca    420
agtttaaata aggctagtcc gttatcaact tgaaaaagtg gcaccgagtc ggtgcttttt    480
tgttttagag ctagaaatag caagttaaaa taaggctagt ccgttttag cgcgtgcgcc    540 aattctgcag acaaatggct ctagaggtac ccgttaagat cggaagagca cacgtctgaa    600
ctccagtcac aaaattatct cgtatgccgt cttatgcttg ttaattaaca attgctggac    660
ga                                                                   662

<210> SEQ ID NO 36
```

<211> LENGTH: 696
<212> TYPE: DNA
<213> ORGANISM: Artificial Sequence
<220> FEATURE:
<223> OTHER INFORMATION: artificial sgRNA construct

<400> SEQUENCE: 36

```
aggtcgtaga tctccgcggt taattaaaat gatacggcga ccaccgagat ctgtcttgat      60
ctaggagcta ctcatcaacg gtcacatgtg agggcctatt tcccatgatt ccttcatatt     120
tgcatatacg atacaaggct gttagagaga taattggaat taatttgact gtaaacacaa     180
agatattagt acaaaatacg tgacgtagaa agtaataatt tcttgggtag tttgcagttt     240
taaaattatg ttttaaaatg gactatcata tgcttaccgt aacttgaaag tatttcgatt     300
tcttggcttt atatatcttg tggaaaggac gaaacaccgg agctggacgg cgacgtaaag     360
tttaagagct atgctgataa cttcgtatag catacattat acgaagttat cagcatagca     420
agtttaaata aggctagtcc gttatcaact tgaaaaagtg gcaccgagtc ggtgcttttt     480
tgttttagag ctagaaatag caagttaaaa taaggctagt ccgttttag cgcgtgcgcc      540
aattctgcag ataacttcgt atagcataca ttatacgaag ttatacaaat ggctctagag     600
gtacccgtta gatcggaag agcacacgtc tgaactccag tcacaaaatt atctcgtatg     660
ccgtcttatg cttgttaatt aacaattgct ggacga                               696
```

<210> SEQ ID NO 37
<211> LENGTH: 522
<212> TYPE: DNA
<213> ORGANISM: Artificial Sequence
<220> FEATURE:
<223> OTHER INFORMATION: artificial sgRNA construct

<400> SEQUENCE: 37

```
aggtcgtaga tctccgcggt taattaaaat gatacggcga ccaccgagat ctgtcttgat      60
ctaggagcta ctcatcaacg gtcacatgtg agggcctatt tcccatgatt ccttcatatt     120
tgcatatacg atacaaggct gttagagaga taattggaat taatttgact gtaaacacaa     180
agatattagt acaaaatacg tgacgtagaa agtaataatt tcttgggtag tttgcagttt     240
taaaattatg ttttaaaatg gactatcata tgcttaccgt aacttgaaag tatttcgatt     300
tcttggcttt atatatcttg tggaaaggac gaaacaccgg agctggacgg cgacgtaaag     360
tttaagagct atgctgataa cttcgtatag catacattat acgaagttat acaaatggct     420
ctagaggtac ccgttaagat cggaagagca cacgtctgaa ctccagtcac aaaattatct     480
cgtatgccgt cttatgcttg ttaattaaca attgctggac ga                        522
```

<210> SEQ ID NO 38
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 38

```
gagtttgaat tccgacctga                                                  20
```

<210> SEQ ID NO 39
<211> LENGTH: 20
<212> TYPE: DNA
<213> ORGANISM: Artificial Sequence
<220> FEATURE:
<223> OTHER INFORMATION: gRNA coding sequence

```
<400> SEQUENCE: 39
ggactggttg acatcaataa                                                   20

<210> SEQ ID NO 40
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 40
gccggcccac gcgatcagga                                                   20

<210> SEQ ID NO 41
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 41
ttgtgtttta gggatccgga                                                   20

<210> SEQ ID NO 42
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 42
gcatctctaa tggatactga                                                   20

<210> SEQ ID NO 43
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 43
gtgtccttca caggctcgag                                                   20

<210> SEQ ID NO 44
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 44
tgtctgctat tgaagagtcc                                                   20

<210> SEQ ID NO 45
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 45
gcttgtgata gaaagtcgag                                                   20

<210> SEQ ID NO 46
```

```
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 46
ttttatactg ggatggaaag                                               20

<210> SEQ ID NO 47
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 47
gcagcttgtt gacactgcga                                               20

<210> SEQ ID NO 48
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 48
catttccctg gcctcaccag                                               20

<210> SEQ ID NO 49
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 49
ctttatagac caaagcacag                                               20

<210> SEQ ID NO 50
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 50
tcttctacct cctcaaaacg                                               20

<210> SEQ ID NO 51
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 51
ggagctttgt tagcatgcca                                               20

<210> SEQ ID NO 52
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 52
```

```
ggctgaatag tgttgccgat                                             20

<210> SEQ ID NO 53
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 53
gatctcaaag gaatcatcgg                                             20

<210> SEQ ID NO 54
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 54
gctgtgtaat caccgagacg                                             20

<210> SEQ ID NO 55
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 55
cttggaatcg agcctccaaa                                             20

<210> SEQ ID NO 56
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 56
cttccggtgg ggaagagaaa                                             20

<210> SEQ ID NO 57
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 57
ggaccagcgg aaaaccaaag                                             20

<210> SEQ ID NO 58
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 58
gagactcctc aaaagccccc                                             20

<210> SEQ ID NO 59
<211> LENGTH: 20
<212> TYPE: DNA
```

<213> ORGANISM: Artificial Sequence
<220> FEATURE:
<223> OTHER INFORMATION: gRNA coding sequence

<400> SEQUENCE: 59
aaacactttc gaggccacca					20

<210> SEQ ID NO 60
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 60
ggcagtaata gacaacacag					20

<210> SEQ ID NO 61
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 61
gatcctggag aagtgtcctt					20

<210> SEQ ID NO 62
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 62
ttatgcttct gtcaaaacga					20

<210> SEQ ID NO 63
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 63
ggaagtggac tacagcgcca					20

<210> SEQ ID NO 64
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 64
gcagtgctgt acttacgtgg					20

<210> SEQ ID NO 65
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 65
gcgcattgtg aagatggaag					20

<210> SEQ ID NO 66
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 66
ccttaccttt agcaaggcca                                              20

<210> SEQ ID NO 67
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 67
attagaccca taacttccat                                              20

<210> SEQ ID NO 68
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 68
acctacagat gctcctgccg                                              20

<210> SEQ ID NO 69
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 69
ttaggatccc aaacgtcatt                                              20

<210> SEQ ID NO 70
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 70
tattccctgt agaaatggga                                              20

<210> SEQ ID NO 71
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 71
gcacctggag taattcccgg                                              20

<210> SEQ ID NO 72
<211> LENGTH: 20
<212> TYPE: DNA
<213> ORGANISM: Artificial Sequence
<220> FEATURE:

<223> OTHER INFORMATION: gRNA coding sequence

<400> SEQUENCE: 72
gttccggcag gttttccaaa                                               20

<210> SEQ ID NO 73
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 73
ctacagggaa taggtcaccc                                               20

<210> SEQ ID NO 74
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 74
ccgaacagag attaacaaga                                               20

<210> SEQ ID NO 75
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 75
ttttggccca tagtccttgc                                               20

<210> SEQ ID NO 76
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 76
gcgagtactt actcttcgta                                               20

<210> SEQ ID NO 77
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 77
ccgcatcatt gcccacactc                                               20

<210> SEQ ID NO 78
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 78
catctggcac ctgtacccca                                               20

```
<210> SEQ ID NO 79
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 79
gctcggctgg atgaactagg                                               20

<210> SEQ ID NO 80
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 80
agggcttcat tggatgccaa                                               20

<210> SEQ ID NO 81
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 81
ctacaagctc atggaccacg                                               20

<210> SEQ ID NO 82
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 82
aacaccttgc cagttccagg                                               20

<210> SEQ ID NO 83
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 83
acatctagat aaacttcgag                                               20

<210> SEQ ID NO 84
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 84
ccacttggct cacctcagag                                               20

<210> SEQ ID NO 85
<211> LENGTH: 20
<212> TYPE: DNA
<213> ORGANISM: Artificial Sequence
<220> FEATURE:
<223> OTHER INFORMATION: gRNA coding sequence
```

```
<400> SEQUENCE: 85
ccacctctct cgcgttctcc                                                 20

<210> SEQ ID NO 86
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 86
tttctttcct cagatcgaag                                                 20

<210> SEQ ID NO 87
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 87
ggttcatctt taattcgtgg                                                 20

<210> SEQ ID NO 88
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 88
gggcacactc accattcaat                                                 20

<210> SEQ ID NO 89
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 89
cacgccggcc gacatgagcg                                                 20

<210> SEQ ID NO 90
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 90
tcgtcgtctc ctatcccgag                                                 20

<210> SEQ ID NO 91
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 91
tctgaccata ggccattgcg                                                 20

<210> SEQ ID NO 92
<211> LENGTH: 20
```

```
<212> TYPE: DNA
<213> ORGANISM: Artificial Sequence
<220> FEATURE:
<223> OTHER INFORMATION: gRNA coding sequence

<400> SEQUENCE: 92
gtacctcagt aatgccaaaa                                                20

<210> SEQ ID NO 93
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 93
cagctcaacg agaataaaca                                                20

<210> SEQ ID NO 94
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 94
ccagacacat cctattcacg                                                20

<210> SEQ ID NO 95
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 95
gtcaccctaa gcctacccag                                                20

<210> SEQ ID NO 96
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 96
gcagtcccgc tctcaatgag                                                20

<210> SEQ ID NO 97
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 97
gctcgagcat ctaatgaaga                                                20

<210> SEQ ID NO 98
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 98
```

```
gagtgctcct tacaaaaggg                                                  20

<210> SEQ ID NO 99
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 99
gctactccat acctgtttga                                                  20

<210> SEQ ID NO 100
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 100
cgctatccct ggaaagaagg                                                  20

<210> SEQ ID NO 101
<211> LENGTH: 20
<212> TYPE: DNA
<213> ORGANISM: Artificial Sequence
<220> FEATURE:
<223> OTHER INFORMATION: gRNA coding sequence

<400> SEQUENCE: 101
tccctcccca cagactccat                                                  20
```